US007763607B2

(12) United States Patent
Antel et al.

(10) Patent No.: US 7,763,607 B2
(45) Date of Patent: Jul. 27, 2010

(54) PHARMACEUTICAL COMPOSITIONS COMPRISING CBX CANNABINOID RECEPTOR MODULATORS AND POTASSIUM CHANNEL MODULATORS

(75) Inventors: Jochen Antel, Bad Münder (DE); Peter-Colin Gregory, Hannover (DE); Josephus Hubertus Maria Lange, Almere (NL); Michael Firnges, Barsinghausen (DE); Dania Reiche, Adelheidsdorf (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 0 days.

(21) Appl. No.: 11/796,716

(22) Filed: Apr. 26, 2007

(65) Prior Publication Data
US 2007/0254862 A1 Nov. 1, 2007

Related U.S. Application Data

(60) Provisional application No. 60/745,757, filed on Apr. 27, 2006, provisional application No. 60/745,760, filed on Apr. 27, 2006.

(51) Int. Cl.
*A61K 31/54* (2006.01)
*A61K 31/44* (2006.01)
*A61K 31/425* (2006.01)
(52) U.S. Cl. .................... 514/222.8; 514/342; 514/365; 514/866
(58) Field of Classification Search .............. 514/222.8, 514/342, 365, 866
See application file for complete search history.

(56) References Cited

U.S. PATENT DOCUMENTS

| 5,925,768 | A | 7/1999 | Gillard |
| 6,476,060 | B2 | 11/2002 | Lange et al. |
| 2002/0032193 | A1* | 3/2002 | Hansen et al. ........... 514/222.8 |
| 2004/0147581 | A1 | 7/2004 | Stephenson et al. |
| 2004/0266841 | A1 | 12/2004 | Lange et al. |
| 2005/0065189 | A1* | 3/2005 | Lange et al. ............. 514/342 |

FOREIGN PATENT DOCUMENTS

| WO | WO 9300337 A1 * | 1/1993 |
| WO | 01/32169 | 5/2001 |
| WO | WO 01/32169 | 5/2001 |
| WO | 01/70700 | 9/2001 |
| WO | 02/076949 | 10/2002 |
| WO | WO 02/076949 | 10/2002 |
| WO | 03/063758 | 8/2003 |
| WO | WO 03/063758 | 8/2003 |
| WO | 2004/045509 | 6/2004 |
| WO | 2005/028456 | 3/2005 |
| WO | WO 2005/028456 | 3/2005 |
| WO | 2005/075440 | 8/2005 |
| WO | WO 2005/075440 | 8/2005 |
| WO | 2006/045799 | 5/2006 |
| WO | WO 2006/045799 | 5/2006 |

OTHER PUBLICATIONS

Shen, Maoxing et al., The cannabinoid agonist VVin55,212-2 inhibits calcium channels by receptor mediated and direct pathways . . . Brain Res. 783 (1998) 77-84.
Hertzog D. L., Recent advances in the cannabinoids, Expert Opinion on Therapeutic Patents, vol. 14, No. 10 (2004) 1435-52.
Pertwee R. G., Pharmacology of cannabinoid CB1 and CB2 receptors, Pharmacology and Therapuetics, vol. 74, No. 2 (1997) 129-80.
Ferrari F. et al., Inhibitory effects of the cannabinoid against HU 210 on rat sexual behaviour, Physiology & Behaviour, vol. 69, No. 4/5 (Jun. 1, 2000) 547-54.
Walsh D. et al., The efficacy and tolerability of long-term use of dronabinol . . . , J. Pain and Symptom Manag., vol. 30, No. 6 (Dec. 2005) 493-95.
Breyne J. et al., Methanandamide hyperploarizes gastric arteries by stimulation . . . , J. Cardio. Pharm., vol. 47, No. 2 (Feb. 2006) 303-09.
Pirotte B et al., New insights into the development of ATP-sensitive potassium channel openers, Expert Opinion on Therapeutic Patents, vol. 15, No. 5 (2005) 497-504.
Extended European Search Report for European Patent Application 06 113 190, Sep. 13, 2006.
Extended European Search Report for European Patent Application 06 113 188, Oct. 19, 2006.
International Search Report for PCT/EP2007/053914, Jul. 25, 2007.
Written Opinion of the International Searching Authority for PCT/EP2007/053914, Jul. 25, 2007.
Muccioli et al., Latest advances in cannabinoid receptor antagonists and inverse agonists, Expert Opinion Therapeutic Patents, vol. 16, No. 10 (2006) p. 1405-1423.
Annual Update 2003/2004: Treatment of metabolic disorders, Drugs of the Future, vol. 29, No. 8 (2004) p. 868.
Breyne et al., Methanandamide hyperpolarizes gastric arteries by stimulation of TRPV1 receptors on perivascular CGRP containing nerves, J. Cardiovasc. Pharmacol. vol. 47, No. 2 (Feb. 2006) p. 303-309.
Pertwee, Pharmacology of cannabinoid CB1 and CB2 receptors, Pharmacol. Ther., vol. 74, No. 2 (1997) p. 129-180.
Shen et al., The cannabinoid agonist Win55,212-2 inhibits calcium channels by receptor-mediated and direct pathways in cultured rat hippocampal neurons, Brain Research, vol. 783 (1998) p. 77-84.
Walsh et al., The efficacy and tolerability of long-term use of dronabinol in cancer-related anorexia: A case series, Journal of Pain and Symptom Management, vol. 30, No. 6 (Dec. 2005) p. 493-495.
Ferrari et al., Inhibitory effects of the cannabinoid agonist HU 210 on rat sexual behaviour, Physiology & Behavior, vol. 69 (2000) p. 547-554.
Hertzog, Recent advances in the cannabinoids, Expert Opinion Therapeutic Patents, vol. 14, No. 10 (2004) p. 1435-1452.

(Continued)

*Primary Examiner*—Kevin Weddington
(74) *Attorney, Agent, or Firm*—Mayer Brown LLP

(57) ABSTRACT

Described herein are pharmaceutical compositions comprising therapeutically effective quantities of (i) a $K_{ATP}$ channel modulator; and (ii) a $CB_x$ modulator. Also described herein are methods of making and using these compositions.

17 Claims, No Drawings

OTHER PUBLICATIONS

Pirotte et al., New insights into the development of ATP-sensitive potassium channel openers, Expert Opinion Therapeutic Patents, vol. 15, No. 5 (2005) p. 497-504.

International Search Report for PCT/EP2007/053915, Jul. 25, 2007.

Written Opinion of the International Searching Authority for PCT/EP2007/053915, Jul. 25, 2007.

Gennaro, et al., "Remington: The Science and Practice of Pharmacy", 20th ed., pp. 1123-1125 (2000).

Golan, et al., "Principles of Pharmacology; The Pathiophysiologic Basis of Drug Therapy", 2nd ed., pp. 719-731 (2008).

Hager, et al., "Digoxin-quinidine interaction Pharmacokinetic evaluation," The New England Journal of Medicine, vol. 300(22), pp. 1238-1241 (1979).

Holt, et al., "Clinically significant interaction between digoxin and quinidine," British Medical Journal, 2(6202), p. 1401 (1979).

Kaletra, Abbott Laboratories, Product Information, REV-03-A181-R4 (Oct. 2008).

United States Food and Drug Administration, "Draft Guidance for Industry, Drug Interaction Studies—Study Design, Data Analysis, and Implications for Dosing and Labeling," Sep. 2006.

United States Food and Drug Administration, "Drug Development and Drug Interaction," available at http://www.fda.gov/Cder/drug/drugInteractions/default/htm (lasted updated on Feb. 24, 2009).

* cited by examiner

PHARMACEUTICAL COMPOSITIONS COMPRISING CBX CANNABINOID RECEPTOR MODULATORS AND POTASSIUM CHANNEL MODULATORS

CROSS REFERENCE TO RELATED APPLICATIONS

This application claims the benefit of U.S. Provisional Application Nos. 60/745,757 and 60/745,760 which were both filed on Apr. 27, 2006 and are both hereby incorporated by reference in their entirety to the extent permitted by law.

FIELD

Disclosed herein are pharmaceutical compositions comprising $K_{ATP}$ channel modulators and $CB_x$ modulators and the use of said pharmaceutical compositions for the treatment of one or more medical conditions such as, for example, obesity, diabetes mellitus, metabolic syndrome, syndrome X, insulinoma, familial hyperinsulemic hypoglycemia, male pattern baldness, detrusor hyperreactivity, asthma, neuroprotection, epilepsy, analgesia, cardioprotection, angina, cardioplegia, arrhythmia, coronary spasm, peripheral vascular disease, cerebral vasospasm, appetite regulation, neurodegeneration, pain, neuropathic pain, chronic pain, idiopathic pain and impotence in mammals such as humans.

BACKGROUND

As used herein, obesity is meant to comprise any increase in body fat that results in increased bodyweight and includes the medical definition of obesity. Thus, obesity also comprises any body fat increase not meeting the medical definition of obese, e.g. cosmetically overweight. The present disclosure relates to non-medical weight loss, such as cosmetic weight loss and includes improving body appearance in general. In one sense, obesity is understood to denominate a body weight more than 20% above the ideal body weight. In this sense, obesity is a major health concern in Western societies. It is estimated that about 97 million adults in the United States are overweight or obese. Obesity is largely the result of a positive energy balance as a consequence of increased ratio of caloric intake to energy expenditure. The molecular factors regulating food intake and body weight are not completely understood, but several genetic factors have been identified.

Epidemiological studies have shown that increasing degrees of overweight and obesity are important predictors of decreased life expectancy. Obesity causes or exacerbates many health problems, both independently and in association with other diseases. The problems associated with obesity, which can be serious and life-threatening, are well-known and generally include hypertension; type II diabetes mellitus; elevated plasma insulin concentrations; insulin resistance; dyslipidemias; hyperlipidemia; endometrial, breast, prostate and colon cancer; osteoarthritis; respiratory complications, such as obstructive sleep apnea; cholelithiasis; gallstones; arteriosclerosis; heart disease; abnormal heart rhythms; and heart arrythmias. Obesity is further associated with premature death and with a significant increase in mortality and morbidity from stroke, myocardial infarction, congestive heart failure, coronary heart disease, and sudden death.

Obesity is often treated by encouraging patients to lose weight by reducing their food intake or by increasing their exercise level and therefore increasing their energy output. A sustained weight loss of 5% to 10% of body weight has been shown to improve the co-morbidities associated with obesity, such as diabetes and hypertension, and can lead to improvement of obesity-related conditions such as osteoarthritis, sleep apnea and pulmonary and cardiac dysfunction.

Weight loss drugs that are currently used in monotherapy for the treatment of obesity have limited efficacy and significant side effects. During chronic treatment periods of greater than six months, the efficacy of most agents decreases yielding no more than 10% body weight loss compared to control. Obese humans can easily have a body mass of over 150 kg and would, therefore, need to lose more than 50% of their body mass to return to a normal body mass.

The term "metabolic syndrome" is meant to cover a complex of clinical manifestations which, besides central obesity, mainly comprises hypertension, in particular arterial hypertension; insulin resistance, in particular type II diabetes; glucose intolerance; dyslipoproteinaemia, in particular as hypertriglyceridaemia, accompanied by dyslipoproteinaemia occurring with lowered HDL-cholesterol, and also hyperuricaemia, which can lead to gout.

According to information from the American Heart Association, metabolic syndrome is closely linked to insulin resistance. Some people are genetically predisposed to insulin resistance. Acquired factors, such as excess body fat and physical inactivity, can elicit insulin resistance and metabolic syndrome in these people. Many people with insulin resistance have central obesity. The biological mechanisms at the molecular level between insulin resistance and metabolic risk factors are not fully understood and appear to be complex. One group of people at risk for developing metabolic syndrome is those with diabetes who have a defect in insulin action and cannot maintain a proper level of glucose in their blood. Another is people, mainly those with high blood pressure, who are non-diabetic and insulin-resistant but who compensate by secreting large amounts of insulin. This condition is known as hyperinsulinemia. A third group is heart attack survivors who, unlike hypertensives, have hyperinsulinemia without having abnormal glucose levels. Metabolic syndrome has become increasingly common in more developed countries like the United States, where it is estimated that between about 20% and 25% of US adults have metabolic syndrome. There are no well-accepted criteria for diagnosing the metabolic syndrome. The criteria proposed by the Third Report of the National Cholesterol Education Program (NCEP) Expert Panel on Detection, Evaluation, and Treatment of High Blood Cholesterol in Adults (Adult Treatment Panel III) are the most current and widely used. According to the Adult Treatment Panel III criteria, the metabolic syndrome is identified by the presence of three or more of these following components:

a. Central obesity as measured by waist circumference (Men—Greater than 40 inches; Women—Greater than 35 inches).
b. Fasting blood triglycerides greater than or equal to 150 mg/dL.
c. Blood HDL cholesterol (Men—Less than 40 mg/dL; Women—Less than 50 mg/dL).
d. Blood pressure greater than or equal to 130/85 mmHg.
e. Fasting glucose greater than or equal to 110 mg/dL.

The term "syndrome X" is closely related to the term "metabolic syndrome" and is typically used to indicate the identical disease or condition. According to information from the American Heart Association, the term "Syndrome X" refers, however, additionally to a heart condition where chest pain and electrocardiographic changes that suggest ischemic heart disease is present, but where there are no angiographic findings of coronary disease. Patients with cardiac syndrome X also sometimes have lipid abnormalities.

Therefore, one embodiment disclosed herein provides a more effective and/or more selective therapy for obesity, diabetes mellitus, metabolic syndrome and/or syndrome X.

ATP-sensitive potassium channel ($K_{ATP}$ channel) modulation has been linked to several potential clinical uses including diabetes, insulinoma, familial hyperinsulemic hypoglycemia, male pattern baldness, detrusor hyperreactivity, asthma, neuroprotection, epilepsy, analgesia, cardioprotection, angina, cardioplegia, arrhythmia, coronary spasm, hypertension, peripheral vascular disease, cerebral vasospasm, appetite regulation, neurodegeneration, pain, neuropathic pain, chronic pain, idiopathic pain and impotence (ref. Jahangir et al. *J. Mol. Cell. Cardiology*, 2005, 39, 99-112 and references cited therein).

Blockers of Kir6.2/SUR1 $K_{ATP}$ channels (e.g. repaglinde, tolbutamide and glibenclamide) stimulate insulin release and are used in the treatment of type II diabetes.

$K_{ATP}$ channel openers and their potential use in the inhibition of insulin secretion and/or the treatment of metabolic disorders are discussed in U.S. Pat. No. 6,492,130; WO 02/00223; WO 02/00665 or from R. D. Carr et al., Diabetes 52 (2003) 2513-2518 or J. B. Hansen et al., Current Medicinal Chemistry 11 (2004) 1595-1615.

The beneficial role of the specific $K_{ATP}$ channel opener diazoxide in the treatment of i.a. metabolic syndrome is discussed in U.S. Pat. No. 5,284,845 or U.S. Pat. No. 6,197,765 or from R. Alemzadeh et al., Endocrinology 133 (2) (1993) 705-712 or R. Alemzadeh et al., Journal of Clinical Endocrinology and Metabolism 83 (6) (1998) 1911-1915.

The $K_{ATP}$ channel couples glucose metabolism to insulin secretion. Defective regulation of $K_{ATP}$ channel activity has been reported to contribute to the etiology of type 2 diabetes (ref. Ashcroft, *J. Clin. Investig.* 2005, 115 (8), 2047-2057 and references cited therein). The $K_{ATP}$, channel is an octameric complex of 4 Kir6.x (x=1 or 2) and 4 regulatory SURy subunits (Y=1, 2A or 2B). The SUR1 regulatory subunit is in particular found in the human pancreas and brain (ref. Aguilar-Bryan et al., Science 1995, 268, 423-426). The $K_{ATP}$ Kir6.2/SUR1 combination exists in the pancreas. Its structure has been determined recently (ref. Mikhailov, *EMBO Journal*, 2005, 24, (23), 4166-4175). Advances in the discovery of ATP-sensitive potassium channel openers have been recently reviewed in Pirotte et al., *Exp Opin. Ther. Patents* 2005, 15 (5), 497-504 and Hansen, *Curr. Med. Chem.* 2006, 13, 361-76.

Insulin is the main hormone involved in blood glucose homeostasis. Insulin is involved in the regulation of glycaemia and as a consequence related to type I and type II diabetes. Additionally, insulin is involved in lipogenesis and weight gain, provoking an anorexigenic action as it provokes satiety when acting in the brain (ref. Juan-Pico et al., *Cell Calcium* 2006, 39, 155-163 and references cited therein).

Therefore, the regulation of insulin secretion will be useful in the treatment of diseases such as diabetus mellitus type I, diabetus mellitus type II, obesity, metabolic syndrome and syndrome X.

The endocannabinoid system (refs. (a) De Petrocellis, L. et al., *Br. J. Pharmacol.* 2004 141, 765-774; (b) Di Marzo, V. et al., *Nature Rev. Drug Discov.* 2004, 3, 771-784; (c) Lambert, D. M. and Fowler, C. J. *J. Med. Chem.* 2005, 48, 5059-5087) has been reported to play a role in the physiological regulation of food intake, energy balance and glucose and lipid metabolism. The existence of both cannabinoid $CB_1$ and $CB_2$ receptors has been demonstrated in the endocrine pancreas. It has been reported that the endogenous $CB_{1/2}$ receptor agonist 2-arachidonoyl glycerol (2-AG) (FIG. 2) through $CB_2$ receptors regulates $[Ca^{2+}]_i$ signals in β-cells in the endocrine pancreas and, as a consequence (as was concluded by Juan-Pico et al.), it decreases insulin secretion (ref. Juan-Pico et al., *Cell Calcium* 2006, 39, 155-163). Recent advances in the field of $CB_2$ receptor ligands have been reviewed by Raitio et al. (*Curr. Med. Chem.* 2005, 12, 1217-1237).

It has now surprisingly been found that a novel combination therapy which comprises administering a first $K_{ATP}$ channel modulator and a first $CB_x$ modulator to a patient in need thereof can provide an effective and/or selective therapy for a variety of medical conditions such as obesity, diabetes mellitus, metabolic syndrome, syndrome X, insulinoma, familial hyperinsulemic hypoglycemia, male pattern baldness, detrusor hyperreactivity, asthma, neuroprotection, epilepsy, analgesia, cardioprotection, angina, cardioplegia, arrhythmia, coronary spasm, peripheral vascular disease, cerebral vasospasm, appetite regulation, neurodegeneration, pain, neuropathic pain, chronic pain, idiopathic pain and impotence in mammals such as humans. More specifically, due to the long term effect of therapy with a $K_{ATP}$ channel modulator, this new combination therapy is particularly suited for the treatment of diabetes mellitus, metabolic syndrome and/or syndrome X in patients exposed to an elevated risk of acquiring such diseases, such as patients with established obesity. However, due to its direct effect on glucose metabolism, the novel combination therapy according to the present disclosure is also well suited to treat type II diabetes and insulin resistance in patients without concomitant obesity.

SUMMARY

One embodiment described herein relates to a pharmaceutical composition comprising therapeutically effective quantities of:

a) a $K_{ATP}$ channel modulator; and b) a $CB_x$ modulator;

wherein the $CB_x$ modulator is selected from the group consisting of: $CB_1$ agonists, $CB_2$ agonists, $CB_2$ partial agonists, $CB_2$ antagonists, $CB_2$ inverse agonists, compounds having both $CB_1$ agonist and $CB_2$ agonist properties, and mixtures thereof.

Other embodiments described herein relate to methods of using a $K_{ATP}$ channel modulator combined with a $CB_x$ modulator for the treatment of a medical condition in a mammal. Another embodiment described herein relates to a method of treating a medical condition by administering therapeutically effective amounts of both a $K_{ATP}$ channel modulator and a $CB_x$ channel modulator. A further embodiment described herein relates to a pharmaceutical composition prepared by the process of combining a $K_{ATP}$ channel modulator with a $CB_x$ modulator.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit

DESCRIPTION

While the present invention is capable of being embodied in various forms, the description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

One embodiment described herein is a pharmaceutical composition comprising therapeutically effective quantities of:

a) a $K_{ATP}$ channel modulator; and
b) a $CB_x$ modulator;

wherein the $CB_x$ modulator is selected from the group consisting of: $CB_1$ agonists, $CB_2$ agonists, $CB_2$ partial agonists, $CB_2$ antagonists, $CB_2$ inverse agonists, compounds having both $CB_1$ agonist and $CB_2$ agonist properties, and mixtures thereof. A further embodiment includes one or more pharmaceutically acceptable excipients which can be used to create a dosage form which is suitable for oral administration. In a further embodiment, the oral dosage form is selected from the group consisting of tablets, coated tablets, capsules, syrups, elixirs and suspensions as well as other oral dosages known to a person of ordinary skill in the art. Further embodiments also include dosage forms and routes of administration known to those of skill in the art such as those set forth in Remington, The Science and Practice of Pharmacy. $20^{th}$ edition which is hereby incorporated by reference in it entirety.

A further embodiment described herein includes a pharmaceutical composition comprising therapeutically effective quantities of a $K_{ATP}$ channel modulator and a CBx modulator wherein the $K_{ATP}$ modulator is selected from the group consisting of: $K_{ATP}$ channel openers, partial $K_{ATP}$ channel openers, $K_{ATP}$ channel closing agents, $K_{ATP}$ channel blocking agents, and mixtures thereof as well as other $K_{ATP}$ channel modulators known to persons of ordinary skill in the art such as those set forth in The Merck Index, $14^{th}$ edition which is hereby incorporated by reference in it entirety. In a further embodiment, suitable $K_{ATP}$ modulators include those which modulate one or more of the Kir6.2/SUR1 $K_{ATP}$ channel, the Kir6.2/SUR2B $K_{ATP}$ channel, the Kir6.1/SUR2B $K_{ATP}$ channel and the Kir6.2/SUR2A $K_{ATP}$ channel.

An additional embodiment includes a method of using a $K_{ATP}$ channel modulator for the treatment of a medical condition in a mammal comprising the steps of combining the $K_{ATP}$ channel modulator with a $CB_x$ modulator; and administering the combined $K_{ATP}$ channel modulator and $CB_x$ modulator to the mammal. In a further embodiment, the method of using the $K_{ATP}$ channel modulator for the treatment of a medical condition includes a $CB_x$ modulator selected from the group consisting of $CB_1$ agonists, $CB_2$ agonists, $CB_2$ partial agonists, $CB_2$ antagonists, $CB_2$ inverse agonists, compounds having both $CB_1$ agonist and $CB_2$ agonist properties, and mixtures thereof. In a further embodiment the medical condition is selected from the group consisting of: obesity, diabetes mellitus, metabolic syndrome, syndrome X, insulinoma, familial hyperinsulemic hypoglycemia, male pattern baldness, detrusor hyperreactivity, asthma, neuroprotection, epilepsy, analgesia, cardioprotection, angina, cardioplegia, arrhythmia, coronary spasm, peripheral vascular disease, cerebral vasospasm, appetite regulation, neurodegeneration, pain, neuropathic pain, chronic pain, idiopathic pain and impotence. In a further embodiment, the metabolic syndrome and syndrome X are comprised of disorders selected from the group consisting of: hypertension; insulin resistance; glucose intolerance; and dyslipoproteinaemia.

In a further embodiment, the treatment of a medical condition includes the $K_{ATP}$ channel modulator functioning as a $CB_x$ modulator; or the $CB_x$ modulator functioning as a $K_{ATP}$ channel modulator; provided that the $K_{ATP}$ channel modulator and the $CB_x$ modulator are different compounds.

An additional embodiment includes a method of treating a medical condition in a subject in need thereof comprising the steps of administering to the subject therapeutically effective amounts of both a $K_{ATP}$ channel modulator and a $CB_x$ modulator. In a further embodiment the $CB_x$ modulator is selected from the group consisting of: $CB_1$ agonists, $CB_2$ agonists, $CB_2$ partial agonists, $CB_2$ antagonists, $CB_2$ inverse agonists, compounds having both $CB_1$ agonist and $CB_2$ agonist properties, and mixtures thereof. In yet an additional embodiment the medical condition to be treated is selected from the group consisting of obesity, diabetes mellitus, metabolic syndrome, syndrome X, insulinoma, familial hyperinsulemic hypoglycemia, male pattern baldness, detrusor hyperreactivity, asthma, neuroprotection, epilepsy, analgesia, cardioprotection, angina, cardioplegia, arrhythmia, coronary spasm, peripheral vascular disease, cerebral vasospasm, appetite regulation, neurodegeneration, pain, neuropathic pain, chronic pain, idiopathic pain and impotence.

In a further embodiment, the treatment of a medical condition includes the $K_{ATP}$ channel modulator and the $CB_x$ modulator being administered simultaneously in the same or different dosage form or sequentially in the same or different dosage form. A further embodiment includes the $K_{ATP}$ channel modulator and the $CB_x$ modulator being administered simultaneously in an oral dosage form.

In a further embodiment, the treatment of a medical condition includes the $K_{ATP}$ channel modulator also functioning as a $CB_x$ modulator; or the $CB_x$ modulator also functioning as a $K_{ATP}$ channel modulator; provided that the $K_{ATP}$ channel modulator and the $CB_x$ modulator are different compounds. In a further embodiment, suitable $K_{ATP}$ modulators include those which modulate one or more of the Kir6.2/SUR1 $K_{ATP}$ channel, the Kir6.2/SUR2B $K_{ATP}$ channel, the Kir6.1/SUR2B $K_{ATP}$ channel and the Kir6.2/SUR2A $K_{ATP}$ channel.

A further embodiment described herein includes a pharmaceutical composition prepared by the process comprising the step of combining a $K_{ATP}$ channel modulator with a $CB_x$ modulator. In further embodiment, the $CB_x$ modulator is selected from the group consisting of $CB_1$ agonists, $CB_2$ agonists, $CB_2$ partial agonists, $CB_2$ antagonists, $CB_2$ inverse agonists, compounds having both $CB_1$ agonist and $CB_2$ agonist properties, and mixtures thereof. In an additional embodiment, the $K_{ATP}$ channel modulator and the $CB_x$ modulator are present in a combined amount effective for the treatment of a medical condition selected from the group consisting of obesity, diabetes mellitus, metabolic syndrome, syndrome X, insulinoma, familial hyperinsulemic hypoglycemia, male pattern baldness, detrusor hyperreactivity, asthma, neuroprotection, epilepsy, analgesia, cardioprotection, angina, cardioplegia, arrhythmia, coronary spasm, peripheral vascular disease, cerebral vasospasm, appetite regulation, neurodegeneration, pain, neuropathic pain, chronic pain, idiopathic pain and impotence in mammals.

The terms "treat", "treated", "treating" and "treatment" are to be broadly understood as referring to any response to, or anticipation of, a medical condition in a mammal, particularly a human, and includes but is not limited to:

(i) preventing the medical condition from occurring in a subject, which may or may not be predisposed to the condition, but has not yet been diagnosed with the condition and, accordingly, the treatment constitutes prophylactic treatment for the medical condition;

(ii) inhibiting the medical condition, i.e., arresting, slowing or delaying the on-set, development or progression of the medical condition; or (iii) relieving the medical condition, i.e., causing regression of the medical condition.

The disclosure of U.S. patent application Ser. No. 11/796,740, filed on Apr. 26, 2007 which also claims the benefit of U.S. Provisional Application Nos. 60/745,757 and 60/745,760 (both filed on Apr. 27, 2006) is hereby incorporated by reference in its entirety to the extent permitted by law.

Suitable $K_{ATP}$ channel modulators are compounds selected from the group consisting of $K_{ATP}$, channel openers, partial $K_{ATP}$ channel openers, $K_{ATP}$ channel closing agents, $K_{ATP}$ channel blocking agents, and mixtures thereof. Suitable $K_{ATP}$ channel modulators are compounds which have effects as modulators at the Kir6.2/SUR1 $K_{ATP}$ channel, the Kir6.2/SUR2B $K_{ATP}$ channel, the Kir6.1/SUR2B $K_{ATP}$ channel, and/or the Kir6.2/SUR2A $K_{ATP}$ channel. Suitable compounds are those which exhibit an $IC_{50}$ value [μmol] of less than 50 in a test for the affinity of the compounds in binding to the sulfonylurea (SUR) and potassium channel opener site (KCO) of rat and/or human isoforms of SUR1 and/or SUR2B—e.g. the test model provided below. Suitable compounds are those with an effect as openers at the Kir6.2/SUR1 $K_{ATP}$ channel, such as selective openers at the Kir6.2/SUR1 $K_{ATP}$ channel. A compound with an effect as opener at the Kir6.2/SUR1 $K_{ATP}$ channel is understood to be selective if its $IC_{50}$ value at the Kir6.2/SUR1 $K_{ATP}$ channel, as measured in the aforementioned binding test, is less than half, more preferred only a quarter, of the $IC_{50}$ value of that same compound at the Kir6.2/SUR2B $K_{ATP}$ channel, the Kir6.1/SUR2B $K_{ATP}$ channel, and/or at the Kir6.2/SUR2A $K_{ATP}$ channel. Specific compounds which are suitable as $K_{ATP}$ channel openers according to the present disclosure may be selected from, but not limited to, the group consisting of pinacidil; cromakalim; diazoxide; BPDZ 44; BPDZ 49; BPDZ 62; BPDZ 73; BPDZ 79; BPDZ 83; BPDZ 109; BPDZ 154; BPDZ 216 (NNC 55-9216); NN414 (all: see e.g. Hansen et al.); NNC 55-0118 (see e.g. T. M. Tagmose et al., J. Med. Chem. 47 (2004) 3202-3211): NNC 55-0462 (see e.g. Hansen et al.), MCC-134 (see e.g. M. J. Coghlan et al., J. Med. Chem. 44 (2001) 1627-1653); losimendan; SR 47063, WAY 135201, and mixtures thereof.

As used herein, $CB_x$ modulator includes compounds which function as $CB_1$ agonists, $CB_2$ agonists, $CB_2$ partial agonists, $CB_2$ antagonists, $CB_2$ inverse agonists, compounds having both $CB_1$ agonist and $CB_2$ agonist properties, and mixtures thereof. $CB_x$ modulators also includes other compounds known to those of ordinary skill in the art to modulate one or more cannabinoid receptors.

Suitable $CB_1$ agonists are compounds which bind to and activate the $CB_1$ receptor. Those compounds which are effective exhibit an $IC_{50}$ value [μmol] of more than 50 in a test for the affinity of the compounds in binding to the CB1 receptor. Suitable $CB_2$ agonists are preferably compounds which bind to and activate the $CB_2$ receptor. Effective compounds are those which exhibit an $IC_{50}$ value [μmol] of more than 50 in a test for the affinity of the compounds in binding to the $CB_2$ receptor. Specific compounds which are suitable as $CB_1$ agonists or $CB_2$ agonists according to the present disclosure may be selected from, but not limited to, the group consisting of: L759633; L759656; {4-[4-(1,1-dimethyl-heptyl)-2,6-dimethoxy-phenyl]-6,6-dimethyl-bicyclo-[3.1.1]hept-2-en-2-yl}-methanol (HU308); JWH015; (2-iodo-5-nitro-phenyl)-[1-(1-methyl-piperidin-2-ylmethyl)-1H-indol-3-yl]-methanone (AM-1241); 3-(1,1-dimethyl-butyl)-6,6,9-trimethyl-6a,7,10,10a-tetrahydro-6H-benzo[c]-chromene (JWH133); N-adamantantyl-4-pentyl-5-phenyl-thiazole-2-carboxamide; 6,6,9-trimethyl-3-pentyl-6a,7,8,10a-tetrahydro-6H-benzo[c]chromen-1-ol; (bicyclo[2.2.1]hept-2-ylamino)-(5-pentyl-4-phenyl-thiazol-2-yl)-methane; dronabinol; dimethyl-heptyl)-2-[5-hydroxy-2-(3-hydroxy-propyl)-cyclohexyl]-phenol (CP-55,940); (2-methyl-3-morpholin-4-ylmethyl-3,4-dihydro-5-oxa-2a-aza-acenaphthylen-1-yl)-naphthalen-1-yl-methanone (WIN-55,212-2); HU210; ACEA; ACPA; N-adamantyl-4-pentyl-5-phenyl-thiazole-2-carboxamide; methanandamide; anandamide; 2-arachidonoyl glycerol; 2-icosa-5,8,11,14-tetraenyloxy-propane-1,3-diol (noladin ether); BAY 38-7271; SAB-378; BAY 59-3074; O-1057; GW-1000; PRS-211375; PRS-211359; PRS-211355; PRS-211096; PXS-2076; AM-577; GW-842166X; and mixtures thereof. Other suitable $CB_1$ agonists or $CB_2$ agonists have been described in the literature, for example: Thakur et al., Mini-Rev. Med. Chem. 2005, 5, 631-640; Palmer et al., Chem. Phys. Lipids 2002, 121, 3-19; Hertzog, Expert Opin. Ther. Patents, 2004, 14, 1435-1452; Huffman, Curr. Med. Chem. 1999, 6, 705-720; Reggio, Curr. Pharm. Des. 2003, 9, 1607-1633; Padgett, Life Sci. 2005, 77, 1767-1798; Goya and Jagerovic, Expert. Opin. Ther. Patents, 2000, 10, 1529-1538.

In one embodiment, the $CB_2$ agonist is a selective $CB_2$ agonist and is selected from, but not limited to, the group consisting of: 3-(1,1-dimethyl-butyl)-6,6,9-trimethyl-6a,7,10,10a-tetrahydro-6H-benzo[c]chromene (JWH133); L759633; L759656; {4-[4-(1,1-dimethyl-heptyl)-2,6-dimethoxy-phenyl]-6,6-dimethyl-bicyclo[3.1.1]hept-2-en-2-yl}-methanol (HU308); JWH015; (2-iodo-5-nitro-phenyl)-[1-(1-methyl-piperidin-2-ylmethyl)-1H-indol-3-yl]-methanone (AM-1241); and mixtures thereof. See for additional information on these compounds: L759633, L759656: Br. J. Pharmacol. 1999, 126, 665-672; Proc. Natl. Acad. Sci. USA 2003, 100, 10529-10533; Proc. Natl. Acad. Sci. USA 1999, 96, 14228-14233; Bioorg. Med. Chem. 1999, 7, 2905-2914.

Other suitable $CB_1$ agonists or $CB_2$ agonists include those which have been identified in the literature and/or known to a person of ordinary skill in the art even though the particular compounds are not specifically listed herein.

Suitable $CB_2$ antagonists or suitable $CB_2$ inverse agonists are compounds which bind to the $CB_2$ receptor but do not produce agonistic or partial agonistic effects. Effective compounds are those exhibiting an $IC_{50}$ value [μmol] of more than 50 in a test for the affinity of the compounds in binding to the $CB_2$ receptor. Specific compounds which are suitable as $CB_2$ antagonists or suitable $CB_2$ inverse agonists may be selected from, but not limited to, the group consisting of: (1) compounds described in documents WO01/0588869, PCT/EP2006/060009, WO2004/014825; EP1142877; US2002/0072529; WO02/062750; U.S. Pat. No. 6,509,352; and (2) compounds selected from the group consisting of: N-{1,3,3-Trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide (SR-144528), JTE-907, AM630, and mixtures thereof; and (3) mixtures of compounds selected from (1) and (2). Other suitable $CB_2$ antagonists or suitable $CB_2$ inverse agonists have been described in the literature, for example: Lavey et al. Bioorg. Med. Chem. Lett. 2005, 15, 783-786; Shankar et al. Bioorg. Med. Chem. Lett. 2005, 15, 4417-4420;

Iwamura et al. *J. Pharmacol. Exp. Ther.* 2001, 296, 420-425. Additional information on CB antagonism as it is related to inverse agonism and the active/inactive state of CB receptors can be found, for example, in Reggio, *Curr. Pharm. Des.* 2003, 9, 1607-1633; Tuccinardi et al. *J. Med. Chem.* 2006, 49, 984-994 and Pertwee, *Life Sci.* 2005, 76, 1307-1324. Other suitable $CB_2$ antagonists or suitable $CB_2$ inverse agonists include those which have been identified in the literature even though not specifically listed herein.

Suitable compounds having both $CB_1$ agonist and $CB_2$ agonist properties are those which bind to the $CB_1$ as well as to the $CB_2$ receptor. Effective compounds are those exhibiting an $IC_{50}$ value [μmol] of more than 50 in a test for the affinity of the compounds in binding to the $CB_1$ as well as to the $CB_2$ receptor. Specific compounds which are suitable as dually acting compounds which are both a $CB_1$ agonist and a $CB_2$ agonists according to the present disclosure may be selected from, but not limited to, the group consisting of: dronabinol; HU210; 2-icosa-5,8,11,14-tetraenyloxy-propane-1,3-diol (noladin ether); N-adamantanyl-4-pentyl-5-phenyl-thiazole-2-carboxamide; and mixtures thereof.

Also suitable for use in the various embodiments described and claimed herein is any combination or mixture of the $CB_x$ modulators listed herein, including, $CB_1$ agonists, $CB_2$ agonists, $CB_2$ partial agonists, $CB_2$ antagonists, $CB_2$ inverse agonists and compounds having both $CB_1$ agonist and $CB_2$ agonist properties.

In one embodiment, the $K_{ATP}$ channel modulator is a $K_{ATP}$ channel opener.

$CB_x$ modulators suitable for use as a $K_{ATP}$ channel modulator are selected from, but not limited to the group consisting of: 3-(1,1-dimethyl-butyl)-6,6,9-trimethyl-6a,7,10,10a-tetrahydro-6H-benzo[c]chromene; N-Adamantyl-4-pentyl-5-phenyl-thiazole-2-carboxamide; N-{1,3,3-Trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide; (2-Iodo-5-nitro-phenyl)-[1-(1-methyl-piperidin-2-ylmethyl)-1H-indol-3-yl]-methanone; {-4-[4-(1,1-Dimethyl-heptyl)-2,6-dimethoxy-phenyl]-6,6-dimethyl-bicyclo[3.1.1]hept-2-en-2-yl}-methanol; 3-(1,1-Dimethyl-heptyl)-9-hydroxymethyl-6,6-dimethyl-6a,7,10,10a-tetrahydro-6H-enzo[c]chromen-1-ol; Icosa-5,8,11,14-tetraenoic acid 2-hydroxy-1-hydroxymethyl-ethyl ester; 1-Aziridin-1-yl-henicosa-6,9,12,15-tetraen-2-one; Noladineether; 4,4,4-Trifluoro-butane-1-sulfinic acid 3-(2-hydroxymethyl-indan-4-yloxy)-phenyl ester, compound with form aldehyde; 7-Methoxy-2-oxo-8-pentyloxy-1,2-dihydro-quinoline-3-carboxylic acid (benzo[1,3]dioxol-5-ylmethyl)-amide; N-(1-{-4-[4-Chloro-2-(2-fluoro-benzenesulfonyl)-benzenesulfonyl]-phenyl}-ethyl)-methanesulfonamide; [6-Iodo-2-methyl-1-(2-morpholin-4-yl-ethyl)-2,3-dihydro-1H-indol-3-yl]-(4-methoxy-phenyl)-methanone; 1-(4-Chloro-phenyl)-2-(2-chloro-phenyl)-5-ethyl-1H-imidazole-4-carboxylic acid piperidin-1-ylamide; (2-Methyl-1-propyl-2,3-dihydro-1H-indol-3-yl)-naphthalen-1-yl-methanone; 5-(1,1-Dimethyl-heptyl)-2-[5-hydroxy-2-(3-hydroxy-propyl)-cyclohexyl]-phenol; (2-Methyl-3-morpholin-4-ylmethyl-3,4-dihydro-5-oxa-2a-azacenaphthylen-1-yl)-naphthalen-1-yl-methanone; 5-(4-Chloro-phenyl)-1-(2,4-dichloro-phenyl)-4-methyl-1H-pyrazole-3-carboxylic acid piperidin-1-ylamide; 5-(4-Bromo-phenyl)-1-(2,4-dichloro-phenyl)-4-ethyl-1H-pyrazole-3-carboxylic acid piperidin-1-ylamide; 1-[Bis-(4-chloro-phenyl)-methyl]-3-[(3,5-difluoro-phenyl)-methanesulfonyl-methylene]-azetidine; 4-Chloro-N-{[3-(4-chloro-phenyl)-4-phenyl-4,5-dihydro-pyrazol-1-yl]-methylamino-methylene}-benzenesulfonamide; N-{Amino-[3-(4-chloro-phenyl)-4-phenyl-4,5-dihydro-pyrazol-1-yl]-methylene}-4-chloro-benzenesulfonamide; N-{[3-(4-Chloro-phenyl)-4-pyridin-3-yl-4,5-dihydro-pyrazol-1-yl]-methylamino-methylene}-4-trifluoromethyl-benzenesulfonamide; 4-Chloro-N-{[3-(4-chloro-phenyl)-4-pyridin-3-yl-4,5-dihydro-pyrazol-1-yl]-methylamino-methylene}-benzenesulfonamide; 4-Chloro-N-{[3-(4-chloro-phenyl)-4-(3-fluoro-phenyl)-4,5-dihydro-pyrazol-1-yl]-methoxyamino-methylene}-benzenesulfonamide; Morpholine-4-sulfonic acid [3-(4-chloro-phenyl)-4-phenyl-4,5-dihydro-pyrazol-1-yl]-methylamino-methyleneamide; N-{[3-(4-Chloro-phenyl)-4-(3-fluoro-phenyl)-4,5-dihydro-pyrazol-1-yl]-methylamino-methylene}-N,N-dimethyl-sulfonamide; Azepane-1-sulfonic acid [3-(4-chloro-phenyl)-4-phenyl-4,5-dihydro-pyrazol-1-yl]-methylamino-methyleneamide; 4-Chloro-N-{[3-(4-chloro-phenyl)-4-phenyl-4,5-dihydro-pyrazol-1-methyl-pyrrolidin-3-ylmethyl)-amino]-methylene}-benzenesulfonamide; 1-(4-Chloro-phenyl)-5-phenyl-4,5-dihydro-1H-pyrazole-3-carboxamidine; N-{[3-(4-Chloro-phenyl)-4-phenyl-4,5-dihydro-pyrazol-1-yl]-methylamino-methylene}-4-trifluoromethyl-benzene-sulfonamide; Piperidine-1-sulfonic acid [3-(4-chloro-phenyl)-4-phenyl-4,5-dihydro-pyrazol-1-yl]-methylamino-methyleneamide; Piperidine-1-sulfonic acid [3-(4-chloro-phenyl)-4-phenyl-4,5-dihydro-pyrazol-1-yl]-(2-dimethylamino-ethylamino)-methyleneamide; N,N-Diethylamino-1-sulfonic acid [3-(4-chloro-phenyl)-4-phenyl-4,5-dihydro-pyrazol-1-yl]-methylsulfanyl-methyleneamide; 2-Amino-1-[3-(4-chloro-phenyl)-4-phenyl-4,5-dihydro-pyrazol-1-yl]-3-(3,4-dichloro-phenyl)-propan-1-one; Morpholine-4-sulfonic acid [3-(4-chloro-phenyl)-4-phenyl-4,5-dihydro-pyrazol-1-yl]-methylamino-methyleneamide; N,N-Dimethylamino-1-sulfonic acid [3-(4-chloro-phenyl)-4-phenyl-4,5-dihydro-pyrazol-1-yl]-(2-fluoro-ethylamino)-methyleneamide; Piperidine-1-sulfonic acid [3-(4-chloro-phenyl)-4-(3-fluoro-phenyl)-4,5-dihydro-pyrazol-1-yl]-methylamino-methyleneamide; 5-(4-Chloro-phenyl)-1-(2,4-dichloro-phenyl)-4,5-dihydro-1H-pyrazole-3-carboxylic acid piperidine-1-ylamide; 1-(4-Chloro-phenyl)-5-phenyl-4,5-dihydro-1H-pyrazole-3-carboxylic acid piperidin-1-ylamide; Piperidine-1-sulfonic acid [1-(4-chloro-phenyl)-5-phenyl-4,5-dihydro-1H-pyrazol-3-yl]-methylamino-methyleneamide; Morpholine-4-sulfonic acid [1-(2,4-dichloro-phenyl)-5-phenyl-4,5-dihydro-1H-pyrazol-3-yl]-methylamino-methyleneamide; 4-Chloro-N-[[3-(4-chloro-phenyl)-4-phenyl-4,5-dihydro-pyrazol-1-yl]-(2-fluoro-ethylamino)-methylene]-benzenesulfonamide; 4-Chloro-N-[[3-(4-chloro-phenyl)-4-phenyl-4,5-dihydro-pyrazol-1-yl]-(2-fluoro-ethylamino)-methylene]-benzenesulfonamide; N-{Amino-[3-(4-chloro-phenyl)-4-phenyl-4,5-dihydro-pyrazol-1-yl]-methylene}-4-chloro-benzenesulfonamide; 4-Chloro-N-[3-(4-chloro-phenyl)-4-phenyl-4,5-dihydro-pyrazole-1-carbonyl]-benzenesulfonamide; 4-Chloro-N-[[3-(4-chloro-phenyl)-4-phenyl-4,5-dihydro-pyrazol-1-yl]-(2-ethylamino-ethylamino)-methylene]-benzenesulfonamide; 4-Chloro-N-{[3-(4-chloro-phenyl)-4-phenyl-4,5-dihydro-pyrazol-1-yl]-[(1-methyl-pyrrolidin-2-ylmethyl)-amino]-methylene}-benzenesulfonamide; 4-Chloro-N-[[3-(4-chloro-phenyl)-4-phenyl-4,5-dihydro-pyrazol-1-yl]-(4-pyrrolidin-1-yl-butylamino)-methylene]benzenesulfonamide; 4-Chloro-N-{[3-(4-chloro-phenyl)-4-phenyl-4,5-dihydro-pyrazol-1-yl]-[(pyridin-3-ylmethyl)-amino]-methylene}-benzenesulfonamide; 1-[3-(4-Chloro-phenyl)-4-phenyl-4,5-dihydro-pyrazol-1-yl]-3-(1H-indol-2-yl)-2-methylamino-propan-1-one; 2-[3-(4-Chloro-phenyl)-4-phenyl-4,5-dihydro-pyrazol-1-yl]-5-ethyl-4,5-dihydro-oxazole; 4-Chloro-N-[[3-(4-chloro-phenyl)-4-phenyl-4,5-dihydro-pyrazol-1-yl]-(3-hydroxy-2,2-dimethyl-propylamino)-methylene]-benzenesulfonamide;

N,N-Diethylamino-1-sulfonic acid [3-(4-chloro-phenyl)-4-hydroxy-4-phenyl-4,5-dihydro-pyrazol-1-yl]-methylamino-methyleneamide; 5-(4-Bromo-phenyl)-1-(2,4-dichloro-phenyl)-1H-pyrazole-3-carbonitrile; 8-Chloro-1-(2,4-dichloro-phenyl)-1,3a,4,5,6,10b-hexahydro-1,2-diaza-benzo[e]azulene-3-carboxylic acid piperidin-1-ylamide; 5-(4-Bromo-phenyl)-1-(2,4-dichloro-phenyl)-3-[2-(3,5-difluoro-phenyl)-2-methanesulfonyl-vinyl]-4-methyl-1H-pyrazole; Piperidine-1-carboxylic acid [5-(4-chloro-phenyl)-1-(2,4-dichloro-phenyl)-4-methyl-1H-pyrazol-3-yl]amide; 1-(4-Chloro-phenyl)-2-(2,4-dichloro-phenyl)-5-ethylsulfanyl-1H-imidazole-4-carboxylic acid piperidin-1-ylamide; Dichloro-phenyl)-1-(4-trifluoromethyl-phenyl)-1H-imidazole-4-carboxylic acid piperidin-1-ylamide; 1-(4-Chloro-phenyl)-2-(2,4-dichloro-phenyl)-5-methylsulfanyl-1H-imidazole-4-carboxylic acid piperidin-1-ylamide; 1-(4-Chloro-phenyl)-2-(2,4-dichloro-phenyl)-1H-imidazole-4-carboxylic acid piperidin-1-ylamide; 1-(4-Chloro-phenyl)-2-(2,4-dichloro-phenyl)-5-ethyl-1H-imidazole-4-carboxylic acid piperidin-1-ylamide; 1-(4-Bromo-phenyl)-2-(2,4-dichloro-phenyl)-5-ethyl-1H-imidazole-4-carboxylic acid piperidin-1-ylamide; 1-(4-Bromo-phenyl)-5-chloro-2-(2,4-dichloro-phenyl)-1H-imidazole-4-carboxylic acid piperidin-1-ylamide; 1-(4-Bromo-phenyl)-2-(2,4-dichloro-phenyl)-5-ethyl-1H-imidazole-4-carboxylic acid cyclohexylamide; 1-(4-Bromo-phenyl)-2-(2,4-dichloro-phenyl)-5-ethyl-1H-imidazole-4-carboxylic acid pentylamide; 4-(4-Chloro-phenyl)-5-(2,4-dichloro-phenyl)-1-methyl-1H-imidazole-2-carboxylic acid cyclohexylamide; 4-(4-Chloro-phenyl)-5-(2,4-dichloro-phenyl)-3-methyl-1H-imidazole-2-carboxylic acid cyclohexylamide; 1-(5-Chloro-pyridin-2-yl)-2-(2,4-dichloro-phenyl)-5-ethyl-1H-imidazole-4-carboxylic acid piperidin-1-ylamide; 1-(4-Chloro-phenyl)-2-(2,4-dichloro-phenyl)-5-methyl-1H-imidazole-4-carboxylic acid (4-hydroxy-cyclo-hexyl)-amide; 1-(4-Chloro-phenyl)-2-(2,4-dichloro-phenyl)-5-methyl-1H-imidazole-4-carboxylic acid azepan-1-ylamide; 2-(2,4-Dichloro-phenyl)-5-ethyl-1-phenyl-1H-imidazole-4-carboxylic acid piperidin-1-ylamide; 2-(1,5-Dimethyl-1H-pyrrol-2-yl)-5-ethyl-1-phenyl-1H-imidazole-4-carboxylic acid cyclohexylamide; 1-(4-Chloro-phenyl)-5-ethyl-2-(3-methyl-pyridin-2-yl)-1H-imidazole-4-carboxylic acid piperidin-1-ylamide; 1-(4-Chloro-phenyl)-2-(2,4-dichloro-phenyl)-5-ethyl-1H-imidazole-4-carboxylic acid piperidin-1-ylamide; 1-(4-Bromo-phenyl)-2-(2,4-dichloro-phenyl)-5-ethyl-1H-imidazole-4-carboxylic acid piperidin-1-ylamide; 1-(4-Bromo-phenyl)-5-chloro-2-(2,4-dichloro-phenyl)-1H-imidazole-4-carboxylic acid piperidin-1-ylamide; 1-(4-Bromo-phenyl)-2-(2,4-dichloro-phenyl)-5-ethyl-1H-imidazole-4-carboxylic acid cyclohexylamide; 1-(4-Bromo-phenyl)-2-(2,4-dichloro-phenyl)-5-ethyl-1H-imidazole-4-carboxylic acid pentylamide; 4-(4-Chloro-phenyl)-5-(2,4-dichloro-phenyl)-1-methyl-1H-imidazole-2-carboxylic acid cyclohexylamide; 4-(4-Chloro-phenyl)-5-(2,4-dichloro-phenyl)-3-methyl-1H-imidazole-2-carboxylic acid cyclohexylamide; 1-(5-Chloro-pyridin-2-yl)-2-(2,4-dichloro-phenyl)-5-ethyl-1H-imidazole-4-carboxylic acid piperidin-1-ylamide; 1-(4-Chloro-phenyl)-2-(2,4-dichloro-phenyl)-5-methyl-1H-imidazole-4-carboxylic acid (4-hydroxy-cyclo-hexyl)-amide; 1-(4-Chloro-phenyl)-2-(2,4-dichloro-phenyl)-5-methyl-1H-imidazole-4-carboxylic acid azepan-1-ylamide; 2-(2,4-Dichloro-phenyl)-5-ethyl-1-phenyl-1H-imidazole-4-carboxylic acid piperidin-1-ylamide; 2-(1,5-Dimethyl-1H-pyrrol-2-yl)-5-ethyl-1-phenyl-1H-imidazole-4-carboxylic acid cyclohexylamide; 1-(4-Chloro-phenyl)-5-ethyl-2-(3-methyl-pyridin-2-yl)-1H-imidazole-4-carboxylic acid cyclohexylamide; 1-(4-Chloro-phenyl)-2-(2,4-dichloro-phenyl)-5-methyl-1H-imidazole-4-carboxylic acid (4-trifluoromethyl-phenyl)-amide; 2-(2,4-Dichloro-phenyl)-5-methyl-1-pyridin-2-yl-1H-imidazole-4-carboxylic acid piperidin-1-ylamide; 1-(4-Chloro-phenyl)-2-(2,4-dichloro-phenyl)-5-fluoromethyl-1H-imidazole-4-carboxylic acid piperidin-1-ylamide; 1-(4-Chloro-phenyl)-2-(2,4-dichloro-phenyl)-5-hydroxymethyl-1H-imidazole-4-carboxylic acid piperidin-1-ylamide; 1-(4-Chloro-phenyl)-2-(2,4-dichloro-phenyl)-5-methylsulfanyl-1H-imidazole-4-carboxylic acid cyclohexylamide; 1-(4-Chloro-phenyl)-2-(2,4-dichloro-phenyl)-5-methanesulfonyl-1H-imidazole-4-carboxylic acid piperidin-1-ylamide; 1-(4-Chloro-phenyl)-2-(2,4-dichloro-phenyl)-5-methanesulfinyl-1H-imidazole-4-carboxylic acid piperidin-1-ylamide; 5-(4-Chloro-phenyl)-4-(2,5-dichloro-phenyl)-1-methyl-1H-imidazole-2-carboxylic acid piperidin-1-ylamide; 2-(2-Chloro-phenyl)-1-(5-chloro-pyridin-2-yl)-5-ethyl-1H-imidazole-4-carboxylic acid piperidin-1-ylamide; 1-(4-Chloro-phenyl)-2-(2,4-dichloro-phenyl)-5-(2,2,2-trifluoro-ethyl)-1H-imidazole-4-carboxylic acid piperidin-1-ylamide; N-[1-(4-Chloro-phenyl)-2-(2,4-dichloro-phenyl)-5-methyl-1H-imidazol-4-yl]-benzamide; 1-(4-Chloro-phenyl)-2-(2,4-dichloro-phenyl)-5-pyrrolidin-1-ylmethyl-1H-imidazole-4-carboxylic acid piperidin-1-ylamide; 2-[1-(4-Chloro-phenyl)-2-(2,4-dichloro-phenyl)-5-methyl-1H-imidazol-4-yl]-hexan-2-ol; 1-(4-Chloro-phenyl)-2-(2,4-dichloro-phenyl)-5-methyl-4-pentyl-1H-imidazole; 2,5-Dimethyl-1-phenyl-1H-imidazole-4-carboxylic acid adamantan-2-ylamide; 1-(4-Chloro-phenyl)-2-(2-chloro-phenyl)-5-methylsulfanyl-1H-imidazole-4-carboxylic acid piperidin-1-ylamide; 2-(2-Chloro-phenyl)-1-(4-trifluoromethyl-phenyl)-1H-imidazole-4-carboxylic acid piperidin-1-ylamide; 5-(4-Chloro-phenyl)-4-(2,4-dichloro-phenyl)-thiazole-2-carboxylic acid piperidin-1-ylamide; 5-(4-Chloro-phenyl)-1-(2,4-dichloro-phenyl)-1H-[1,2,4]triazole-3-carboxylic acid pyrrolidin-1-ylamide; 1-(4-Chloro-phenyl)-5-(2,4-dichloro-phenyl)-1H-[1,2,4]triazole-3-carboxylic acid piperidin-1-yl-amide; 5-Pentyl-4-phenyl-thiazole-2-carboxylic acid (hexahydro-2,5-methano-pentalen-3a-yl)-amide; 4-Pentyl-5-phenyl-thiazole-2-carboxylic acid (hexahydro-2,5-methano-pentalen-3a-yl)-amide; 1-{(4-Chloro-benzene-sulfonylimino)-[3-(4-chloro-phenyl)-4-phenyl-4,5-dihydro-pyrazol-1-yl]-methyl}-piperidine-4-carboxylic acid amide; 4-Chloro-N-{[3-(4-chloro-phenyl)-4-phenyl-4,5-dihydro-pyrazol-1-yl]-[2-(2-oxo-pyrrolidin-1-yl)-ethylamino]-methylene}-benzenesulfonamide; 4-Chloro-N-[[3-(4-chloro-phenyl)-4-phenyl-4,5-dihydro-pyrazol-1-yl]-(2-cyano-ethylamino)-methylene]-benzenesulfonamide; 4-Chloro-N-[[3-(4-chloro-phenyl)-4-phenyl-4,5-dihydro-pyrazol-1-yl]-(methoxy-methyl-amino)-methylene]-benzenesulfonamide; 4-Chloro-N-{[(4-chloro-phenyl)-4-phenyl-4,5-dihydro-pyrazol-1-yl]-[(piperidin-4-ylmethyl)-amino]-methylene}-benzenesulfonamide; 4-Chloro-N-[[3-(4-chloro-phenyl)-4-phenyl-4,5-dihydro-pyrazol-1-yl]-(piperidin-4-ylamino)-methylene]-benzenesulfonamide; and Morpholine-4-sulfonic acid [3-(4-chloro-phenyl)-4-phenyl-4,5-dihydro-pyrazol-1-yl]-(cyclopropylmethyl-amino)-methyleneamide.

In another embodiment, the $CB_x$ modulators suitable as a $K_{ATP}$ channel modulator are selected from the group consisting of: 3-(1,1-dimethyl-butyl)-6,6,9-trimethyl-6a,7,10,10a-tetrahydro-6H-benzo[c]chromene; N-Adamantyl-4-pentyl-5-phenyl-thiazole-2-carboxamide; N-{1,3,3-Trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide; (2-Iodo-5-nitro-phenyl)-[1-(1-methylpiperidin-2-ylmethyl)-1H-indol-3-yl]-methanone; {4-[4-(1,1-Dimethyl-heptyl)-2,6-dimethoxy-phenyl]-6,6-dimethyl-bicyclo[3.1.1]hept-2-en-2-yl}-methanol; 3-(1,1-Dimethyl-heptyl)-9-hydroxymethyl-6,6,6-dimethyl-6a,7,10,10a-tetrahydro-6H-enzo[c]chromen-1-ol; Icosa-5,8,11,14-tetraenoic acid 2-hydroxy-1-hydroxymethyl-ethyl ester; 1-Aziridin-1-yl-henicosa-6,9,12,15-tetraen-2-one; Noladineether; 4,4,4-Trifluoro-butane-1-sulfinic acid 3-(2-hydroxymethyl-indan-4-yloxy)-phenyl ester, compound with form aldehyde; 7-Methoxy-2-oxo-8-pentyloxy-1,2-dihydro-quinoline-3-carboxylic acid (benzo[1,3]dioxol-5-yl-methyl)-amide; N-(1-{-4-[4-Chloro-2-(2-fluoro-benzene-sulfonyl)-benzenesulfonyl]-phenyl}-ethyl)-methanesulfonamide; [6-Iodo-2-methyl-1-(2-morpholin-4-yl-ethyl)-2,3-dihydro-1H-indol-3-yl]-(4-methoxy-phenyl)-methanone; 1-(4-Chloro-phenyl)-2-(2-chloro-phenyl)-5-ethyl-1H-imidazole-4-carboxylic acid piperidin-1-ylamide; (2-Methyl-1-propyl-2,3-dihydro-1H-indol-3-yl)-naphthalen-1-yl-methanone; 5-(1,1-Dimethyl-heptyl)-2-[5-hydroxy-2-(3-hydroxy-propyl)-cyclohexyl]-phenol; (2-Methyl-3-morpholin-4-ylmethyl-3,4-dihydro-5-oxa-2a-azacenaphthylen-1-yl)-naphthalen-1-yl-methanone; 5-(4-Chloro-phenyl)-1-(2,4-dichloro-phenyl)-4-methyl-1H-pyrazole-3-carboxylic acid piperidin-1-ylamide; 5-(4-Bromo-phenyl)-1-(2,4-dichloro-phenyl)-4-ethyl-1H-pyrazole-3-carboxylic acid piperidin-1-ylamide; 1-[Bis-(4-chloro-phenyl)-methyl]-3-[(3,5-difluoro-phenyl)-methanesulfonyl-methylene]-azetidine.

In another embodiment, the $CB_x$ modulators suitable as a $K_{ATP}$ channel modulator are selected from the group consisting of: 4-Chloro-N-{[3-(4-chloro-phenyl)-4-phenyl-4,5-dihydro-pyrazol-1-yl]-methylamino-methylene}-benzenesulfonamide; N-{Amino-[3-(4-chloro-phenyl)-4-phenyl-4,5-dihydro-pyrazol-1-yl]-methylene}-4-chloro-benzenesulfonamide; 4-Chloro-N-{[3-(4-chloro-phenyl)-4-pyridin-3-yl-4,5-dihydro-pyrazol-1-yl]-methylamino-methylene}-benzenesulfonamide; 4-Chloro-N-{[3-(4-chloro-phenyl)-4-(3-fluoro-phenyl)-4,5-dihydro-pyrazol-1-yl]-methoxyamino-methylene)-benzenesulfonamide; N-{[3-(4-Chloro-phenyl)-4-(3-fluoro-phenyl)-4,5-dihydro-pyrazol-1-yl]-methylamino-methylene}-N,N-dimethyl-sulfonamide; 5-(4-Chloro-phenyl)-1-(2,4-dichloro-phenyl)-4,5-dihydro-1H-pyrazole-3-carboxylic acid piperidine-1-ylamide; Morpholine-4-sulfonic acid [1-(2,4-dichloro-phenyl)-5-phenyl-4,5-dihydro-1H-pyrazol-3-yl]-methylamino-methyleneamide; N-{Amino-[3-(4-chloro-phenyl)-4-phenyl-4,5-dihydro-pyrazol-1-yl]-methylene}-4-chloro-benzenesulfonamide; 4-Chloro-N-[[3-(4-chloro-phenyl)-4-phenyl-4,5-dihydro-pyrazol-1-yl]-(2-ethylamino-ethylamino)-methylene]-benzenesulfonamide; 4-Chloro-N-{[3-(4-chloro-phenyl)-4-phenyl-4,5-dihydro-pyrazol-1-yl]-[(1-methyl-pyrrolidin-2-ylmethyl)-amino]-methylene}-benzenesulfonamide; 4-Chloro-N-{[3-(4-chloro-phenyl)-4-phenyl-4,5-dihydro-pyrazol-1-yl]-[(pyridin-3-ylmethyl)-amino]-methylene}-benzenesulfonamide; 1-(4-Chloro-phenyl)-2-(2,4-dichloro-phenyl)-5-ethylsulfanyl-1H-imidazole-4-carboxylic acid piperidin-1-ylamide; 2-(2,4-Dichloro-phenyl)-1-(4-trifluoromethyl-phenyl)-1H-imidazole-4-carboxylic acid piperidin-1-ylamide; 1-(4-Chloro-phenyl)-2-(2,4-dichloro-phenyl)-5-methylsulfanyl-1H-imidazole-4-carboxylic acid piperidin-1-ylamide; 1-(4-Chloro-phenyl)-2-(2,4-dichloro-phenyl)-5-ethyl-1H-imidazole-4-carboxylic acid piperidin-1-ylamide; 1-(4-Bromo-phenyl)-2-(2,4-dichloro-phenyl)-5-ethyl-1H-imidazole-4-carboxylic acid piperidin-1-ylamide; 1-(4-Bromo-phenyl)-5-chloro-2-(2,4-dichloro-phenyl)-1H-imidazole-4-carboxylic acid piperidin-1-ylamide; 1-(4-Bromo-phenyl)-2-(2,4-dichloro-phenyl)-5-ethyl-1H-imidazole-4-carboxylic acid pentylamide; 1-(4-Chloro-phenyl)-2-(2,4-dichloro-phenyl)-5-methyl-1H-imidazole-4-carboxylic acid azepan-1-ylamide; 1-(4-Chloro-phenyl)-2-(2,4-dichloro-phenyl)-5-fluoromethyl-1H-imidazole-4-carboxylic acid piperidin-1-ylamide; 1-(4-Chloro-phenyl)-2-(2,4-dichloro-phenyl)-5-methylsulfanyl-1H-imidazole-4-carboxylic acid cyclohexylamide; N-[1-(4-Chloro-phenyl)-2-(2,4-dichloro-phenyl)-5-methyl-1H-imidazol-4-yl]-benzamide; 2-[1-(4-Chloro-phenyl)-2-(2,4-dichloro-phenyl)-5-methyl-1H-imidazol-4-yl]-hexan-2-ol; 1-(4-Chloro-phenyl)-2-(2,4-dichloro-phenyl)-5-methyl-4-pentyl-1H-imidazole; 1-(4-Chloro-phenyl)-2-(2-chloro-phenyl)-5-methylsulfanyl-1H-imidazole-4-carboxylic acid piperidin-1-ylamide; 2-(2-Chloro-phenyl)-1-(4-trifluoromethyl-phenyl)-1H-imidazole-4-carboxylic acid piperidin-1-ylamide; 5-(4-Chloro-phenyl)-4-(2,4-dichloro-phenyl)-thiazole-2-carboxylic acid piperidin-1-ylamide; 1-(4-Chloro-phenyl)-5-(2,4-dichloro-phenyl)-1H-[1,2,4]triazole-3-carboxylic acid piperidin-1-yl-amide; 1-{(4-Chloro-benzene-sulfonylimino)-[3-(4-chloro-phenyl)-4-phenyl-4,5-dihydro-pyrazol-1-yl]-methyl}-piperidine-4-carboxylic acid amide; 4-Chloro-N-{[3-(4-chloro-phenyl)-4-phenyl-4,5-dihydro-pyrazol-1-yl]-[2-(2-oxo-pyrrolidin-1-yl)-ethylamino]-methylene}-benzenesulfonamide; 4-Chloro-N-[[3-(4-chloro-phenyl)-4-phenyl-4,5-dihydro-pyrazol-1-yl]-(2-cyano-ethylamino)-methylene]-benzene-sulfonamide; 4-Chloro-N-[[3-(4-chloro-phenyl)-4-phenyl-4,5-dihydro-pyrazol-1-yl]-(methoxy-methyl-amino)-methylene]-benzenesulfonamide; Morpholine-4-sulfonic acid [3-(4-chloro-phenyl)-4-phenyl-4,5-dihydro-pyrazol-1-yl]-(cyclopropyl methyl-amino)-methyleneamide.

In another embodiment, the $K_{ATP}$ channel modulator also functions as a $CB_x$ modulator; or the $CB_x$ modulator also functions as a $K_{ATP}$ channel modulator; provided that the $K_{ATP}$ channel modulator and the $CB_x$ modulator are different compounds.

In another embodiment, the $K_{ATP}$ channel modulator and the $CB_x$ modulator are administered simultaneously in the same or different dosage form or sequentially in the same or different dosage form. In a further embodiment, the $K_{ATP}$ channel modulator and the $CB_x$ modulator are administered simultaneously in an oral dosage form.

Description of the Pharmacological Test Methods

1. In Vitro Binding Affinity of the Test Compounds to Rodent $K_{ATP}$ Channels

Competitive binding experiments were performed to characterize the affinity of the test compounds for the binding sites for sulfonylureas and $K_{ATP}$ channel openers (KCOs) on hamster SUR1. To assess the affinity for the sulfonylurea site membranes from COS-cells transiently expressing hamster SUR1 were incubated in the presence of [$^3$H]glibenclamide with increasing concentrations of test compounds. The affinity for binding to the KCO site was assessed by incubations in the additional presence of 100 μM MgATP (see Schwanstecher M., et al. Naunyn-Schmiedeberg's Arch. Pharmacol. 343 (1991) 83-89 and Schwanstecher M. et al., EMBO J. 17 (1998) 5529-5535 (Schwanstecher et al., 1998)). For each test compound 4 displacement curves were measured (+/− MgATP from the human and hamster isoform). Per curve 9-15 distinct concentrations were tested covering the relevant range. All measurements were repeated at least 5 times in independent experiments.

Similar to SUR1 (see above) competitive binding experiments were performed to characterize the affinity of the test compounds for the binding sites for sulfonylureas and KCOs on rat SUR2A. The affinity for the KCO site on SUR2A was assessed by displacement of [³H]P1075 (see Schwanstecher et al., 1998; Dörschner H. et al. Mol. Pharmacol. 55 (1999) 1060-1066 (Dörschner et al., 1999)). The affinity of [³H] glibenclamide for the human SUR2 isoforms, however, is too weak to allow direct detection of binding using filtration assays. Therefore, two strategies can be used to detect binding to the sulfonylurea site on SUR2A. First, binding can be detected indirectly through allosteric displacement of [³H] P1075 (Dörschner et al., 1999). Second, a mutated SUR2A (SUR2A$_{Y1205S}$, see above) with increased affinity for [³H] glibenclamide allowing direct displacement of this tracer can be used. This second approach was chosen to enable discrimination between allosteric and competitive interaction with the KCO site and to make certain that the binding of ligands which do not induce allosteric displacement are not overlooked.

Membranes from COS-cells transiently expressing rat SUR2A were incubated in the presence of the radioligands with increasing concentrations of test compounds as described above. The affinity for binding to the KCO site was assessed by incubations in the additional presence of 100 µM MgATP (Schwanstecher et al., 1991 and 1998). For each test compound 4 displacement curves were measured (displacement of [³H]P1075 from the rat isoform of the wild type receptor and displacement of [³H]glibenclamide from the rat isoform of SUR2A$_{Y1205S}$). Per curve 9-15 distinct concentrations were tested covering the relevant range. All measurements were repeated at least 5 times in independent experiments.

[³H]P1075 (specific activity 116 Ci mmol$^{-1}$) was purchased from Amersham Buchler (Braunschweig, Germany). [³H]glibenclamide (specific activity 51 Ci mmol$^{-1}$ was obtained from NEN (Dreieich, Germany). If suitable, stock solutions were prepared in dimethylsulfoxide with a final solvent concentration in the media below 1%.

SUR- or Kir6.x isoforms were used either subcloned in the pcDNA (hamster SUR1, mouse Kir6.2) or pCMV vector (rat SUR2A, SUR2B).

Rodent SUR-isoforms and K$_{ATP}$ channels were transiently expressed in COS-1 cells as described in the literature. See, Schwanstecher et al., 1998; Dörschner et al., 1999; Uhde I. et al. J Biol Chem 274 (1999) 28079-28082; Gross I. et al. Mol. Pharmacol. 56 (1999) 1370-1373; Markworth E., Diabetes 49 (2000) 1413-1418). A mutated form of the SUR2 isoforms with the phenylalanine residue in position 1205 substituted with a serine (SUR2$_{Y1205S}$) was used to allow detection of binding to the sulfonylurea site of these isoforms by displacement of [³H]glibenclamide (Uhde I., Dissertation 2001). Briefly, COS-1 cells cultured in DMEM HG (10 mM glucose), supplemented with 10% fetal calf serum (FCS), were plated at a density of 5×10⁵ cells per dish (94 mm) and allowed to attach overnight. For transfection, the cells were incubated 4 hours in a Tris-buffered salt solution containing DNA (5-10 µg/ml) plus DEAE-dextran (1 mg/ml), 2 min in HEPES-buffered salt solution plus dimethylsulfoxide (10%) and 4 hours in DMEM-HG plus chloroquine (100 µM). Cells were then returned to DMEM-HG plus 10% FCS. Membranes were prepared 60-72 h post transfection as described in Schwanstecher M. et al., Br. J. Pharmacol. 106 (1992) 295-301. For binding experiments resuspended membranes (final protein concentration 5-50 µg/ml) were incubated in "Tris-buffer" (50 mM, pH 7.4) containing either [³H]glibenclamide (final concentration 0.3 nM or 3 nM and nonspecific binding defined by 100 nM or 1 µM glibenclamide for SUR1 or SUR2$_{Y1205S}$-isoforms, respectively) or [³H]P1075 (final concentration 3 nM, nonspecific binding defined by 100 µM pinacidil) and increasing concentrations of the test compounds. The free Mg$^{2+}$ concentration were kept close to 0.7 mM. ATP (0.1 mM) was added to the incubation media to enable KCO (e.g. diazoxide, [³H]P1075) binding (see Schwanstecher et al., 1998). Incubations were carried out for 1 h at room temperature and were terminated by rapid filtration through Whatman GF/B filters.

Similar to SUR2A (see above) competitive binding experiments were performed to characterize the affinity of the test compounds for the sulfonylureas and KCOs binding sites on rat SUR2b. The binding protocol for SUR2B is identical with the binding protocol for SUR2A with the exception that cDNA encoding the isoform SUR2B is used for transient expression in COS cells instead of cDNA encoding SUR2A. Ligands and conditions are the same as for SUR2A.

The inhibition constant (K$_i$ value) of the test substances was calculated from the respective IC$_{50}$ value and was stated as the negative logarithmic value thereof (pK$_i$).

The binding affinity and selectivity of a given compound towards SUR1 and SUR2 can be used as criteria to reflect the modulation of the K-ATP channel (e.g. NN-414, with a pKi 6.2, is more than 100 times more potent than diazoxide, having a pKi of 3.8, to inhibit glucose-stimulated insulin release). The binding data can be used as first estimate of the potential of a given compound to preserve beta cell function and to prevent or delay the progression of diabetes.

Compounds having a pK$_i$ (SUR1) larger than pK$_i$ (SUR2) are preferred. These compounds include but are not limited to: (4S)-3-(4-chlorophenyl)-N'-[(4-chlorophenyl)sulfonyl]-N-methyl-4-phenyl-4,5-dihydro-1H-pyrazole-1-carboximid-amide; 5-(1,1-dimethylheptyl)-2-[(1R,2R,5R)-5-hydroxy-2-(3-hydroxypropyl)cyclohexyl]-phenol; (2S)-1-[3-(4-chlorophenyl)-4-phenyl-4,5-dihydro-1H-pyrazol-1-yl]-3-(3,4-dichloro-phenyl)-1-oxopropan-2-amine; 3-(4-chlorophenyl)-N'-[(4-chlorophenyl)sulfonyl]-4-phenyl-N-(pyridin-3-ylmethyl)-4,5-dihydro-1H-pyrazole-1-carboximidamide; (2S)-1-[3-(4-chloro-phenyl)-4-phenyl-4,5-dihydro-1H-pyrazol-1-yl]-3-(1H-indol-3-yl)-N-methyl-1-oxopropan-2-amine; 2-[3-(4-chlorophenyl)-4-phenyl-4,5-dihydro-1H-pyrazol-1-yl]-5-ethyl-4,5-dihydro-1,3-oxazole; 3-(4-chlorophenyl)-N'-[(4-chlorophenyl)sulfonyl]-N-[(1-methylpyrrolidin-3-yl)-methyl]-4-phenyl-4,5-dihydro-1H-pyrazole-1-carboximidamide; 5-(4-bromophenyl)-N-[(4-chlorophenyl)sulfonyl]-1-(2,4-dichlorophenyl)-1H-pyrazole-3-carboxamide; 8-chloro-1-(2,4-dichlorophenyl)-N-piperidin-1-yl-1,4,5,6-tetrahydrobenzo[6,7]cyclohepta[1,2-c]pyrazole-3-carboxamide; 1-[bis(4-chlorophenyl) methyl]-3-[(3,5-difluorophenyl)(methylsulfonyl)-methylene]azetidine; 2-{1-[bis(4-chlorophenyl)methyl] azetidin-3-yl}-1,2-benzisothiazol-3(2H)-one 1,1-dioxide; 1-(4-bromophenyl)-2-(2,4-dichlorophenyl)-5-ethyl-N-pentyl-1H-imidazole-4-carboxamide; 3-(4-chlorophenyl)-N'-[(dimethylamino)sulfonyl]-N-(2-fluoro-ethyl)-4-phenyl-4,5-dihydro-1H-pyrazole-1-carboximidamide; 3-(4-chlorophenyl)-N-methyl-N'-(morpholin-4-ylsulfonyl)-4-phenyl-4,5-dihydro-1H-pyrazole-1-carboximidamide; 1-(4-chlorophenyl)-2-(2,4-dichlorophenyl)-N,N-diethyl-1H-imidazole-4-carboxamide; 3-(4-chlorophenyl)-N'-[(4-chlorophenyl)sulfonyl]-N-methyl-4-pyridin-3-yl-4,5-dihydro-1H-pyrazole-1-carboximidamide; 1-(4-chlorophenyl)-N-methyl-5-phenyl-N'-(piperidin-1-yl-sulfonyl)-4,5-dihydro-1H-pyrazole-3-carboximidamide; 1-(4-bromophenyl)-2-(2,4-dichloro-phenyl)-5-ethyl-N-piperidin-1-yl-1H-imidazole-4-carboxamide; 1-(2,4-dichlorophenyl)-N-methyl-N'-(morpholin-4-ylsulfonyl)-5-phenyl-4,5-dihydro-1H-pyrazole-3-carboximidamide; 1-(4-chlorophenyl)-N-cyclohexyl-2-(2,4-dichlorophenyl)-5-(methylthio)-1H-imidazole-4-carboxamide; 3-(4- chlorophenyl)-N-methyl-4-pyridin-3-yl-N'-{[4-(trifluoromethyl)phenyl]-sulfonyl}-4,5-dihydro-1H-pyrazole-1-carboximidamide; N-[1-(4-chlorophenyl)-2-(2,4-di-chlorophenyl)-5-methyl-1H-imidazol-4-yl]benzamide; 3-(4-chlorophenyl)-N'-[(dimethyl-amino)sulfonyl]-4-(3-fluorophenyl)-N-methyl-4,5-dihydro-1H-pyrazole-1-carboximidamide; 2-[1-(4-chlorophenyl)-2-(2,4-dichlorophenyl)-5-methyl-1H-imidazol-4-yl]hexan-2-ol; 1-(4-chlorophenyl)-2-(2,4-dichlorophenyl)-5-methyl-4-pentyl-1H-imidazole; 3-(4-chlorophenyl)-N'-[(4-chlorophenyl)sulfonyl]-4-phenyl-4,5-dihydro-1H-pyrazole-1-carboximidamide; (4S)-3-(4-chlorophenyl)-N'-[(4-chlorophenyl)sulfonyl]-4-phenyl-4,5-dihydro-1H-pyrazole-1-carboximidamide; and mixtures of any of the above compounds.

2. In Vitro Binding Affinity of the Test Compounds to $CB_1$ Receptors

The affinity of a compound for cannabinoid $CB_1$ receptors can be determined using membrane preparations of Chinese hamster ovary (CHO) cells in which the human cannabinoid $CB_1$ receptor is stably transfected in conjunction with [$^3$H] CP-55,940 as a radioligand. After incubation of a freshly prepared cell membrane preparation with the [$^3$H]-ligand, with or without a compound whose affinity is to be determined, separation of bound and free ligand is performed by filtration over glass-fiber filters. Radioactivity on the filter is measured by liquid scintillation counting.

3. In Vitro Binding Affinity to $CB_2$ Receptors of the Test Compounds

The affinity of a compound for cannabinoid $CB_2$ receptors can be determined using membrane preparations of Chinese hamster ovary (CHO) cells in which the human cannabinoid $CB_2$ receptor is stably transfected in conjunction with [$^3$H] CP-55,940 as a radioligand. After incubation of a freshly prepared cell membrane preparation with the [$^3$H]-ligand, with or without a compound whose affinity is to be determined, separation of bound and free ligand is performed by filtration over glass-fiber filters. Radioactivity on the filter is measured by liquid scintillation counting.

In vivo and in vitro pharmacological assays related to cannabinoid $CB_{1/2}$ receptor neurotransmission have been disclosed, for example in:

Cannabinoid receptors, Ed. R. G. Pertwee, Academic Press, San Diego, 1995, ISBN 0-12-551460-3
Grotenhermen, F. (2004) J. Cannabis Therapeutics 4(1), 29-77.

In vivo and in vitro pharmacological assays related to cannabinoid $CB_2$ receptor neurotransmission have been disclosed, for example in:

Ibrahim, M. M. et al. (2003) Proc. Natl. Acad. Sci. USA 100, 10529-10533
Hanes, L. et al. (1999) Proc. Natl. Acad. Sci. USA 96, 14228-14233
Zhang, J. et al. (2003) Eur. J. Neuroscience 17, 2750-2754.
Klein, T. W. et al. (2003) J. Leukoc. Biol. 74, 486-496
Shoemaker, J. L. et al. (2005), J. Pharmacol. Exp. Ther. 315, 828-838
Iwamura, H. et al. (2001), J. Pharmacol. Exp. Ther. 296, 420-425.

Table 1-$CB_x$ modulators with their affinities for the CB1 and/or CB2 receptor affinities, (cloned human cannabinoid (CB1 and CB2 respectively) receptors expressed in CHO cells according to the procedures described hereinabove), expressed as $pK_i$ values.

TABLE 1

$CB_x$ modulators with their affinities for the CB1 and/or CB2 receptor affinities, (cloned human cannabinoid (CB1 and CB2 respectively) receptors expressed in CHO cells according to the procedures described hereinabove), expressed as $pK_i$ values.

| compound/name | chemical name | Affinity to | | | |
| --- | --- | --- | --- | --- | --- |
| | | CB1 | CB2 | SUR 1 | SUR 2 |
| (structure) | 3-(1,1-dimethyl-butyl)-6,6,9-trimethyl-6a,7,10,10a-tetrahydro-6H-benzo[c]chromene (JW133) | 6.7 | 7.8 | 5.9 | 3.6 |
| (structure) | N-Adamantyl-4-pentyl-5-phenyl-thiazole-2-carboxamide | 7.8 | 8.1 | 4.0 | 4.0 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | Affinity to | | | |
|---|---|---|---|---|---|
| | | CB1 | CB2 | SUR 1 | SUR 2 |
| (structure) Chiral | N-{1,3,3-Trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide (SR144528) | 6.2 | 7.7 | 6.9 | 4.8 |
| (structure) | (2-Iodo-5-nitro-phenyl)-[1-(1-methyl-piperidin-2-ylmethyl)-1H-indol-3-yl]-methanone (AM-1241) | 6.6 | 7.8 | 5.4 | 4.7 |
| (structure) | {4-[4-(1,1-Dimethyl-heptyl)-2,6-dimethoxy-phenyl]-6,6-dimethyl-bicyclo[3.1.1]hept-2-en-2-yl}-methanol (HU308) | 6.0 | 7.8 | 6.4 | 3.6 |
| (structure) | 3-(1,1-Dimethyl-heptyl)-9-hydroxymethyl-6,6-dimethyl-6a,7,10,10a-tetra-hydro-6H-enzo[c]chromen-1-ol (HU-210) | 7.3 | n/a | 6.1 | 5.1 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | Affinity to | | | |
|---|---|---|---|---|---|
| | | CB1 | CB2 | SUR 1 | SUR 2 |
| (structure) | Icosa-5,8,11,14-tetraenoic acid 2-hydroxy-1-hydroxymethyl-ethyl ester (2-AG) | 6.0 | 5.4 | 5.6 | 5.5 |
| (structure) | 1-Aziridin-1-yl-henicosa-6,9,12,15-tetraen-2-one (ACPA) | 7.7 | 7.1 | 3.9 | 4.7 |
| (structure) | Noladineether | 6.9 | 6.6 | 5.4 | 4.4 |
| (structure) | 4,4,4-Trifluoro-butane-1-sulfinic acid 3-(2-hydroxymethyl-indan-4-yloxy)-phenyl ester; compound with form aldehyde (BAY-38-7271) | 8.0 | 7.3 | 6.0 | 5.2 |
| (structure) | 7-Methoxy-2-oxo-8-pentyloxy-1,2-dihydro-quinoline-3-carboxylic acid (benzo[1,3]dioxol-5-ylmethyl)-amide (JTE-907) | 6.0 | 6.9 | 6.1 | 5.9 |
| (structure) | N-(1-{4-[4-Chloro-2-(2-fluoro-benzenesulfonyl)-benzenesulfonyl]-phenyl}-ethyl)-methanesulfonamide (Schering) | 6.0 | 9.3 | 5.9 | 4.7 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | Affinity to | | | |
|---|---|---|---|---|---|
| | | CB1 | CB2 | SUR 1 | SUR 2 |
| 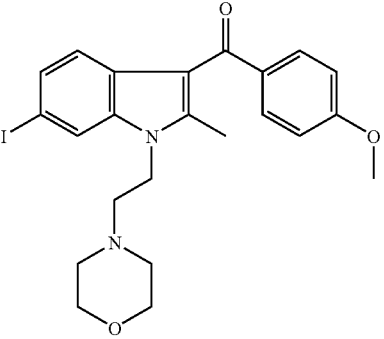 | [6-Iodo-2-methyl-1-(2-morpholin-4-yl-ethyl)-2,3-dihydro-1H-indol-3-yl]-(4-methoxy-phenyl)-methanone (AM-630) | 6.7 | 7.6 | 5.9 | 5.0 |
| 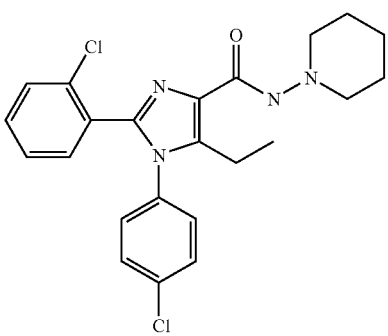 | 1-(4-Chloro-phenyl)-2-(2-chloro-phenyl)-5-ethyl-1H-imidazole-4-carboxylic acid piperidin-1-ylamide (Bayer) | 7.9 | 6.0 | n/a | 4.8 |
| 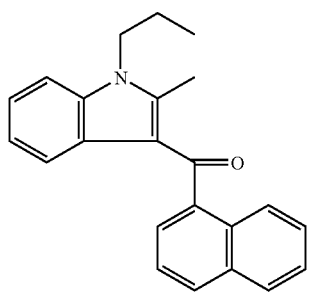 | (2-Methyl-1-propyl-2,3-dihydro-1H-indol-3-yl)-napthalen-1-yl-methanone (JWH-015) | 6.3 | 6.9 | 6.1 | 5.8 |
| 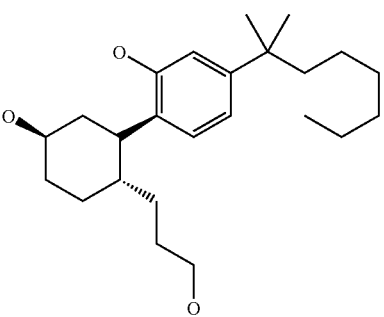 | 5-(1,1-Dimethyl-heptyl)-2-[5-hydroxy-2-(3-hydroxy-propyl)-cyclohexyl]-phenol (CP55940) | 9.0 | 9.3 | 5.3 | 5.2 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | Affinity to | | | |
| --- | --- | --- | --- | --- | --- |
| | | CB1 | CB2 | SUR 1 | SUR 2 |
| Chiral structure | 5-(1,1-Dimethyl-heptyl)-2-[5-hydroxy-2-(3-hydroxy-propyl)-cyclohexyl]-phenol (CP55940-enantiomer) | 7.2 | 7.0 | 5.3 | 5.3 |
| Chiral structure | (2-Methyl-3-morpholin-4-ylmethyl-3,4-dihydro-5-oxa-2a-azacenaphthylen-1-yl)-napthalen-1-yl-methanone (R(+)–WIN55212-2) | 7.1 | 8.1 | 4.4 | 5.4 |
| structure | 5-(4-Chloro-phenyl)-1-(2,4-dichloro-phenyl)-4-methyl-1H-pyrazole-3-carboxylic acid piperidin-1-ylamide (Rimonabant) | 8.2 | 6.0 | 5.3 | 5.4 |
| structure | 5-(4-Bromo-phenyl)-1-(2,4-dichloro-phenyl)-4-ethyl-1H-pyrazole-3-carboxylic acid piperidin-1-ylamide (SR-147778) | 7.9 | 5.9 | 5.5 | 5.6 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | Affinity to | | | |
|---|---|---|---|---|---|
| | | CB1 | CB2 | SUR 1 | SUR 2 |
| | 1-[Bis-(4-chloro-phenyl)-methyl]-3-[(3,5-difluoro-phenyl)-methanesulfonyl-methylene]-azetidine (Aventis) | 8.2 | n/a | 5.3 | 5.1 |
| | 4-Chloro-N-{[3-(4-chloro-phenyl)-4-phenyl-4,5-dihydro-pyrazol-1-yl]-methylamino-methylene}-benzenesulfonamide | 8.4 | n/a | 6.3 | 5.4 |
| | 4-Chloro-N-{[3-(4-chloro-phenyl)-4-phenyl-4,5-dihydro-pyrazol-1-yl]-methylamino-methylene}-benzenesulfonamide | 6.3 | 5.7 | 6.0 | 6.1 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | CB1 | CB2 | SUR 1 | SUR 2 |
|---|---|---|---|---|---|
| 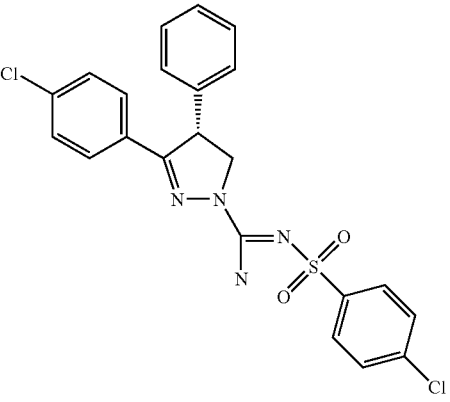 | N-{Amino-[3-(4-chloro-phenyl)-4-phenyl-4,5-dihydro-pyrazol-1-yl]-methylene}-4-chloro-benzenesulfonamide | 8.4 | 6.8 | 6.1 | 5.4 |
| 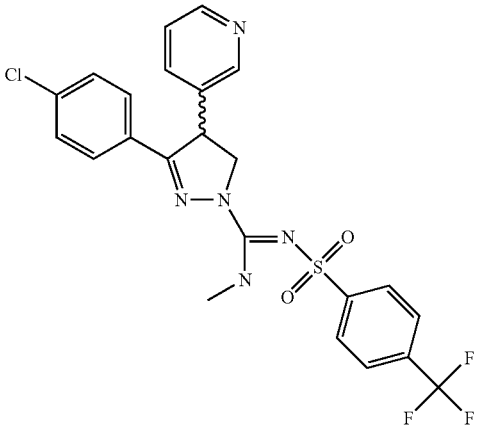 | N-{[3-(4-Chloro-phenyl)-4-pyridin-3-yl-4,5-dihydro-pyrazol-1-yl]-methylamino-methylene}-4-trifluoromethyl-benzenesulfonamide | 8.2 | — | 6.3 | 4.9 |
| 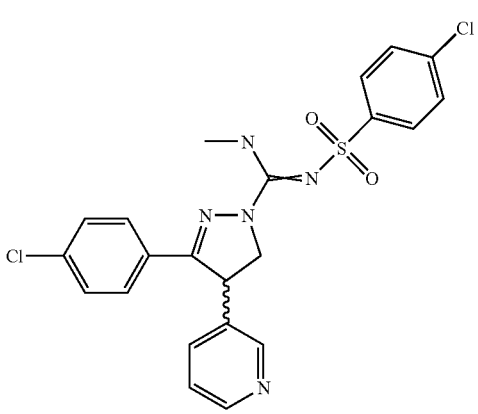 | Chloro-N-{[3-(4-chloro-phenyl)-4-pyridin-3-yl-4,5-dihydro-pyrazol-1-yl]-methylamino-methylene}-benzenesulfonamide | 7.1 | n/a | 5.6 | 5.4 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | CB1 | CB2 | SUR 1 | SUR 2 |
|---|---|---|---|---|---|
| (structure) | 4-Chloro-N-{[3-(4-chloro-phenyl)-4-(3-fluoro-phenyl)-4,5-dihydro-pyrazol-1-yl]-methoxyamino-methylene}-benzenesulfonamide | 7.7 | n/a | 5.6 | 6.1 |
| (structure) | Morpholine-4-sulfonic acid [3-(4-chloro-phenyl)-4-phenyl-4,5-dihydro-pyrazol-1-yl]-methylamino-methyleneamide | 8.3 | n/a | 6.3 | 4.0 |
| (structure) | N-{[3-(4-Chloro-phenyl)-4-(3-fluoro-phenyl)-4,5-dihydro-pyrazol-1-yl]-methylamino-methylene}-N,N-dimethyl-sulfonamide | 8.5 | n/a | 7.0 | 5.3 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | Affinity to | | | |
|---|---|---|---|---|---|
| | | CB1 | CB2 | SUR 1 | SUR 2 |
| 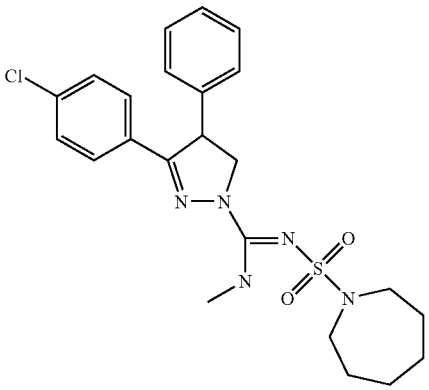 | Azepane-1-sulfonic acid [3-(4-chloro-phenyl)-4-phenyl-4,5-dihydro-pyrazol-1-yl]-methylamino-methyleneamide | 7.3 | n/a | 4.6 | 4.9 |
| 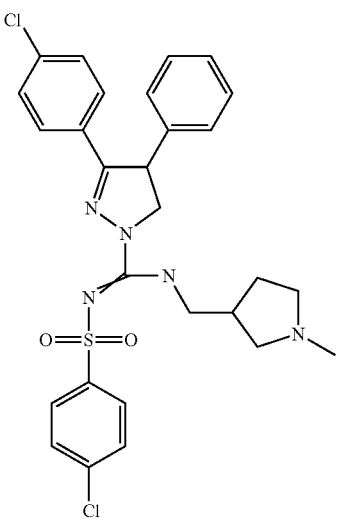 | 4-Chloro-N-{[3-(4-chloro-phenyl)-4-phenyl-4,5-dihydro-pyrazol-1-yl]-[(1-methyl-pyrrolidin-3-ylmethyl)-amino]-methylene}-benzenesulfonamide | 9.0 | 6.0 | 6.0 | 4.8 |
| 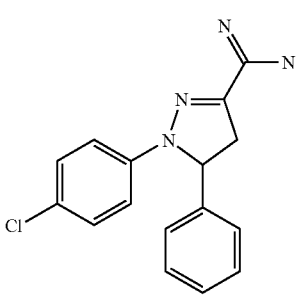 | 1-(4-Chloro-phenyl)-5-phenyl-4,5-dihydro-1H-pyrazole-3-carboxamidine | 6.2 | 6.3 | 4.0 | 4.0 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | Affinity to | | | |
|---|---|---|---|---|---|
| | | CB1 | CB2 | SUR 1 | SUR 2 |
| 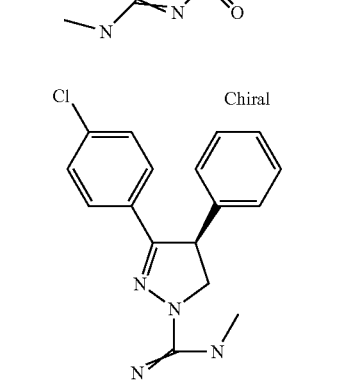 ref 2 | N-{[3-(4-Chloro-phenyl)-4-phenyl-4,5-dihydro-pyrazol-1-yl]-methylamino-methylene}-4-trifluoromethyl-benzene-sulfonamide | 8.4 | n/a | 6.3 | 4.2 |
| 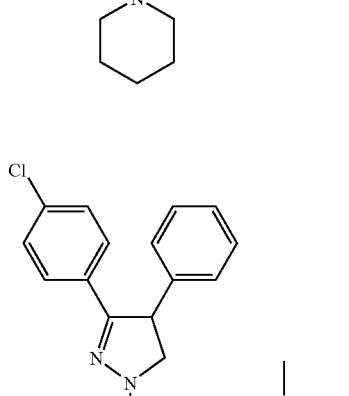 Chiral | Piperidin-1-sulfonic acid [3-(4-chloro-phenyl)-4-phenyl-4,5-dihydro-pyrazol-1-yl]-methylamino-methyleneamide | 8.1 | n/a | 5.8 | 4.3 |
| 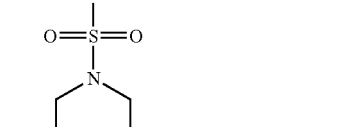 | Piperidin-1-sulfonic acid [3-(4-chloro-phenyl)-4-phenyl-4,5-dihydro-pyrazol-1-yl]-(2-dimethylamino-ethyl-amino)-methyleneamide | 8.6 | n/a | 4.0 | 4.0 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | Affinity to | | | |
|---|---|---|---|---|---|
| | | CB1 | CB2 | SUR 1 | SUR 2 |
| (structure) | N,N-Diethylamino-1-sulfonic acid [3-(4-chloro-phenyl)-4-phenyl-4,5-dihydro-pyrazol-1-yl]-methylsulfanyl-methyleneamide | 7.1 | n/a | 4.0 | 4.7 |
| (structure, ref 1, Chiral) | 2-Amino-1-[3-(4-chloro-phenyl)-4-phenyl-4,5-dihydro-pyrazol-1-yl]-3-(3,4-dichloro-phenyl)-propan-1-one | 6.0 | 6.2 | 5.4 | 4.8 |
| (structure) | Morpholine-4-sulfonic acid [3-(4-chloro-phenyl)-4-phenyl-4,5-dihydro-pyrazol-1-yl]-methylamino-methyleneamide | 7.7 | n/a | 4.0 | 5.5 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | Affinity to | | | |
|---|---|---|---|---|---|
| | | CB1 | CB2 | SUR 1 | SUR 2 |
| (structure) | N,N-Dimethylamino-1-sulfonic acid [3-(4-chloro-phenyl)-4-phenyl-4,5-dihydro-pyrazol-1-yl]-(2-fluoro-ethylamino)-methyleneamide | 7.5 | n/a | 4.3 | 4.0 |
| (structure) | Piperidine-1-sulfonic acid [3-(4-chloro-phenyl)-4-(3-fluoro-phenyl)-4,5-dihydro-pyrazol-1-yl]-methylamino-methyleneamide | 7.5 | 6.1 | 4.5 | 6.3 |
| (structure) | 5-(4-Chloro-phenyl)-1-(2,4-dichloro-phenyl)-4,5-dihydro-1H-pyrazol-3-carboxylic acid piperidine-1-ylamide | 7.4 | 6.1 | 5.4 | 5.6 |
| (structure) | 1-(4-Chloro-phenyl)-5-phenyl-4,5-dihydro-1H-pyrazole-3-carboxylic acid piperidin-1-ylamide | 7.2 | n/a | 4.0 | 5.1 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | Affinity to | | | |
|---|---|---|---|---|---|
| | | CB1 | CB2 | SUR 1 | SUR 2 |
| (structure) | Piperdine-1-sulfonic acid [1-(4-chloro-phenyl)-5-phenyl-4,5-dihydro-1H-pyrazol-3-yl]-methylamino-methyleneamide | 7.3 | n/a | 6.1 | 4.5 |
| (structure) | Morpholine-4-sulfonic acid [1-(2,4-dichloro-phenyl)-5-phenyl-4,5-dihydro-1H-pyrazol-3-yl]-methylamino-methyleneamide | 6.9 | n/a | 5.3 | 5.0 |
| (structure) ref 1 | 4-Chloro-N-[[3-(4-chloro-phenyl)-4-phenyl-4,5-dihydro-pyrazol-1-yl]-(2-fluoro-ethylamino)-methylene]-benzenesulfonamide | 7.7 | n/a | 4.6 | 4.6 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | Affinity to | | | |
|---|---|---|---|---|---|
| | | CB1 | CB2 | SUR 1 | SUR 2 |
| (structure, ref 2) | 4-Chloro-N-[[3-(4-chloro-phenyl)-4-phenyl-4,5-dihydro-pyrazol-1-yl]-(2-fluoro-ethylamino)-methylene]-benzenesulfonamide | 6.9 | n/a | 4.6 | 5.0 |
| (structure, ref 1) | N-{Amino-[3-(4-chloro-phenyl)-4-phenyl-4,5-dihydro-pyrazol-1-yl]-methylene}-4-chloro-benzenesulfonamide | 7.4 | 6.4 | 6.0 | 5.1 |
| (structure) | 4-Chloro-N-[3-(4-chloro-phenyl)-4-phenyl-4,5-dihydro-pyrazole-1-carbonyl]-benzenesulfonamide | 6.5 | n/a | 5.5 | 4.8 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | Affinity to | | | |
|---|---|---|---|---|---|
| | | CB1 | CB2 | SUR 1 | SUR 2 |
| (structure) | 4-Chloro-N-[[3-(4-chloro-phenyl)-4-phenyl-4,5-dihydro-pyrazol-1-yl]-(2-ethylamino-ethylamino)-methylene]-Benzenesulfonamide | 8.1 | n/a | 5.1 | 5.3 |
| (structure) | 4-Chloro-N-{[3-(4-chloro-phenyl)-4-phenyl-4,5-dihydro-pyrazol-1-yl]-[(1-methyl-pyrrolidin-2-ylmethyl)-amino]-methylene}-benzenesulfonamide | 8.3 | n/a | n/a | 5.1 |
| (structure) | 4-Chloro-N-[[3-(4-chloro-phenyl)-4-phenyl-4,5-dihydro-pyrazol-1-yl]-(4-pyrrolidin-1-yl-butylamino)-methylene]-benzenesulfonamide | 7.4 | n/a | 4.3 | 5.4 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | Affinity to | | | |
|---|---|---|---|---|---|
| | | CB1 | CB2 | SUR 1 | SUR 2 |
| 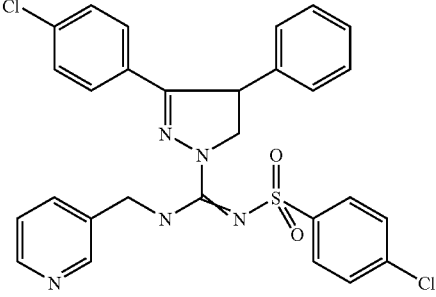 | 4-Chloro-N-{[3-(4-chloro-phenyl)-4-phenyl-4,5-dihydro-pyrazol-1-yl]-[(pyridin-3-ylmethyl)-amino]-methylene}-benzenesulfonamide | 6.4 | 6.3 | 5.9 | 5.7 |
| 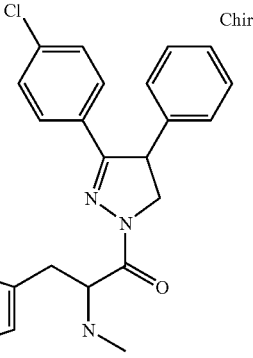 Chiral | 1-[3-(4-Chloro-phenyl)-4-phenyl-4,5-dihydro-pyrazol-1-yl]-3-(1H-indol-2-yl)-2-methylamino-propan-1-one | 8.0 | 6.9 | 6.6 | 4.6 |
| 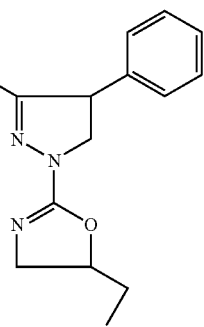 | 2-[3-(4-Chloro-phenyl)-4-phenyl-4,5-dihydro-pyrazol-1-yl]-5-ethyl-4,5-dihydro-oxazole | 6.2 | n/a | 5.5 | 4.4 |
| 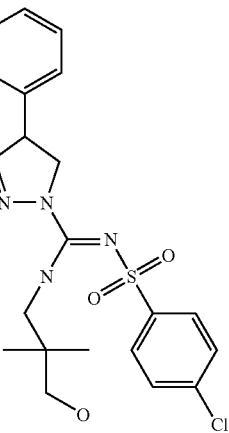 | 4-Chloro-N-[[3-(4-chloro-phenyl)-4-phenyl-4,5-dihydro-pyrazol-1-yl]-(3-hydroxy-2,2-dimethyl-propylamino)-methylene]-benzenesulfonamide | 6.7 | 6.1 | 4.5 | 5.4 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | CB1 | CB2 | SUR 1 | SUR 2 |
|---|---|---|---|---|---|
| (structure) | N,N-Diethylamino-1-sulfonic acid [3-(4-chloro-phenyl)-4-hydroxy-4-phenyl-4,5-dihydro-pyrazol-1-yl]-methylamino-methyleneamide | 7.4 | n/a | 4.0 | 5.9 |
| (structure) | 5-(4-Bromo-phenyl)-1-(2,4-dichloro-phenyl)-1H-pyrazole-3-carbonitrile | 6.3 | n/a | 4.0 | 5.4 |
| (structure) | 8-Chloro-1-(2,4-dichloro-phenyl)-1,3a,4,5,6,10b-hexahydro-1,2-diaza-benzo[e]azulene-3-carboxylic acid piperidin-1-ylamide | 6.9 | 6.9 | 5.5 | 4.0 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | CB1 | CB2 | SUR 1 | SUR 2 |
|---|---|---|---|---|---|
| 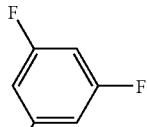 | 5-(4-Bromo-phenyl)-1-(2,4-dichloro-phenyl)-3-[2-(3,5-difluoro-phenyl)-2-methanesulfonyl-vinyl]-4-methyl-1H-pyrazole | 7.3 | 5.9 | 4.0 | 4.0 |
| 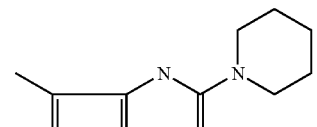 | Piperidine-1-carboxylic acid [5-(4-chloro-phenyl)-1-(2,4-dichloro-phenyl)-4-methyl-1H-pyrazol-3-yl]-amide | 6.9 | n/a | 4.7 | 4.7 |
| 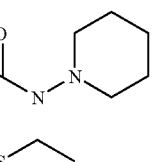 | 1-(4-Chloro-phenyl)-2-(2,4-dichloro-phenyl)-5-ethylsulfanyl-1H-imidazole-4-carboxylic acid piperidin-1-ylamide | 7.4 | n/a | 5.1 | 5.3 |
| 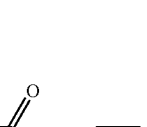 | 2-(2,4-Dichloro-phenyl)-1-(4-trifluoromethyl-phenyl)-1H-imidazole-4-carboxylic acid piperidin-1-ylamide | 7.6 | n/a | 5.6 | 5.3 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | CB1 | CB2 | SUR 1 | SUR 2 |
|---|---|---|---|---|---|
| 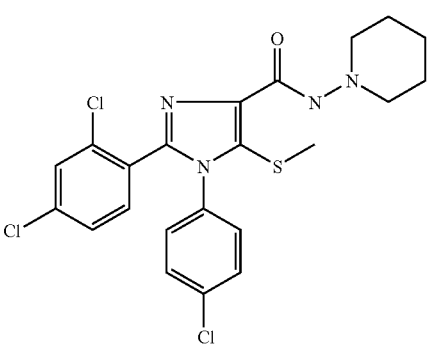 | 1-(4-Chloro-phenyl)-2-(2,4-dichloro-phenyl)-5-methylsulfanyl-1H-imidazole-4-carboxylic acid piperidin-1-ylamide | 8.0 | 6.0 | 5.1 | 5.6 |
| 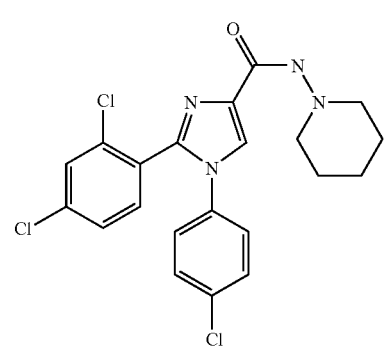 | 1-(4-Chloro-phenyl)-2-(2,4-dichloro-phenyl)-1H-imidazole-4-carboxylic acid piperidin-1-ylamide | 8.1 | 6.2 | 4.5 | 5.3 |
| 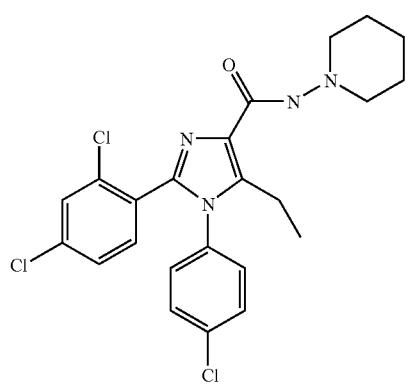 | 1-(4-Chloro-phenyl)-2-(2,4-dichloro-phenyl)-5-ethyl-1H-imidazole-4-carboxylic acid piperidin-1-ylamide | 8.7 | 6.3 | 5.3 | 5.5 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | CB1 | CB2 | SUR 1 | SUR 2 |
|---|---|---|---|---|---|
| (structure) | 1-(4-Bromo-phenyl)-2-(2,4-dichloro-phenyl)-5-ethyl-1H-imidazole-4-carboxylic acid piperidin-1-ylamide | 7.5 | n/a | 5.4 | 5.3 |
| (structure) | 1-(4-Bromo-phenyl)-5-chloro-2-(2,4-dichloro-phenyl)-1H-imidazole-4-carboxylic acid piperidin-1-ylamide | 8.6 | n/a | 5.4 | 5.5 |
| (structure) | 1-(4-Bromo-phenyl)-2-(2,4-dichloro-phenyl)-5-ethyl-1H-imidazole-4-carboxylic acid cyclohexylamide | 7.0 | 6.7 | 4.0 | 5.1 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | CB1 | CB2 | SUR 1 | SUR 2 |
|---|---|---|---|---|---|
| 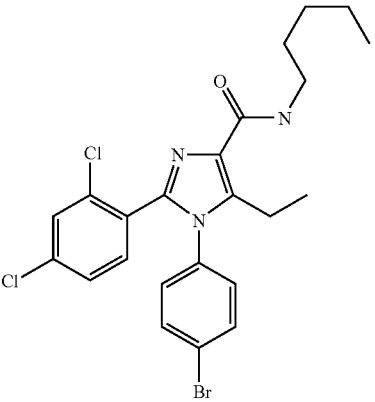 | 1-(4-Bromo-phenyl)-2-(2,4-dichloro-phenyl)-5-ethyl-1H-imidazole-4-carboxylic acid pentylamide | 7.5 | n/a | 6.1 | 5.6 |
| 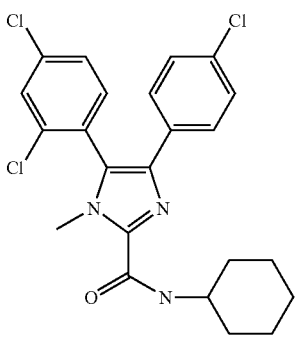 | 4-(4-Chloro-phenyl)-5-(2,4-dichloro-phenyl)-1-methyl-1H-imidazole-2-carboxylic acid cyclohexylamide | 7.2 | n/a | 4.0 | 4.7 |
| 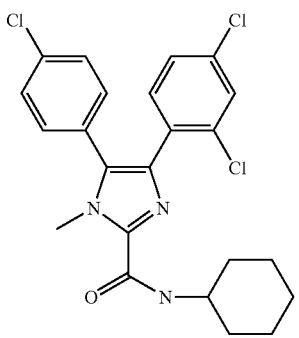 | 4-(4-Chloro-phenyl)-5-(2,4-dichloro-phenyl)-3-methyl-1H-imidazole-2-carboxylic acid cyclohexylamide | 7.1 | n/a | 4.0 | 4.9 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | CB1 | CB2 | SUR 1 | SUR 2 |
|---|---|---|---|---|---|
| | 1-(5-Chloro-pyridin-2-yl)-2-(2,4-dichloro-phenyl)-5-ethyl-1H-imidazole-4-carboxylic acid piperidin-1-ylamide | 7.6 | n/a | 4.0 | 4.4 |
| | 1-(4-Chloro-phenyl)-2-(2,4-dichloro-phenyl)-5-methyl-1H-imidazole-4-carboxylic acid (4-hydroxy-cyclo-hexyl)-amide | 6.6 | n/a | 4.0 | 5.0 |
| | 1-(4-Chloro-phenyl)-2-(2,4-dichloro-phenyl)-5-methyl-1H-imidazole-4-carboxylic acid azepan-1-ylamide | 7.2 | 7.6 | 5.2 | 5.7 |
| | 2-(2,4-Dichloro-phenyl)-5-ethyl-1-phenyl-1H-imidazole-4-carboxylic acid piperidin-1-ylamide | 7.0 | 7.6 | 4.0 | 5.3 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | CB1 | CB2 | SUR 1 | SUR 2 |
|---|---|---|---|---|---|
| | 2-(1,5-Dimethyl-1H-pyrrol-2-yl)-5-ethyl-1-phenyl-1H-imidazole-4-carboxylic acid cyclohexylamide | n/a | 6.8 | 4.0 | 4.0 |
| | 1-(4-Chloro-phenyl)-5-ethyl-2-(3-methyl-pyridin-2-yl)-1H-imidazole-4-carboxylic acid piperidin-1-ylamide | n/a | 6.6 | 4.0 | 4.8 |
| | 1-(4-Chloro-phenyl)-5-ethyl-2-(3-methyl-pyridin-2-yl)-1H-imidazole-4-carboxylic acid cyclohexylamide | n/a | 6.1 | 4.0 | 5.5 |
| | 1-(4-Chloro-phenyl)-2-(2,4-dichloro-phenyl)-5-methyl-1H-imidazole-4-carboxylic acid (4-trifluoromethyl-phenyl)-amide | 6.7 | n/a | 4.5 | 5.3 |
| | 2-(2,4-Dichloro-phenyl)-5-methyl-1-pyridin-2-yl-1H-imidazole-4-carboxylic acid piperidin-1-ylamide | 7.3 | 6.2 | 4.0 | 4.1 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | CB1 | CB2 | SUR 1 | SUR 2 |
|---|---|---|---|---|---|
| 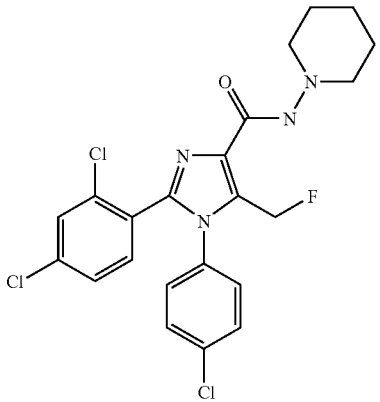 | 1-(4-Chloro-phenyl)-2-(2,4-dichloro-phenyl)-5-fluoromethyl-1H-imidazole-4-carboxylic acid piperidin-1-ylamide | 7.2 | 6.1 | 5.2 | 5.5 |
| 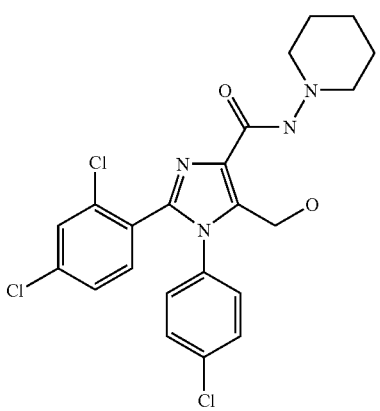 | 1-(4-Chloro-phenyl)-2-(2,4-dichloro-phenyl)-5-hydroxymethyl-1H-imidazole-4-carboxylic acid piperidin-1-ylamide | 7.6 | 6.2 | 4.0 | 4.7 |
| 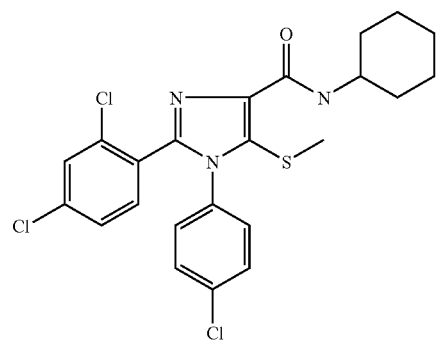 | 1-(4-Chloro-phenyl)-2-(2,4-dichloro-phenyl)-5-methylsulfanyl-1H-imidazole-4-carboxylic acid cyclohexylamide | 7.2 | 6.6 | 6.3 | 5.8 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | Affinity to | | | |
|---|---|---|---|---|---|
| | | CB1 | CB2 | SUR 1 | SUR 2 |
| [structure] | 1-(4-Chloro-phenyl)-2-(2,4-dichloro-phenyl)-5-methanesulfonyl-1H-imidazole-4-carboxylic acid piperidin-1-ylamide | 7.8 | n/a | 4.0 | 5.0 |
| [structure] | 1-(4-Chloro-phenyl)-2-(2,4-dichloro-phenyl)-5-methanesulfinyl-1H-imidazole-4-carboxylic acid piperidin-1-ylamide | 7.4 | n/a | 4.0 | 4.9 |
| [structure] | 5-(4-Chloro-phenyl)-4-(2,5-dichloro-phenyl)-1-methyl-1H-imidazole-2-carboxylic acid piperidin-1-ylamide | 6.7 | 6.4 | 4.6 | 5.0 |
| [structure] | 2-(2-Chloro-phenyl)-1-(5-chloro-pyridin-2-yl)-5-ethyl-1H-imidazole-4-carboxylic acid piperidin-1-ylamide | 7.9 | n/a | 4.0 | 4.8 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | CB1 | CB2 | SUR 1 | SUR 2 |
|---|---|---|---|---|---|
| | 1-(4-Chloro-phenyl)-2-(2,4-dichloro-phenyl)-5-(2,2,2-trifluoro-ethyl)-1H-imidazole-4-carboxylic acid piperidin-1-ylamide | 7.5 | n/a | 4.8 | 5.7 |
| | N-[1-(4-Chloro-phenyl)-2-(2,4-dichloro-phenyl)-5-methyl-1H-imidazol-4-yl]-benzamide | 7.0 | 6.3 | 5.7 | 5.2 |
| | 1-(4-Chloro-phenyl)-2-(2,4-dichloro-phenyl)-5-pyrrolidin-1-ylmethyl-1H-imidazole-4-carboxylic acid piperidin-1-ylamide | 6.3 | n/a | 4.0 | 4.6 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | CB1 | CB2 | SUR 1 | SUR 2 |
|---|---|---|---|---|---|
| | 2-[1-(4-Chloro-phenyl)-2-(2,4-dichloro-phenyl)-5-methyl-1H-imidazol-4-yl]-hexan-2-ol | 6.6 | n/a | 5.8 | 5.3 |
| | 1-(4-Chloro-phenyl)-2-(2,4-dichloro-phenyl)-5-methyl-4-pentyl-1H-imidazole | 7.0 | n/a | 5.8 | 5.3 |
| | 2,5-Dimethyl-1-phenyl-1H-imidazole-4-carboxylic acid adamantan-2-ylamide | n/a | 9.0 | 6.0 | 4.6 |
| | 1-(4-Chloro-phenyl)-2-(2-chloro-phenyl)-5-methylsulfanyl-1H-imidazole-4-carboxylic acid piperidin-1-ylamide | n/a | 5.2 | 8.2 | n/a |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | Affinity to | | | |
| --- | --- | --- | --- | --- | --- |
| | | CB1 | CB2 | SUR 1 | SUR 2 |
| (structure) | 2-(2-Chloro-phenyl)-1-(4-trifluoromethyl-phenyl)-1H-imidazole-4-carboxylic acid piperidin-1-ylamide | 7.0 | n/a | 6.0 | 5.7 |
| (structure) | 5-(4-Chloro-phenyl)-4-(2,4-dichloro-phenyl)-thiazole-2-carboxylic acid piperidin-1-ylamide | 6.7 | n/a | 5.7 | 5.5 |
| (structure) | 5-(4-Chloro-phenyl)-1-(2,4-dichloro-phenyl)-1H-[1,2,4]triazole-3-carboxylic acid pyrrolidin-1-ylamide | 6.6 | n/a | 4.0 | 4.4 |
| (structure) | 1-(4-Chloro-phenyl)-5-(2,4-dichloro-phenyl)-1H-[1,2,4]triazole-3-carboxylic acid piperidin-1-yl-amide | 6.5 | n/a | 5.0 | 5.0 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | Affinity to | | | |
|---|---|---|---|---|---|
| | | CB1 | CB2 | SUR 1 | SUR 2 |
| (structure) | 5-Pentyl-4-phenyl-thiazole-2-carboxylic acid (hexahydro-2,5-methano-pentalen-3a-yl)-amide | 6.4 | 7.0 | 4.0 | 4.0 |
| (structure) | 4-Pentyl-5-phenyl-thiazole-2-carboxylic acid (hexahydro-2,5-methano-pentalen-3a-yl)-amide | 7.8 | 8.1 | 4.0 | 4.0 |
| (structure) | 1-{(4-Chloro-benzene-sulfonylamino)-[3-(4-chloro-phenyl)-4-phenyl-4,5-dihydro-pyrazol-1-yl]-methyl}-piperidine-4-carboxylic acid amide | 8.2 | n/a | 5.5 | 5.2 |
| (structure) | 4-Chloro-N-{[3-(4-chloro-phenyl)-4-phenyl-4,5-dihydro-pyrazol-1-yl]-[2-(2-oxo-pyrrolidin-1-yl)-ethylamino]-methylene}-benzenesulfonamide | 8.2 | n/a | 6.3 | 5.9 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | Affinity to | | | |
| --- | --- | --- | --- | --- | --- |
| | | CB1 | CB2 | SUR 1 | SUR 2 |
| (structure) | 4-Chloro-N-[[3-(4-chloro-phenyl)-4-phenyl-4,5-dihydro-pyrazol-1-yl]-(2-cyano-ethylamino)-methylene]-benzene-sulfonamide | 7.9 | n/a | 6.7 | 5.9 |
| (structure) | 4-Chloro-N-[[3-(4-chloro-phenyl)-4-phenyl-4,5-dihydro-pyrazol-1-yl]-(methoxy-methyl-amino)-methylene]-benzenesulfonamide | 6.7 | n/a | 5.9 | 5.9 |
| (structure) | 4-Chloro-N-{[3-(4-chloro-phenyl)-4-phenyl-4,5-dihydro-pyrazol-1-yl]-[(piperidin-4-ylmethyl)-amino]-methylene}-benzenesulfonamide | 8.6 | n/a | 6.2 | 4.9 |
| (structure) | 4-Chloro-N-[[3-(4-chloro-phenyl)-4-phenyl-4,5-dihydro-pyrazol-1-yl]-(piperidin-4-ylamino)-methylene]-benzenesulfonamide | 8.2 | n/a | 4.5 | 4.6 |

TABLE 1-continued

CB$_x$ modulators with their affinities for the CB1 and/or CB2 receptor affinities, (cloned human cannabinoid (CB1 and CB2 respectively) receptors expressed in CHO cells according to the procedures described hereinabove), expressed as pK$_i$ values.

| compound/name | chemical name | Affinity to | | | |
|---|---|---|---|---|---|
| | | CB1 | CB2 | SUR 1 | SUR 2 |
| (structure) | Morpholine-4-sulfonic acid [3-(4-chloro-phenyl)-4-phenyl-4,5-dihydro-pyrazol-1-yl]-(cyclopropylmethyl-amino)-methyleneamide | 8.5 | n/a | 6.0 | 5.7 |

The data in Table I demonstrate that the tested CB$_x$ modulators act selectively on the SUR1 subunit and/or on the SUR2 subunit.

Compounds included within the scope of the present disclosure have an in vitro binding affinity for the cannabinoid CB$_1$ receptor (measured as pK$_i$) between about 6.0 and about 9.0, between about 5.0 and about 10.0, between about 4.0 and about 12.0, between about 7.0 and about 9.0 and between about 8.0 and about 9.0 using membrane preparations of CHO cells on which the human cannabinoid CB$_1$ receptor is stably transfected in conjunction with [$^3$H]CP-55,940 as a radioligand as described herein. Further compounds include those with a binding affinity for the cannabinoid CB$_1$ receptor (measured as pK$_i$) using the previously described method of greater than about 2.0, greater than about 3.0, greater than about 4.0, greater than about 5.0, greater than about 6.0, greater than about 7.0, greater than about 8.0, greater than about 9.0, greater than about 10.0, greater than about 11.0 and greater than about 12.0. Further compounds included within the scope of the present disclosure are those with a binding affinity for the cannabinoid CB$_1$ receptor (measured as pK$_i$) using the previously described method of about 4.0, about 5.0, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0 about 10, about 11.0 and about 12.0.

Compounds included within the scope of the present disclosure have an in vitro binding affinity for the cannabinoid CB$_2$ receptor (measured as pK$_i$) between about 5.0 and about 10.0, between about 4.0 and about 12.0, between about 3.0 and about 12.0, between about 7.0 and about 10.0 and between about 8.0 and about 10.0 using membrane preparations of CHO cells on which the human cannabinoid CB$_2$ receptor is stably transfected in conjunction with [$^3$H]CP-55,940 as a radioligand as described herein. Further compounds include those with a binding affinity for the cannabinoid CB$_2$ receptor (measured as pK$_i$) using the previously described method of greater than about 2.0, greater than about 3.0, greater than about 4.0, greater than about 5.0, greater than about 6.0, greater than about 7.0, greater than about 8.0, greater than about 9.0, greater than about 10.0, greater than about 11.0 and greater than about 12.0. Further compounds included within the scope of the present disclosure are those with a binding affinity for the cannabinoid CB$_2$ receptor (measured as pK$_i$) using the previously described method of about 4.0, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9 about 10, about 11.0 and about 12.0.

Compounds included within the scope of the present disclosure have an in vitro affinity for the binding sites for sulonylureas and K$_{ATP}$ channel openers on hamster SUR1 (measured as pK$_i$) between about 3.0 and about 8.0, between about 2.0 and about 10.0, between about 1.0 and about 11.0, between about 4.0 and about 8.0 and between about 6.0 and about 9.0 using membrane from COS-cells transiently expressing hamster SUR1 incubated in the presence of [$^3$H] glibenclamide with increasing amounts of the compound to be tested as described herein. Further compounds include those with an affinity for the binding sites for sulonylureas and K$_{ATP}$ channel openers on hamster SUR1 (measured as pK$_i$) using the previously described method of greater than about 1.0, greater than about 2.0, greater than about 3.0, greater than about 4.0, greater than about 5.0, greater than about 6.0, greater than about 7.0, greater than about 8.0, greater than about 9.0, greater than about 10.0 and greater than about 11.0. Further compounds include those with an affinity for the binding sites for sulonylureas and K$_{ATP}$ channel openers on hamster SUR1 (measured as pK$_i$) using the previously described method of about 1.0, about 2.0, about 3.0, about 3.1, about 3.2, about 3.3, about 3.4, about 3.5, about 3.6; about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9 and about 9.0.

Compounds included within the scope of the present disclosure have an in vitro affinity for the binding sites for sulonylureas and $K_{ATP}$ channel openers on rat SUR2 (measured as $pK_i$) between about 2.5 and about 7.0, between about 2.0 and about 8.0, between about 1.0 and about 9.0, between about 3.0 and about 7.0 and between about 5.0 and about 8.0 using membrane from COS-cells transiently expressing rat SUR2 incubated in the presence of [$^3$H]glibenclamide with increasing amounts of the compound to be tested as described herein. Further compounds include those with an affinity for the binding sites for sulonylureas and $K_{ATP}$ channel openers on rat SUR2 (measured as $pK_i$) using the previously described method of greater than about 1.0, greater than about 2.0, greater than about 3.0, greater than about 4.0, greater than about 5.0, greater than about 6.0, greater than about 7.0, greater than about 8.0, greater than about 9.0 and greater than about 10.0. Further compounds include those with an affinity for the binding sites for sulonylureas and $K_{ATP}$ channel openers on rat SUR2 (measured as $pK_1$) using the previously described method of about 1.0, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9 and about 8.0.

4. Determination of the $K_{ATP}$ Opening Effects of Compounds Through Insulin Secretion in Rat Perifused Pancreatic Islets Animals: Male Wistar rats weighing between 175 and 200 g were group housed in standard animal cages at a temperature of 21±2° C. and humidity of 55±10%. The animals were maintained on a 12 h light-dark cycle (lights on 06.00-18.00 h) with free access to standard rodent diet (B&K Universal Ltd standard rat and mouse diet (BK 001P), Beekay Feeds, B&K Universal Ltd, Hull, East Riding of Yorkshire) and tap water. The rats were conditioned to this environment for at least one week before experimentation.

Experimental procedures: After the rats were sacrificed, the branch of the bile duct leading to the liver and the duodenal end of the duct in the pancreas were clamped and the pancreas distended by injection of ice-cold 0.9 mg/ml collagenase solution into the bile duct. The pancreas were then removed and incubated statically for 10-12 min at 37° C. Following incubation, 10 ml of cold buffer was added and the suspension shaken vigorously by hand for 1 min. The islets were allowed to settle for 5 min on ice and washed three times using ice-cold buffer. Well formed and good sized islets from 3 rats were hand-picked (under a low power microscope) and pooled and a final selection of islet transferred to the perifusion apparatus. Oxygenated (95% $O_2$/5% $CO_2$) Gey & Gey buffer containing 1 mg/ml bovine serum albumin and 4 mM glucose were used throughout the experiment unless otherwise stated (see Dickinson et al. Eur. J. Pharmacol. 1997; 339: 69-76 for further details).

Compounds were either tested at the advised concentration or the solubility was determined in the experimental conditions and a maximum soluble drug concentration used for experiments (DMSO or ethanol will be used as the solvents at a maximum 0.1% in the assay buffer).

Two experiments were performed in parallel in two identical, independent sets of perifusion apparatus each consisting of sufficient number of chambers. Each chamber was loaded with 20 hand-picked islets. Islets were perifused for an initial 30 min period in media containing 4 mM glucose. Perifusate was then collected at 2 min intervals for the remainder of the experiment. After the first 10 min of the experiment (to collect baseline insulin values), the media in each chamber was switched to one containing 11 mM glucose and the relevant drug concentration/vehicle/diazoxide concentration and perifusate collected for a further 62 min to produce a total of 36 fractions for each chamber. Perifusate samples were then pooled to create three samples per chamber as follows: Baseline (4 mM): Samples 1-5 (first 10 minutes); 0-30 minutes (11 mM glucose): Samples 6-21; 30-60 minutes (11 mM glucose): Samples 22-36. Perifusate fractions were stored at −75° C. until required for insulin assay. Insulin content of fractions were assayed using a 96-well ELISA assay (Mercodia). Initial insulin assays were performed in triplicate on three pooled fractions from each chamber.

Drugs: All chemicals were obtained from Sigma (or other appropriate commercial supplier).

Result: The three islet preparations showed a consistent degree of glucose dependent insulin secretion. The mean insulin secretion at 11 mM glucose was 98.3±12.6 pg/islet/min and 130.4±22.0 pg/islet/min at 0-30 and 30-60 minutes, respectively. In the presence of 4 mM glucose this was significantly lower and was 3.8±0.6 pg/islet/min and 3.4±0.1 pg/islet/min at 0-30 and 30-60 minutes, respectively. Thus, insulin secretion was increased by 26 times and 38 times by 11 mM glucose at 0-30 and 30-60 minutes, respectively. Data were initially expressed as a simple mean of the three experiments for insulin secretion (pg/islet/min) and multiple t-tests (against the corresponding vehicle time period) used to determine potential significant effects of treatments. Alternatively, data were also calculated as a % vehicle effect for each experimental day. This latter approach was deemed to be the more powerful analysis as it corrected for the day to day variation in insulin release from the islets. Diazoxide significantly inhibited insulin secretion by an average of 55.3% (0-30 min) and 58.9% (30-60 min).

Table 2—$K_{ATP}$ channel openers analyzed according to the procedure described hereinabove and expressed as percent (%) inhibition.

TABLE 2

K$_{ATP}$ channel openers analyzed according to the procedure described hereinabove and expressed as percent (%) inhibition.

| Compound/name | Chemical name | % Inhibition 0-30/30-60 |
|---|---|---|
|  | (2-Iodo-5-nitro-phenyl)-[1-(1-methyl-piperidin-2-ylmethyl)-1H-indol-3-yl]-methanone (AM-1241) | 97/74 |
|  | 1-(4-Chloro-phenyl)-2-(2-chloro-phenyl)-5-ethyl-1H-imidazole-4-carboxylic acid piperidin-1-ylamide (Bayer) | 59/45 |
|  | 5-(1,1-Dimethyl-heptyl)-2-[5-hydroxy-2-(3-hydroxy-propyl)-cyclohexyl]-phenol (CP55940) | 91/56 |
|  | (2-Methyl-3-morpholin-4-ylmethyl-3,4-dihydro-5-oxa-2a-azacenaphthylen-1-yl)-naphthalen-1-yl-methanone (R(+)-WIN5512-2) | 80/35 |

TABLE 2-continued $K_{ATP}$ channel openers analyzed according to the procedure described hereinabove and expressed as percent (%) inhibition.

| Compound/name | Chemical name | % Inhibition 0-30/30-60 |
|---|---|---|
| 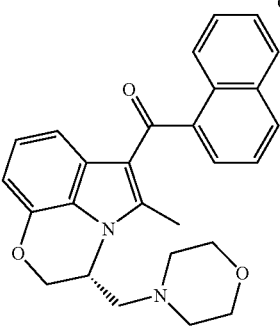 Chiral | (2-Methyl-3-morpholin-4-ylmethyl-3,4-dihydro-5-oxa-2a-azacenaphthylen-1-yl)-naphthalen-1-yl-methanone (R(+)-WIN5512-2) | 69/40 |
| 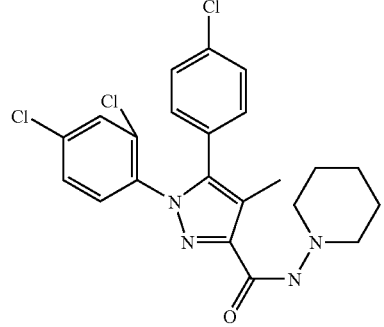 | 5-(4-Chloro-phenyl)-1-(2,4-dichloro-phenyl)-4-methyl-1H-pyrazole-3-carboxylic acid piperidin-1-ylamide (Rimonabant) | 22/18 |
| 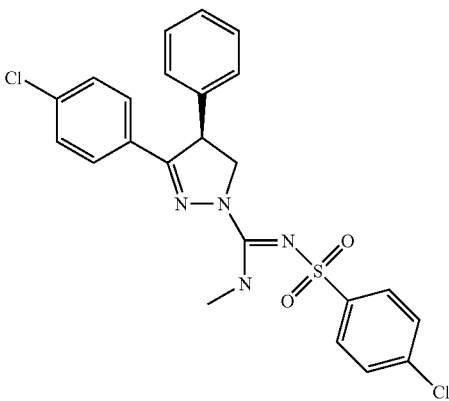 | 4-Chloro-N-{[3-(4-chloro-phenyl)-4-phenyl-4,5-dihydro-pyrazol-1-yl]-methylamino-methylene}-benzenesulfonamide | 42/22 |
| 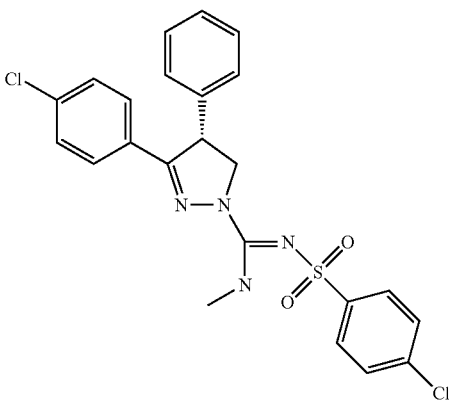 | 4-Chloro-N-{[3-(4-chloro-phenyl)-4-phenyl-4,5-dihydro-pyrazol-1-yl]-methylamino-methylene}-benzenesulfonamide | 59/25 |

TABLE 2-continued

K$_{ATP}$ channel openers analyzed according to the procedure described hereinabove and expressed as percent (%) inhibition.

| Compound/name | Chemical name | % Inhibition 0-30/30-60 |
|---|---|---|
| 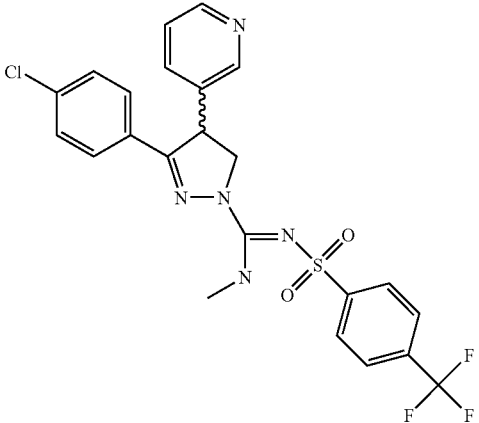 | N-{[3-(4-Chloro-phenyl)-4-pyridin-3-yl-4,5-dihydro-pyrazol-1-yl]-methylamino-methylene}-4-trifluoromethyl-benzenesulfonamide | 58/31 |
| 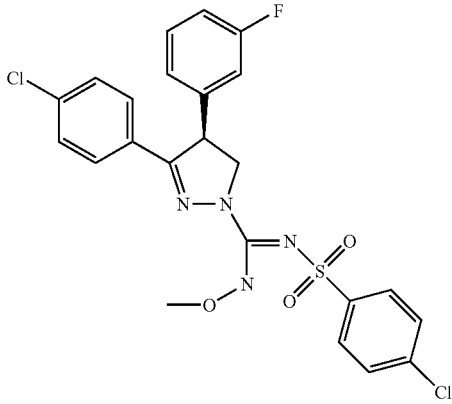 | 4-Chloro-N-{[3-(4-chloro-phenyl)-4-(3-fluoro-phenyl)-4,5-dihydro-pyrazol-1-yl]-methoxyamino-methylene}-benzenesulfonamide | 90/95 |
| 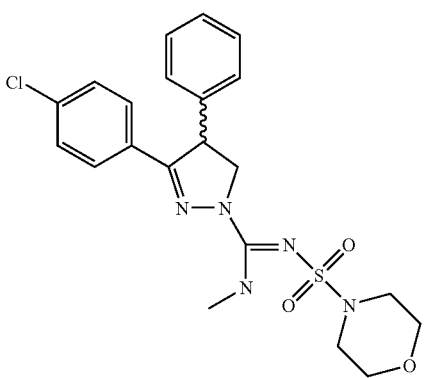 | Mopholine-4-sulfonic acid [3-(4-chloro-phenyl)-4-phenyl-4,5-dihydro-pyrazol-1-yl]-methylamino-methyleneamide | 83/91 |

TABLE 2-continued

K$_{ATP}$ channel openers analyzed according to the procedure described hereinabove and expressed as percent (%) inhibition.

| Compound/name | Chemical name | % Inhibition 0-30/30-60 |
|---|---|---|
| (structure) | N-{[3-(4-Chloro-phenyl)-4-(3-fluoro-phenyl)-4,5-dihydro-pyrazol-1-yl]-methylamino-methylene}-N,N-dimethyl-sulfonamide | 72/77 |
| (structure, Chiral) | Piperidine-1-sulfonic acid [3-(4-chloro-phenyl)-4-phenyl-4,5-dihydro-pyrazol-1-yl]-methylamino-methyleneamide | 49/40 |
| (structure) | Piperidine-1-sulfonic acid [3-(4-chloro-phenyl)-4-phenyl-4,5-dihydro-pyrazol-1-yl]-(2-dimethylamino-ethylamino)-methyleneamide | 71/64 |

TABLE 2-continued

K$_{ATP}$ channel openers analyzed according to the procedure described hereinabove and expressed as percent (%) inhibition.

| Compound/name | Chemical name | % Inhibition 0-30/30-60 |
|---|---|---|
| (structure) | Piperidine-1-sulfonic acid [1-(4-chloro-phenyl)-5-phenyl-4,5-dihydro-1H-pyrazol-3-yl]-methylamino-methyleneamide | 84/47 |
| (structure, Chiral) | 1-[3-(4-Chloro-phenyl)-4-phenyl-4,5-dihydro-pyrazol-1-yl]-3-(1H-indol-2-yl)-2-methylamino-propan-1-one | 64/53 |
| (structure) | 1-(4-Chloro-phenyl)-2-(2-chloro-phenyl)-5-methylsulfanyl-1H-imidazole-4-carboxylic acid piperidin-1-ylamide | 56/36 |

The foregoing tests demonstrate that candidate compounds selected on the basis of their affinity for the K$_{ATP}$ channel do inhibit glucose-stimulated insulin secretion. It follows that the candidate compounds function as K$_{ATP}$ channel openers under the conditions described hereinabove.

Suitable K$_{ATP}$ channel opening compounds included within the scope of the present disclosure have a glucose-stimulated insulin secretion percent inhibition at 0-30 minutes in the experimental procedure set forth above of greater than about 10%, greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75%, greater than about 80%, greater than about 855%, greater than about 90%, greater than about 91%, greater than about 92%, greater than about 93%, greater than about 94%, greater than about 95%, greater than about 96%, greater than about 97%, greater than about 98%, greater than about 99% and greater than about 99.5%.

Suitable K$_{ATP}$ channel opening compounds included within the scope of the present disclosure have a glucose-stimulated insulin secretion percent inhibition at 30-60 minutes in the experimental procedure set forth above of greater than about 10%, greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75%, greater than about 80%, greater than about 855%, greater than about 90%, greater than about 91%, greater than about 92%, greater than about 93%, greater than about 94%, greater than about 95%, greater than about 96%, greater than about 97%, greater than about 98%, greater than about 99% and greater than about 99.5%.

The pharmaceutical compositions according to the present disclosure can be prepared in a manner to obtain formulations suitable for enteral, such as oral or rectal, administration or parenteral, such as injectable or transdermal, administration to mammals such as humans, comprising a therapeutically effective amount of the pharmacologically active agents, alone or in combination with one or more pharmaceutically acceptable excipients, especially suitable for enteral or parenteral application. Additionally, other routes of administration are also contemplated such as buccal, sublingual, intraurethral, intravaginal, nasal and ocular as well as other routes and methods of delivery known to a person of ordinary skill in the art for delivering a pharmaceutical composition to a mammal, such as a human.

Pharmaceutical compositions for enteral or parenteral administration, in particular those suitable for oral administration, are preferred and comprise for example unit dosage forms, such as coated tablets, tablets, capsules or suppositories and also ampoules. In addition to immediate release oral formulations, modified release pharmaceutical compositions such as delayed release, extended release, sustained release and any other release profiles which are not typically considered to be immediate release are also contemplated. These are prepared by methods known to those of skill in the art, for example using conventional mixing, granulation, coating, solubilizing or lyophilizing processes. Typical oral formulations include coated tablets, tablets, capsules, syrups, elixirs and suspensions. Capsules may contain the active agents e.g. in form of powders, granules, pellets, beadlets or microtablets. For example, a pharmaceutical composition according to the present disclosure may consist of from about 0.1% to 99%, preferably of from about 1% to about 80%, of the active agents, the balance being pharmaceutically acceptable excipients. Thus, pharmaceutical compositions for oral use can be obtained by combining the active compounds with excipients, if desired granulating a mixture which has been obtained, and, if required or necessary, processing the mixture or granulate into tablets or coated tablet cores after having added suitable auxiliary substances. Typical injectable formulations include solutions and suspensions. Typical transdermal administration forms comprise e.g. patches, gels, ointments and the like.

The pharmaceutically acceptable excipients for use in the formulations described above are exemplified by: sugars such as lactose, sucrose, mannitol and sorbitol; starches such as cornstarch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone; polyvinyl alcohol; stearic acid; alkaline earth metal stearates such as magnesium stearate and calcium stearate; stearic acid; vegetable oils such as peanut oil, cottonseed oil, sesame oil, olive oil and corn oil; non-ionic, cationic and anionic surfactants; ethylene glycol polymers; betacyclodextrin; fatty alcohols; and hydrolyzed cereal solids, as well as other non-toxic compatible fillers, binders, disintegrants, agents, e.g. talcum; buffers, preservatives, antioxidants, lubricants, flavoring and the like useful in preparing pharmaceutical formulations. Other suitable excipients can be found in the *Handbook of Pharmaceutical Excipients*, 5th edition which is hereby incorporated by reference in its entirety.

Example 1

Capsules Comprising a $K_{ATP}$ Channel Modulator and a $CB_x$ Modulator

| | |
|---|---|
| 4-Chloro-N-{[3-(4-chloro-phenyl)-4-phenyl-4,5-dihydro-pyrazol-1-yl]-methylamino-methylene}-benzenesulfonamide | 50 mg |
| 3-(1,1-dimethyl-butyl)-6,6,9-trimethyl-6a,7,10,10a-tetrahydro-6H-benzo[c]chromene (JW133) | 50 mg |
| Corn Starch | 150 mg |
| Lactose | 150 mg |
| Ethyl acetate | q.s. |

Example 2

Capsules Comprising a $K_{ATP}$ Channel Modulator and a $CB_x$ Modulator

| | |
|---|---|
| N-{Amino-[3-(4-chloro-phenyl)-4-phenyl-4,5-dihydro-pyrazol-1-yl]-methylene}-4-chloro-benzenesulfonamide | 50 mg |
| 3-(1,1-dimethyl-butyl)-6,6,9-trimethyl-6a,7,10,10a-tetrahydro-6H-benzo[c]chromene (JW133) | 50 mg |
| Corn Starch | 150 mg |
| Lactose | 150 mg |
| Ethyl acetate | q.s. |

Example 3

Capsules Comprising a $K_{ATP}$ Channel Modulator and a $CB_x$ Modulator

| | |
|---|---|
| N-{[3-(4-Chloro-phenyl)-4-pyridin-3-yl-4,5-dihydro-pyrazol-1-yl]-methylamino-methylene}-4-trifluoromethyl-benzenesulfonamide | 50 mg |
| 3-(1,1-dimethyl-butyl)-6,6,9-trimethyl-6a,7,10,10a-tetrahydro-6H-benzo[c]chromene (JW133) | 50 mg |
| Corn Starch | 150 mg |
| Lactose | 150 mg |
| Ethyl acetate | q.s. |

Example 4

Capsules Comprising a $K_{ATP}$ Channel Modulator and a $CB_x$ Modulator

| | |
|---|---|
| 4-Chloro-N-{[3-(4-chloro-phenyl)-4-pyridin-3-yl-4,5-dihydro-pyrazol-1-yl]-methylamino-methylene}-benzenesulfonamide | 50 mg |
| 3-(1,1-dimethyl-butyl)-6,6,9-trimethyl-6a,7,10,10a-tetrahydro-6H-benzo[c]chromene (JW133) | 50 mg |
| Corn Starch | 150 mg |
| Lactose | 150 mg |
| Ethyl acetate | q.s. |

Example 5

Capsules Comprising a K$_{ATP}$ Channel Modulator and a CB$_x$ Modulator

| | |
|---|---|
| 4-Chloro-N-{[3-(4-chloro-phenyl)-4-pyridin-3-yl-4,5-dihydro-pyrazol-1-yl]-methylamino-methylene}-benzenesulfonamide | 50 mg |
| 3-(1,1-dimethyl-butyl)-6,6,9-trimethyl-6a,7,10,10a-tetrahydro-6H-benzo[c]chromene (JW133) | 50 mg |
| Corn Starch | 150 mg |
| Lactose | 150 mg |
| Ethyl acetate | q.s. |

Example 6

Capsules Comprising a K$_{ATP}$ Channel Modulator and a CB$_x$ Modulator

| | |
|---|---|
| 4-Chloro-N-{[3-(4-chloro-phenyl)-4-(3-fluoro-phenyl)-4,5-dihydro-pyrazol-1-yl]-methoxyamino-methylene}-benzenesulfonamide | 50 mg |
| N-Adamantyl-4-pentyl-5-phenyl-thiazole-2-carboxamide | 50 mg |
| Corn Starch | 150 mg |
| Lactose | 150 mg |
| Ethyl acetate | q.s. |

Example 7

Capsules Comprising a K$_{ATP}$ Channel Modulator and a CB$_x$ Modulator

| | |
|---|---|
| 4-Chloro-N-{[3-(4-chloro-phenyl)-4-(3-fluoro-phenyl)-4,5-dihydro-pyrazol-1-yl]-methoxyamino-methylene}-benzenesulfonamide | 50 mg |
| N-Adamantyl-4-pentyl-5-phenyl-thiazole-2-carboxamide | 50 mg |
| Corn Starch | 150 mg |
| Lactose | 150 mg |
| Ethyl acetate | q.s. |

Example 8

Capsules Comprising a K$_{ATP}$ Channel Modulator and a CB$_x$ Modulator

| | |
|---|---|
| 4-Chloro-N-{[3-(4-chloro-phenyl)-4-(3-fluoro-phenyl)-4,5-dihydro-pyrazol-1-yl]-methoxyamino-methylene}-benzenesulfonamide | 50 mg |
| N-Adamantyl-4-pentyl-5-phenyl-thiazole-2-carboxamide | 50 mg |
| Corn Starch | 150 mg |
| Lactose | 150 mg |
| Ethyl acetate | q.s. |

Example 9

Capsules Comprising a K$_{ATP}$ Channel Modulator and a CB$_x$ Modulator

| | |
|---|---|
| Morpholine-4-sulfonic acid [3-(4-chloro-phenyl)-4-phenyl-4,5-dihydro-pyrazol-1-yl]-methylamino-methyleneamide | 50 mg |
| N-Adamantyl-4-pentyl-5-phenyl-thiazole-2-carboxamide | 50 mg |
| Corn Starch | 150 mg |
| Lactose | 150 mg |
| Ethyl acetate | q.s. |

Example 10

Capsules Comprising a K$_{ATP}$ Channel Modulator and a CB$_x$ Modulator

| | |
|---|---|
| N-{[3-(4-Chloro-phenyl)-4-(3-fluoro-phenyl)-4,5-dihydro-pyrazol-1-yl]-methylamino-methylene}-N,N-dimethyl-sulfonamide | 50 mg |
| N-Adamantyl-4-pentyl-5-phenyl-thiazole-2-carboxamide | 50 mg |
| Corn Starch | 150 mg |
| Lactose | 150 mg |
| Ethyl acetate | q.s. |

Example 11

Capsules Comprising a K$_{ATP}$ Channel Modulator and a CB$_x$ Modulator

| | |
|---|---|
| Azepane-1-sulfonic acid [3-(4-chloro-phenyl)-4-phenyl-4,5-dihydro-pyrazol-1-yl]-methylamino-methyleneamide | 50 mg |
| N-{1,3,3-Trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide (SR-144528) | 50 mg |
| Corn Starch | 150 mg |
| Lactose | 150 mg |
| Ethyl acetate | q.s. |

Example 12

Capsules Comprising a K$_{ATP}$ Channel Modulator and a CB$_x$ Modulator

| | |
|---|---|
| 4-Chloro-N-{[3-(4-chloro-phenyl)-4-phenyl-4,5-dihydro-pyrazol-1-yl]-[(1-methyl-pyrrolidin-3-ylmethyl)-amino]-methylene}-benzenesulfonamide | 50 mg |
| N-{1,3,3-Trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide (SR-144528) | 50 mg |
| Corn Starch | 150 mg |
| Lactose | 150 mg |
| Ethyl acetate | q.s. |

Example 13

Capsules Comprising a K$_{ATP}$ Channel Modulator and a CB$_x$ Modulator

| | |
|---|---|
| 1-(4-Chloro-phenyl)-5-phenyl-4,5-dihydro-1H-pyrazole-3-carboxamidine | 50 mg |
| N-{1,3,3-Trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide (SR-144528) | 50 mg |
| Corn Starch | 150 mg |
| Lactose | 150 mg |
| Ethyl acetate | q.s. |

Example 14

Capsules Comprising a K$_{ATP}$ Channel Modulator and a CB$_x$ Modulator

| | |
|---|---|
| N-{[3-(4-Chloro-phenyl)-4-phenyl-4,5-dihydro-pyrazol-1-yl]-methylamino-methylene}-4-trifluoromethyl-benzene-sulfonamide | 50 mg |
| N-{1,3,3-Trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide (SR-144528) | 50 mg |
| Corn Starch | 150 mg |
| Lactose | 150 mg |
| Ethyl acetate | q.s. |

Example 15

Capsules Comprising a K$_{ATP}$ Channel Modulator and a CB$_x$ Modulator

| | |
|---|---|
| Piperidine-1-sulfonic acid [3-(4-chloro-phenyl)-4-phenyl-4,5-dihydro-pyrazol-1-yl]-methylamino-methyleneamide | 50 mg |
| N-{1,3,3-Trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide (SR-144528) | 50 mg |
| Corn Starch | 150 mg |
| Lactose | 150 mg |
| Ethyl acetate | q.s. |

Example 16

Capsules Comprising a K$_{ATP}$ Channel Modulator and a CB$_x$ Modulator

| | |
|---|---|
| Piperidine-1-sulfonic acid [3-(4-chloro-phenyl)-4-phenyl-4,5-dihydro-pyrazol-1-yl]-(2-dimethylamino-ethylamino)-methyleneamide | 50 mg |
| (2-Iodo-5-nitro-phenyl)-[1-(1-methyl-piperidin-2-ylmethyl)-1H-indol-3-yl]-methanone (AM-1241) | 50 mg |
| Corn Starch | 150 mg |
| Lactose | 150 mg |
| Ethyl acetate | q.s. |

Example 17

Capsules Comprising a K$_{ATP}$ Channel Modulator and a CB$_x$ Modulator

| | |
|---|---|
| N,N-Diethylamino-1-sulfonic acid [3-(4-chloro-phenyl)-4-phenyl-4,5-dihydro-pyrazol-1-yl]-methylsulfanyl-methyleneamide | 50 mg |
| (2-Iodo-5-nitro-phenyl)-[1-(1-methyl-piperidin-2-ylmethyl)-1H-indol-3-yl]-methanone (AM-1241) | 50 mg |
| Corn Starch | 150 mg |
| Lactose | 150 mg |
| Ethyl acetate | q.s. |

Example 18

Capsules Comprising a K$_{ATP}$ Channel Modulator and a CB$_x$ Modulator

| | |
|---|---|
| 2-Amino-1-[3-(4-chloro-phenyl)-4-phenyl-4,5-dihydro-pyrazol-1-yl]-3-(3,4-dichloro-phenyl)-propan-1-one | 50 mg |
| (2-Iodo-5-nitro-phenyl)-[1-(1-methyl-piperidin-2-ylmethyl)-1H-indol-3-yl]-methanone (AM-1241) | 50 mg |
| Corn Starch | 150 mg |
| Lactose | 150 mg |
| Ethyl acetate | q.s. |

Example 19

Capsules Comprising a K$_{ATP}$ Channel Modulator and a CB$_x$ Modulator

| | |
|---|---|
| Morpholine-4-sulfonic acid [3-(4-chloro-phenyl)-4-phenyl-4,5-dihydro-pyrazol-1-yl]-methylamino-methyleneamide | 50 mg |
| (2-Iodo-5-nitro-phenyl)-[1-(1-methyl-piperidin-2-ylmethyl)-1H-indol-3-yl]-methanone (AM-1241) | 50 mg |
| Corn Starch | 150 mg |
| Lactose | 150 mg |
| Ethyl acetate | q.s. |

Example 20

Capsules Comprising a K$_{ATP}$ Channel Modulator and a CB$_x$ Modulator

| | |
|---|---|
| N,N-Dimethylamino-1-sulfonic acid [3-(4-chloro-phenyl)-4-phenyl-4,5-dihydro-pyrazol-1-yl]-(2-fluoro-ethylamino)-methyleneamide | 50 mg |
| (2-Iodo-5-nitro-phenyl)-[1-(1-methyl-piperidin-2-ylmethyl)-1H-indol-3-yl]-methanone (AM-1241) | 50 mg |
| Corn Starch | 150 mg |
| Lactose | 150 mg |
| Ethyl acetate | q.s. |

Example 21

Capsules Comprising a K$_{ATP}$ Channel Modulator and a CB$_x$ Modulator

| | |
|---|---|
| Piperidine-1-sulfonic acid [3-(4-chloro-phenyl)-4-(3-fluoro-phenyl)-4,5-dihydro-pyrazol-1-yl]-methylamino-methyleneamide | 50 mg |
| {4-[4-(1,1-Dimethyl-heptyl)-2,6-dimethoxy-phenyl]-6,6-dimethyl-bicyclo[3.1.1]hept-2-en-2-yl}-methanol (HU-308) | 50 mg |
| Corn Starch | 150 mg |
| Lactose | 150 mg |
| Ethyl acetate | q.s. |

Example 22

Capsules Comprising a K$_{ATP}$ Channel Modulator and a CB$_x$ Modulator

| | |
|---|---|
| 5-(4-Chloro-phenyl)-1-(2,4-dichloro-phenyl)-4,5-dihydro-1H-pyrazole-3-carboxylic acid piperidine-1-ylamide | 50 mg |
| {4-[4-(1,1-Dimethyl-heptyl)-2,6-dimethoxy-phenyl]-6,6-dimethyl-bicyclo[3.1.1]hept-2-en-2-yl}-methanol (HU-308) | 50 mg |
| Corn Starch | 150 mg |
| Lactose | 150 mg |
| Ethyl acetate | q.s. |

Example 23

Capsules Comprising a K$_{ATP}$ Channel Modulator and a CB$_x$ Modulator

| | |
|---|---|
| 1-(4-Chloro-phenyl)-5-phenyl-4,5-dihydro-1H-pyrazole-3-carboxylic acid piperidin-1-ylamide | 50 mg |
| {4-[4-(1,1-Dimethyl-heptyl)-2,6-dimethoxy-phenyl]-6,6-dimethyl-bicyclo[3.1.1]hept-2-en-2-yl}-methanol (HU-308) | 50 mg |
| Corn Starch | 150 mg |
| Lactose | 150 mg |
| Ethyl acetate | q.s. |

Example 24

Capsules Comprising a K$_{ATP}$ Channel Modulator and a CB$_x$ Modulator

| | |
|---|---|
| Piperidine-1-sulfonic acid [1-(4-chloro-phenyl)-5-phenyl-4,5-dihydro-1H-pyrazol-3-yl]-methylamino-methyleneamide | 50 mg |
| {4-[4-(1,1-Dimethyl-heptyl)-2,6-dimethoxy-phenyl]-6,6-dimethyl-bicyclo[3.1.1]hept-2-en-2-yl}-methanol (HU-308) | 50 mg |
| Corn Starch | 150 mg |
| Lactose | 150 mg |
| Ethyl acetate | q.s. |

Example 25

Capsules Comprising a K$_{ATP}$ Channel Modulator and a CB$_x$ Modulator

| | |
|---|---|
| Morpholine-4-sulfonic acid [1-(2,4-dichloro-phenyl)-5-phenyl-4,5-dihydro-1H-pyrazol-3-yl]-methylamino-methyleneamide | 50 mg |
| {4-[4-(1,1-Dimethyl-heptyl)-2,6-dimethoxy-phenyl]-6,6-dimethyl-bicyclo[3.1.1]hept-2-en-2-yl}-methanol (HU-308) | 50 mg |
| Corn Starch | 150 mg |
| Lactose | 150 mg |
| Ethyl acetate | q.s. |

Example 26

Capsules Comprising a K$_{ATP}$ Channel Modulator and a CB$_x$ Modulator

| | |
|---|---|
| 4-Chloro-N-[[3-(4-chloro-phenyl)-4-phenyl-4,5-dihydro-pyrazol-1-yl]-(2-fluoro-ethylamino)-methylene]-benzenesulfonamide | 50 mg |
| 3-(1,1-Dimethyl-heptyl)-9-hydroxymethyl-6,6-dimethyl-6a,7,10,10a-tetrahydro-6H-enzo[c]chromen-1-ol (HU-210) | 50 mg |
| Corn Starch | 150 mg |
| Lactose | 150 mg |
| Ethyl acetate | q.s. |

Example 27

Capsules Comprising a K$_{ATP}$ Channel Modulator and a CB$_x$ Modulator

| | |
|---|---|
| 4-Chloro-N-[[3-(4-chloro-phenyl)-4-phenyl-4,5-dihydro-pyrazol-1-yl]-(2-fluoro-ethylamino)-methylene]-benzenesulfonamide | 50 mg |
| 3-(1,1-Dimethyl-heptyl)-9-hydroxymethyl-6,6-dimethyl-6a,7,10,10a-tetrahydro-6H-enzo[c]chromen-1-ol (HU-210) | 50 mg |
| Corn Starch | 150 mg |
| Lactose | 150 mg |
| Ethyl acetate | q.s. |

Example 28

Capsules Comprising a K$_{ATP}$ Channel Modulator and a CB$_x$ Modulator

| | |
|---|---|
| N-{Amino-[3-(4-chloro-phenyl)-4-phenyl-4,5-dihydro-pyrazol-1-yl]-methylene}-4-chloro-benzenesulfonamide | 50 mg |
| 3-(1,1-Dimethyl-heptyl)-9-hydroxymethyl-6,6-dimethyl-6a,7,10,10a-tetrahydro-6H-enzo[c]chromen-1-ol (HU-210) | 50 mg |
| Corn Starch | 150 mg |

-continued

| | |
|---|---|
| Lactose | 150 mg |
| Ethyl acetate | q.s. |

Example 29

Capsules Comprising a $K_{ATP}$ Channel Modulator and a $CB_x$ Modulator

| | |
|---|---|
| 4-Chloro-N-[3-(4-chloro-phenyl)-4-phenyl-4,5-dihydro-pyrazole-1-carbonyl]-benzenesulfonamide | 50 mg |
| 3-(1,1-Dimethyl-heptyl)-9-hydroxymethyl-6,6-dimethyl-6a,7,10,10a-tetrahydro-6H-enzo[c]chromen-1-ol (HU-210) | 50 mg |
| Corn Starch | 150 mg |
| Lactose | 150 mg |
| Ethyl acetate | q.s. |

Example 30

Capsules Comprising a $K_{ATP}$ Channel Modulator and a $CB_x$ Modulator

| | |
|---|---|
| 4-Chloro-N-[[3-(4-chloro-phenyl)-4-phenyl-4,5-dihydro-pyrazol-1-yl]-(2-ethylamino-ethylamino)-methylene]-benzenesulfonamide | 50 mg |
| 3-(1,1-Dimethyl-heptyl)-9-hydroxymethyl-6,6-dimethyl-6a,7,10,10a-tetrahydro-6H-enzo[c]chromen-1-ol (HU-210) | 50 mg |
| Corn Starch | 150 mg |
| Lactose | 150 mg |
| Ethyl acetate | q.s. |

Example 31

Capsules Comprising a $K_{ATP}$ Channel Modulator and a $CB_x$ Modulator

| | |
|---|---|
| 4-Chloro-N-{[3-(4-chloro-phenyl)-4-phenyl-4,5-dihydro-pyrazol-1-yl]-[(1-methyl-pyrrolidin-2-ylmethyl)-amino]-methylene}-benzenesulfonamide | 50 mg |
| Icosa-5,8,11,14-tetraenoic acid 2-hydroxy-1-hydroxymethyl-ethyl ester; 1-Aziridin-1-yl-henicosa-6,9,12,15-tetraen-2-one (2-AG) | 50 mg |
| Corn Starch | 150 mg |
| Lactose | 150 mg |
| Ethyl acetate | q.s. |

Example 32

Capsules Comprising a $K_{ATP}$ Channel Modulator and a $CB_x$ Modulator

| | |
|---|---|
| 4-Chloro-N-[[3-(4-chloro-phenyl)-4-phenyl-4,5-dihydro-pyrazol-1-yl]-(4-pyrrolidin-1-yl-butylamino)-methylene]-benzenesulfonamide | 50 mg |

-continued

| | |
|---|---|
| Icosa-5,8,11,14-tetraenoic acid 2-hydroxy-1-hydroxymethyl-ethyl ester; 1-Aziridin-1-yl-henicosa-6,9,12,15-tetraen-2-one (2-AG) | 50 mg |
| Corn Starch | 150 mg |
| Lactose | 150 mg |
| Ethyl acetate | q.s. |

Example 33

Capsules Comprising a $K_{ATP}$ Channel Modulator and a $CB_x$ Modulator

| | |
|---|---|
| 4-Chloro-N-{[3-(4-chloro-phenyl)-4-phenyl-4,5-dihydro-pyrazol-1-yl]-[(pyridin-3-ylmethyl)-amino]-methylene}-benzenesulfonamide | 50 mg |
| Icosa-5,8,11,14-tetraenoic acid 2-hydroxy-1-hydroxymethyl-ethyl ester; 1-Aziridin-1-yl-henicosa-6,9,12,15-tetraen-2-one (2-AG) | 50 mg |
| Corn Starch | 150 mg |
| Lactose | 150 mg |
| Ethyl acetate | q.s. |

Example 34

Capsules Comprising a $K_{ATP}$ Channel Modulator and a $CB_x$ Modulator

| | |
|---|---|
| 4-Chloro-N-{[3-(4-chloro-phenyl)-4-phenyl-4,5-dihydro-pyrazol-1-yl]-[(pyridin-3-ylmethyl)-amino]-methylene}-benzenesulfonamide | 50 mg |
| Icosa-5,8,11,14-tetraenoic acid 2-hydroxy-1-hydroxymethyl-ethyl ester; 1-Aziridin-1-yl-henicosa-6,9,12,15-tetraen-2-one (2-AG) | 50 mg |
| Corn Starch | 150 mg |
| Lactose | 150 mg |
| Ethyl acetate | q.s. |

Example 35

Capsules Comprising a $K_{ATP}$ Channel Modulator and a $CB_x$ Modulator

| | |
|---|---|
| 1-[3-(4-Chloro-phenyl)-4-phenyl-4,5-dihydro-pyrazol-1-yl]-3-(1H-indol-2-yl)-2-methylamino-propan-1-one | 50 mg |
| Icosa-5,8,11,14-tetraenoic acid 2-hydroxy-1-hydroxymethyl-ethyl ester; 1-Aziridin-1-yl-henicosa-6,9,12,15-tetraen-2-one (2-AG) | 50 mg |
| Corn Starch | 150 mg |
| Lactose | 150 mg |
| Ethyl acetate | q.s. |

Example 36

Capsules Comprising a $K_{ATP}$ Channel Modulator and a $CB_x$ Modulator

| | |
|---|---|
| 2-[3-(4-Chloro-phenyl)-4-phenyl-4,5-dihydro-pyrazol-1-yl]-5-ethyl-4,5-dihydro-oxazole | 50 mg |
| Noladineether | 50 mg |
| Corn Starch | 150 mg |
| Lactose | 150 mg |
| Ethyl acetate | q.s. |

Example 37

Capsules Comprising a $K_{ATP}$ Channel Modulator and a $CB_x$ Modulator

| | |
|---|---|
| 4-Chloro-N-[[3-(4-chloro-phenyl)-4-phenyl-4,5-dihydro-pyrazol-1-yl]-(3-hydroxy-2,2-dimethyl-propylamino)-methylene]-benzenesulfonamide | 50 mg |
| Noladineether | 50 mg |
| Corn Starch | 150 mg |
| Lactose | 150 mg |
| Ethyl acetate | q.s. |

Example 38

Capsules Comprising a $K_{ATP}$ Channel Modulator and a $CB_x$ Modulator

| | |
|---|---|
| N,N-Diethylamino-1-sulfonic acid [3-(4-chloro-phenyl)-4-hydroxy-4-phenyl-4,5-dihydro-pyrazol-1-yl]-methylamino-methyleneamide | 50 mg |
| Noladineether | 50 mg |
| Corn Starch | 150 mg |
| Lactose | 150 mg |
| Ethyl acetate | q.s. |

Example 39

Capsules Comprising a $K_{ATP}$ Channel Modulator and a $CB_x$ Modulator

| | |
|---|---|
| 5-(4-Bromo-phenyl)-1-(2,4-dichloro-phenyl)-1H-pyrazole-3-carbonitrile | 50 mg |
| Noladineether | 50 mg |
| Corn Starch | 150 mg |
| Lactose | 150 mg |
| Ethyl acetate | q.s. |

Example 40

Capsules Comprising a $K_{ATP}$ Channel Modulator and a $CB_x$ Modulator

| | |
|---|---|
| 8-Chloro-1-(2,4-dichloro-phenyl)-1,3a,4,5,6,10b-hexahydro-1,2-diaza-benzo[e]azulene-3-carboxylic acid piperidin-1-ylamide | 50 mg |
| Noladineether | 50 mg |
| Corn Starch | 150 mg |
| Lactose | 150 mg |
| Ethyl acetate | q.s. |

Example 41

Capsules Comprising a $K_{ATP}$ Channel Modulator and a $CB_x$ Modulator

| | |
|---|---|
| 5-(4-Bromo-phenyl)-1-(2,4-dichloro-phenyl)-3-[2-(3,5-difluoro-phenyl)-2-methanesulfonyl-vinyl]-4-methyl-1H-pyrazole | 50 mg |
| 4,4,4-Trifluoro-butane-1-sulfinic acid 3-(2-hydroxymethyl-indan-4-yloxy)-phenyl ester, compound with form aldehyde (BAY-38-7271) | 50 mg |
| Corn Starch | 150 mg |
| Lactose | 150 mg |
| Ethyl acetate | q.s. |

Example 42

Capsules Comprising a $K_{ATP}$ Channel Modulator and a $CB_x$ Modulator

| | |
|---|---|
| Piperidine-1-carboxylic acid [5-(4-chloro-phenyl)-1-(2,4-dichloro-phenyl)-4-methyl-1H-pyrazol-3-yl]-amide | 50 mg |
| 4,4,4-Trifluoro-butane-1-sulfinic acid 3-(2-hydroxymethyl-indan-4-yloxy)-phenyl ester, compound with form aldehyde (BAY-38-7271) | 50 mg |
| Corn Starch | 150 mg |
| Lactose | 150 mg |
| Ethyl acetate | q.s. |

Example 43

Capsules Comprising a $K_{ATP}$ Channel Modulator and a $CB_x$ Modulator

| | |
|---|---|
| 1-(4-Chloro-phenyl)-2-(2,4-dichloro-phenyl)-5-ethylsulfanyl-1H-imidazole-4-carboxylic acid piperidin-1-ylamide | 50 mg |
| 4,4,4-Trifluoro-butane-1-sulfinic acid 3-(2-hydroxymethyl-indan-4-yloxy)-phenyl ester, compound with form aldehyde (BAY-38-7271) | 50 mg |
| Corn Starch | 150 mg |
| Lactose | 150 mg |
| Ethyl acetate | q.s. |

Example 44

Capsules Comprising a $K_{ATP}$ Channel Modulator and a $CB_x$ Modulator

| | |
|---|---|
| 2-(2,4-Dichloro-phenyl)-1-(4-trifluoromethyl-phenyl)-1H-imidazole-4-carboxylic acid piperidin-1-ylamide | 50 mg |
| 4,4,4-Trifluoro-butane-1-sulfinic acid 3-(2-hydroxymethyl-indan-4-yloxy)-phenyl ester, compound with form aldehyde (BAY-38-7271) | 50 mg |
| Corn Starch | 150 mg |
| Lactose | 150 mg |
| Ethyl acetate | q.s. |

Example 45

Capsules Comprising a $K_{ATP}$ Channel Modulator and a $CB_x$ Modulator

| | |
|---|---|
| 2-(2,4-Dichloro-phenyl)-1-(4-trifluoromethyl-phenyl)-1H-imidazole-4-carboxylic acid piperidin-1-ylamide | 50 mg |
| 4,4,4-Trifluoro-butane-1-sulfinic acid 3-(2-hydroxymethyl-indan-4-yloxy)-phenyl ester, compound with form aldehyde (BAY-38-7271) | 50 mg |
| Corn Starch | 150 mg |
| Lactose | 150 mg |
| Ethyl acetate | q.s. |

Example 46

Capsules Comprising a $K_{ATP}$ Channel Modulator and a $CB_x$ Modulator

| | |
|---|---|
| 1-(4-Chloro-phenyl)-2-(2,4-dichloro-phenyl)-5-methylsulfanyl-1H-imidazole-4-carboxylic acid piperidin-1-ylamide | 50 mg |
| 7-Methoxy-2-oxo-8-pentyloxy-1,2-dihydro-quinoline-3-carboxylic acid (benzo[1,3]dioxol-5-ylmethyl)-amide (JTE-907) | 50 mg |
| Corn Starch | 150 mg |
| Lactose | 150 mg |
| Ethyl acetate | q.s. |

Example 47

Capsules Comprising a $K_{ATP}$ Channel Modulator and a $CB_x$ Modulator

| | |
|---|---|
| 1-(4-Chloro-phenyl)-2-(2,4-dichloro-phenyl)-1H-imidazole-4-carboxylic acid piperidin-1-ylamide | 50 mg |
| 7-Methoxy-2-oxo-8-pentyloxy-1,2-dihydro-quinoline-3-carboxylic acid (benzo[1,3]dioxol-5-ylmethyl)-amide (JTE-907) | 50 mg |
| Corn Starch | 150 mg |
| Lactose | 150 mg |
| Ethyl acetate | q.s. |

Example 48

Capsules Comprising a $K_{ATP}$ Channel Modulator and a $CB_x$ Modulator

| | |
|---|---|
| 1-(4-Chloro-phenyl)-2-(2,4-dichloro-phenyl)-5-ethyl-1H-imidazole-4-carboxylic acid piperidin-1-ylamide | 50 mg |
| 7-Methoxy-2-oxo-8-pentyloxy-1,2-dihydro-quinoline-3-carboxylic acid (benzo[1,3]dioxol-5-ylmethyl)-amide (JTE-907) | 50 mg |
| Corn Starch | 150 mg |
| Lactose | 150 mg |
| Ethyl acetate | q.s. |

Example 49

Capsules Comprising a $K_{ATP}$ Channel Modulator and a $CB_x$ Modulator

| | |
|---|---|
| 1-(4-Bromo-phenyl)-2-(2,4-dichloro-phenyl)-5-ethyl-1H-imidazole-4-carboxylic acid piperidin-1-ylamide | 50 mg |
| 7-Methoxy-2-oxo-8-pentyloxy-1,2-dihydro-quinoline-3-carboxylic acid (benzo[1,3]dioxol-5-ylmethyl)-amide (JTE-907) | 50 mg |
| Corn Starch | 150 mg |
| Lactose | 150 mg |
| Ethyl acetate | q.s. |

Example 50

Capsules Comprising a $K_{ATP}$ Channel Modulator and a $CB_x$ Modulator

| | |
|---|---|
| 1-(4-Bromo-phenyl)-5-chloro-2-(2,4-dichloro-phenyl)-1H-imidazole-4-carboxylic acid piperidin-1-ylamide | 50 mg |
| 7-Methoxy-2-oxo-8-pentyloxy-1,2-dihydro-quinoline-3-carboxylic acid (benzo[1,3]dioxol-5-ylmethyl)-amide (JTE-907) | 50 mg |
| Corn Starch | 150 mg |
| Lactose | 150 mg |
| Ethyl acetate | q.s. |

Example 51

Capsules Comprising a $K_{ATP}$ Channel Modulator and a $CB_x$ Modulator

| | |
|---|---|
| 1-(4-Bromo-phenyl)-2-(2,4-dichloro-phenyl)-5-ethyl-1H-imidazole-4-carboxylic acid cyclohexylamide | 50 mg |
| N-(1-{4-[4-Chloro-2-(2-fluoro-benzenesulfonyl)-benzenesulfonyl]-phenyl}-ethyl)-methanesulfonamide (Schering) | 50 mg |
| Corn Starch | 150 mg |
| Lactose | 150 mg |
| Ethyl acetate | q.s. |

Example 52

Capsules Comprising a $K_{ATP}$ Channel Modulator and a $CB_x$ Modulator

| | |
|---|---|
| 1-(4-Bromo-phenyl)-2-(2,4-dichloro-phenyl)-5-ethyl-1H-imidazole-4-carboxylic acid pentylamide | 50 mg |
| N-(1-{4-[4-Chloro-2-(2-fluoro-benzenesulfonyl)-benzenesulfonyl]-phenyl}-ethyl)-methanesulfonamide (Schering) | 50 mg |
| Corn Starch | 150 mg |
| Lactose | 150 mg |
| Ethyl acetate | q.s. |

Example 53

Capsules Comprising a $K_{ATP}$ Channel Modulator and a $CB_x$ Modulator

| | |
|---|---|
| 4-(4-Chloro-phenyl)-5-(2,4-dichloro-phenyl)-1-methyl-1H-imidazole-2-carboxylic acid cyclohexylamide | 50 mg |
| N-(1-{4-[4-Chloro-2-(2-fluoro-benzenesulfonyl)-benzenesulfonyl]-phenyl}-ethyl)-methanesulfonamide (Schering) | 50 mg |
| Corn Starch | 150 mg |
| Lactose | 150 mg |
| Ethyl acetate | q.s. |

Example 54

Capsules Comprising a $K_{ATP}$ Channel Modulator and a $CB_x$ Modulator

| | |
|---|---|
| 4-(4-Chloro-phenyl)-5-(2,4-dichloro-phenyl)-3-methyl-1H-imidazole-2-carboxylic acid cyclohexylamide | 50 mg |
| N-(1-{4-[4-Chloro-2-(2-fluoro-benzenesulfonyl)-benzenesulfonyl]-phenyl}-ethyl)-methanesulfonamide (Schering) | 50 mg |
| Corn Starch | 150 mg |
| Lactose | 150 mg |
| Ethyl acetate | q.s. |

Example 55

Capsules Comprising a $K_{ATP}$ Channel Modulator and a $CB_x$ Modulator

| | |
|---|---|
| 4-(4-Chloro-phenyl)-5-(2,4-dichloro-phenyl)-3-methyl-1H-imidazole-2-carboxylic acid cyclohexylamide | 50 mg |
| N-(1-{4-[4-Chloro-2-(2-fluoro-benzenesulfonyl)-benzenesulfonyl]-phenyl}-ethyl)-methanesulfonamide (Schering) | 50 mg |
| Corn Starch | 150 mg |
| Lactose | 150 mg |
| Ethyl acetate | q.s. |

Example 56

Capsules Comprising a $K_{ATP}$ Channel Modulator and a $CB_x$ Modulator

| | |
|---|---|
| 1-(5-Chloro-pyridin-2-yl)-2-(2,4-dichloro-phenyl)-5-ethyl-1H-imidazole-4-carboxylic acid piperidin-1-ylamide | 50 mg |
| [6-Iodo-2-methyl-1-(2-morpholin-4-yl-ethyl)-2,3-dihydro-1H-indol-3-yl]-(4-methoxy-phenyl)-methanone (AM-630) | 50 mg |
| Corn Starch | 150 mg |
| Lactose | 150 mg |
| Ethyl acetate | q.s. |

Example 57

Capsules Comprising a $K_{ATP}$ Channel Modulator and a $CB_x$ Modulator

| | |
|---|---|
| 1-(4-Chloro-phenyl)-2-(2,4-dichloro-phenyl)-5-methyl-1H-imidazole-4-carboxylic acid (4-hydroxy-cyclo-hexyl)-amide | 50 mg |
| [6-Iodo-2-methyl-1-(2-morpholin-4-yl-ethyl)-2,3-dihydro-1H-indol-3-yl]-(4-methoxy-phenyl)-methanone (AM-630) | 50 mg |
| Corn Starch | 150 mg |
| Lactose | 150 mg |
| Ethyl acetate | q.s. |

Example 58

Capsules Comprising a $K_{ATP}$ Channel Modulator and a $CB_x$ Modulator

| | |
|---|---|
| 1-(4-Chloro-phenyl)-2-(2,4-dichloro-phenyl)-5-methyl-1H-imidazole-4-carboxylic acid azepan-1-ylamide | 50 mg |
| [6-Iodo-2-methyl-1-(2-morpholin-4-yl-ethyl)-2,3-dihydro-1H-indol-3-yl]-(4-methoxy-phenyl)-methanone (AM-630) | 50 mg |
| Corn Starch | 150 mg |
| Lactose | 150 mg |
| Ethyl acetate | q.s. |

Example 59

Capsules Comprising a $K_{ATP}$ Channel Modulator and a $CB_x$ Modulator

| | |
|---|---|
| 2-(2,4-Dichloro-phenyl)-5-ethyl-1-phenyl-1H-imidazole-4-carboxylic acid piperidin-1-ylamide | 50 mg |
| [6-Iodo-2-methyl-1-(2-morpholin-4-yl-ethyl)-2,3-dihydro-1H-indol-3-yl]-(4-methoxy-phenyl)-methanone (AM-630) | 50 mg |
| Corn Starch | 150 mg |
| Lactose | 150 mg |
| Ethyl acetate | q.s. |

Example 60

Capsules Comprising a $K_{ATP}$ Channel Modulator and a $CB_x$ Modulator

| | |
|---|---|
| 2-(1,5-Dimethyl-1H-pyrrol-2-yl)-5-ethyl-1-phenyl-1H-imidazole-4-carboxylic acid cyclohexylamide | 50 mg |
| [6-Iodo-2-methyl-1-(2-morpholin-4-yl-ethyl)-2,3-dihydro-1H-indol-3-yl]-(4-methoxy-phenyl)-methanone (AM-630) | 50 mg |
| Corn Starch | 150 mg |
| Lactose | 150 mg |
| Ethyl acetate | q.s. |

Example 61

Capsules Comprising a $K_{ATP}$ Channel Modulator and a $CB_x$ Modulator

| | |
|---|---|
| 1-(4-Chloro-phenyl)-5-ethyl-2-(3-methyl-pyridin-2-yl)-1H-imidazole-4-carboxylic acid piperidin-1-ylamide | 50 mg |
| 1-(4-Chloro-phenyl)-2-(2-chloro-phenyl)-5-ethyl-1H-imidazole-4-carboxylic acid piperidin-1-ylamide (Bayer) | 50 mg |
| Corn Starch | 150 mg |
| Lactose | 150 mg |
| Ethyl acetate | q.s. |

Example 62

Capsules Comprising a $K_{ATP}$ Channel Modulator and a $CB_x$ Modulator

| | |
|---|---|
| 1-(4-Chloro-phenyl)-2-(2,4-dichloro-phenyl)-5-ethyl-1H-imidazole-4-carboxylic acid piperidin-1-ylamide | 50 mg |
| 1-(4-Chloro-phenyl)-2-(2-chloro-phenyl)-5-ethyl-1H-imidazole-4-carboxylic acid piperidin-1-ylamide (Bayer) | 50 mg |
| Corn Starch | 150 mg |
| Lactose | 150 mg |
| Ethyl acetate | q.s. |

Example 63

Capsules Comprising a $K_{ATP}$ Channel Modulator and a $CB_x$ Modulator

| | |
|---|---|
| 1-(4-Bromo-phenyl)-2-(2,4-dichloro-phenyl)-5-ethyl-1H-imidazole-4-carboxylic acid piperidin-1-ylamide | 50 mg |
| 1-(4-Chloro-phenyl)-2-(2-chloro-phenyl)-5-ethyl-1H-imidazole-4-carboxylic acid piperidin-1-ylamide (Bayer) | 50 mg |
| Corn Starch | 150 mg |
| Lactose | 150 mg |
| Ethyl acetate | q.s. |

Example 64

Capsules Comprising a $K_{ATP}$ Channel Modulator and a $CB_x$ Modulator

| | |
|---|---|
| 1-(4-Bromo-phenyl)-5-chloro-2-(2,4-dichloro-phenyl)-1H-imidazole-4-carboxylic acid piperidin-1-ylamide | 50 mg |
| 1-(4-Chloro-phenyl)-2-(2-chloro-phenyl)-5-ethyl-1H-imidazole-4-carboxylic acid piperidin-1-ylamide (Bayer) | 50 mg |
| Corn Starch | 50 mg |
| Lactose | 150 mg |
| Ethyl acetate | q.s. |

Example 65

Capsules Comprising a $K_{ATP}$ Channel Modulator and a $CB_x$ Modulator

| | |
|---|---|
| 1-(4-Bromo-phenyl)-2-(2,4-dichloro-phenyl)-5-ethyl-1H-imidazole-4-carboxylic acid cyclohexylamide | 50 mg |
| 1-(4-Chloro-phenyl)-2-(2-chloro-phenyl)-5-ethyl-1H-imidazole-4-carboxylic acid piperidin-1-ylamide (Bayer) | 50 mg |
| Corn Starch | 150 mg |
| Lactose | 150 mg |
| Ethyl acetate | .s. |

Example 66

Capsules Comprising a $K_{ATP}$ Channel Modulator and a $CB_x$ Modulator

| | |
|---|---|
| 1-(4-Bromo-phenyl)-2-(2,4-dichloro-phenyl)-5-ethyl-1H-imidazole-4-carboxylic acid pentylamide | 50 mg |
| (2-Methyl-1-propyl-2,3-dihydro-1H-indol-3-yl)-naphthalen-1-yl-methanone (JWH-015) | 50 mg |
| Corn Starch | 150 mg |
| Lactose | 150 mg |
| Ethyl acetate | q.s. |

Example 67

Capsules Comprising a $K_{ATP}$ Channel Modulator and a $CB_x$ Modulator

| | |
|---|---|
| 4-(4-Chloro-phenyl)-5-(2,4-dichloro-phenyl)-1-methyl-1H-imidazole-2-carboxylic acid cyclohexylamide | 50 mg |
| (2-Methyl-1-propyl-2,3-dihydro-1H-indol-3-yl)-naphthalen-1-yl-methanone (JWH-015) | 50 mg |
| Corn Starch | 150 mg |
| Lactose | 150 mg |
| Ethyl acetate | q.s. |

Example 68

Capsules Comprising a $K_{ATP}$ Channel Modulator and a $CB_x$ Modulator

| | |
|---|---:|
| 4-(4-Chloro-phenyl)-5-(2,4-dichloro-phenyl)-3-methyl-1H-imidazole-2-carboxylic acid cyclohexylamide | 50 mg |
| (2-Methyl-1-propyl-2,3-dihydro-1H-indol-3-yl)-naphthalen-1-yl-methanone (JWH-015) | 50 mg |
| Corn Starch | 150 mg |
| Lactose | 150 mg |
| Ethyl acetate | q.s. |

Example 69

Capsules Comprising a $K_{ATP}$ Channel Modulator and a $CB_x$ Modulator

| | |
|---|---:|
| 1-(5-Chloro-pyridin-2-yl)-2-(2,4-dichloro-phenyl)-5-ethyl-1H-imidazole-4-carboxylic acid piperidin-1-ylamide | 50 mg |
| (2-Methyl-1-propyl-2,3-dihydro-1H-indol-3-yl)-naphthalen-1-yl-methanone (JWH-015) | 50 mg |
| Corn Starch | 150 mg |
| Lactose | 150 mg |
| Ethyl acetate | q.s. |

Example 70

Capsules Comprising a $K_{ATP}$ Channel Modulator and a $CB_x$ Modulator

| | |
|---|---:|
| 1-(5-Chloro-pyridin-2-yl)-2-(2,4-dichloro-phenyl)-5-ethyl-1H-imidazole-4-carboxylic acid piperidin-1-ylamide | 50 mg |
| (2-Methyl-1-propyl-2,3-dihydro-1H-indol-3-yl)-naphthalen-1-yl-methanone (JWH-015) | 50 mg |
| Corn Starch | 150 mg |
| Lactose | 150 mg |
| Ethyl acetate | q.s. |

Example 71

Capsules Comprising a $K_{ATP}$ Channel Modulator and a $CB_x$ Modulator

| | |
|---|---:|
| 1-(4-Chloro-phenyl)-2-(2,4-dichloro-phenyl)-5-methyl-1H-imidazole-4-carboxylic acid (4-hydroxy-cyclo-hexyl)-amide | 50 mg |
| 5-(1,1-Dimethyl-heptyl)-2-[5-hydroxy-2-(3-hydroxy-propyl)-cyclohexyl]-phenol (CP55940) | 50 mg |
| Corn Starch | 150 mg |
| Lactose | 50 mg |
| Ethyl acetate | q.s. |

Example 72

Capsules Comprising a $K_{ATP}$ Channel Modulator and a $CB_x$ Modulator

| | |
|---|---:|
| 1-(4-Chloro-phenyl)-2-(2,4-dichloro-phenyl)-5-methyl-1H-imidazole-4-carboxylic acid azepan-1-ylamide | 50 mg |
| 5-(1,1-Dimethyl-heptyl)-2-[5-hydroxy-2-(3-hydroxy-propyl)-cyclohexyl]-phenol (CP55940) | 50 mg |
| Corn Starch | 150 mg |
| Lactose | 150 mg |
| Ethyl acetate | q.s. |

Example 73

Capsules Comprising a $K_{ATP}$ Channel Modulator and a $CB_x$ Modulator

| | |
|---|---:|
| 2-(2,4-Dichloro-phenyl)-5-ethyl-1-phenyl-1H-imidazole-4-carboxylic acid piperidin-1-ylamide | 50 mg |
| 5-(1,1-Dimethyl-heptyl)-2-[5-hydroxy-2-(3-hydroxy-propyl)-cyclohexyl]-phenol (CP55940) | 50 mg |
| Corn Starch | 150 mg |
| Lactose | 150 mg |
| Ethyl acetate | q.s. |

Example 74

Capsules Comprising a $K_{ATP}$ Channel Modulator and a $CB_x$ Modulator

| | |
|---|---:|
| 2-(1,5-Dimethyl-1H-pyrrol-2-yl)-5-ethyl-1-phenyl-1H-imidazole-4-carboxylic acid cyclohexylamide | 50 mg |
| 5-(1,1-Dimethyl-heptyl)-2-[5-hydroxy-2-(3-hydroxy-propyl)-cyclohexyl]-phenol (CP55940) | 50 mg |
| Corn Starch | 150 mg |
| Lactose | 150 mg |
| Ethyl acetate | q.s. |

Example 75

Capsules Comprising a $K_{ATP}$ Channel Modulator and a $CB_x$ Modulator

| | |
|---|---:|
| 1-(4-Chloro-phenyl)-5-ethyl-2-(3-methyl-pyridin-2-yl)-1H-imidazole-4-carboxylic acid piperidin-1-ylamide | 50 mg |
| 5-(1,1-Dimethyl-heptyl)-2-[5-hydroxy-2-(3-hydroxy-propyl)-cyclohexyl]-phenol (CP55940) | 50 mg |
| Corn Starch | 150 mg |
| Lactose | 150 mg |
| Ethyl acetate | q.s. |

Example 76

Capsules Comprising a $K_{ATP}$ Channel Modulator and a $CB_x$ Modulator

| | |
|---|---|
| 1-(4-Chloro-phenyl)-5-ethyl-2-(3-methyl-pyridin-2-yl)-1H-imidazole-4-carboxylic acid cyclohexylamide | 50 mg |
| (2-Methyl-3-morpholin-4-ylmethyl-3,4-dihydro-5-oxa-2a-azacenaphthylen-1-yl)-naphthalen-1-yl-methanone (WIN55212-2) | 50 mg |
| Corn Starch | 150 mg |
| Lactose | 150 mg |
| Ethyl acetate | q.s. |

Example 77

Capsules Comprising a $K_{ATP}$ Channel Modulator and a $CB_x$ Modulator

| | |
|---|---|
| 1-(4-Chloro-phenyl)-2-(2,4-dichloro-phenyl)-5-methyl-1H-imidazole-4-carboxylic acid (4-trifluoromethyl-phenyl)-amide | 50 mg |
| (2-Methyl-3-morpholin-4-ylmethyl-3,4-dihydro-5-oxa-2a-azacenaphthylen-1-yl)-naphthalen-1-yl-methanone (WIN55212-2) | 50 mg |
| Corn Starch | 150 mg |
| Lactose | 150 mg |
| Ethyl acetate | q.s. |

Example 78

Capsules Comprising a $K_{ATP}$ Channel Modulator and a $CB_x$ Modulator

| | |
|---|---|
| 2-(2,4-Dichloro-phenyl)-5-methyl-1-pyridin-2-yl-1H-imidazole-4-carboxylic acid piperidin-1-ylamide | 50 mg |
| (2-Methyl-3-morpholin-4-ylmethyl-3,4-dihydro-5-oxa-2a-azacenaphthylen-1-yl)-naphthalen-1-yl-methanone (WIN55212-2) | 50 mg |
| Corn Starch | 150 mg |
| Lactose | 150 mg |
| Ethyl acetate | q.s. |

Example 79

Capsules Comprising a $K_{ATP}$ Channel Modulator and a $CB_x$ Modulator

| | |
|---|---|
| 1-(4-Chloro-phenyl)-2-(2,4-dichloro-phenyl)-5-fluoromethyl-1H-imidazole-4-carboxylic acid piperidin-1-ylamide | 50 mg |
| (2-Methyl-3-morpholin-4-ylmethyl-3,4-dihydro-5-oxa-2a-azacenaphthylen-1-yl)-naphthalen-1-yl-methanone (WIN55212-2) | 50 mg |
| Corn Starch | 150 mg |
| Lactose | 150 mg |
| Ethyl acetate | q.s. |

Example 80

Capsules Comprising a $K_{ATP}$ Channel Modulator and a $CB_x$ Modulator

| | |
|---|---|
| 1-(4-Chloro-phenyl)-2-(2,4-dichloro-phenyl)-5-hydroxymethyl-1H-imidazole-4-carboxylic acid piperidin-1-ylamide | 50 mg |
| (2-Methyl-3-morpholin-4-ylmethyl-3,4-dihydro-5-oxa-2a-azacenaphthylen-1-yl)-naphthalen-1-yl-methanone (WIN55212-2) | 50 mg |
| Corn Starch | 150 mg |
| Lactose | 150 mg |
| Ethyl acetate | q.s. |

Example 81

Capsules Comprising a $K_{ATP}$ Channel Modulator and a $CB_x$ Modulator

| | |
|---|---|
| 1-(4-Chloro-phenyl)-2-(2,4-dichloro-phenyl)-5-methylsulfanyl-1H-imidazole-4-carboxylic acid cyclohexylamide | 50 mg |
| 5-(4-Chloro-phenyl)-1-(2,4-dichloro-phenyl)-4-methyl-1H-pyrazole-3-carboxylic acid piperidin-1-ylamide (Rimonabant) | 50 mg |
| Corn Starch | 150 mg |
| Lactose | 150 mg |
| Ethyl acetate | q.s. |

Example 82

Capsules Comprising a $K_{ATP}$ Channel Modulator and a $CB_x$ Modulator

| | |
|---|---|
| 1-(4-Chloro-phenyl)-2-(2,4-dichloro-phenyl)-5-methanesulfonyl-1H-imidazole-4-carboxylic acid piperidin-1-ylamide | 50 mg |
| 5-(4-Chloro-phenyl)-1-(2,4-dichloro-phenyl)-4-methyl-1H-pyrazole-3-carboxylic acid piperidin-1-ylamide (Rimonabant) | 50 mg |
| Corn Starch | 150 mg |
| Lactose | 150 mg |
| Ethyl acetate | q.s. |

Example 83

Capsules Comprising a $K_{ATP}$ Channel Modulator and a $CB_x$ Modulator

| | |
|---|---|
| 1-(4-Chloro-phenyl)-2-(2,4-dichloro-phenyl)-5-methanesulfinyl-1H-imidazole-4-carboxylic acid piperidin-1-ylamide | 50 mg |
| 5-(4-Chloro-phenyl)-1-(2,4-dichloro-phenyl)-4-methyl-1H-pyrazole-3-carboxylic acid piperidin-1-ylamide (Rimonabant) | 50 mg |
| Corn Starch | 150 mg |

-continued

| | |
|---|---|
| Lactose | 150 mg |
| Ethyl acetate | q.s. |

Example 84

Capsules Comprising a $K_{ATP}$ Channel Modulator and a $CB_x$ Modulator

| | |
|---|---|
| 5-(4-Chloro-phenyl)-4-(2,5-dichloro-phenyl)-1-methyl-1H-imidazole-2-carboxylic acid piperidin-1-ylamide | 50 mg |
| 5-(4-Chloro-phenyl)-1-(2,4-dichloro-phenyl)-4-methyl-1H-pyrazole-3-carboxylic acid piperidin-1-ylamide (Rimonabant) | 50 mg |
| Corn Starch | 150 mg |
| Lactose | 150 mg |
| Ethyl acetate | q.s. |

Example 85

Capsules Comprising a $K_{ATP}$ Channel Modulator and a $CB_x$ Modulator

| | |
|---|---|
| 2-(2-Chloro-phenyl)-1-(5-chloro-pyridin-2-yl)-5-ethyl-1H-imidazole-4-carboxylic acid piperidin-1-ylamide | 50 mg |
| 5-(4-Chloro-phenyl)-1-(2,4-dichloro-phenyl)-4-methyl-1H-pyrazole-3-carboxylic acid piperidin-1-ylamide (Rimonabant) | 50 mg |
| Corn Starch | 150 mg |
| Lactose | 150 mg |
| Ethyl acetate | q.s. |

Example 86

Capsules Comprising a $K_{ATP}$ Channel Modulator and a $CB_x$ Modulator

| | |
|---|---|
| 1-(4-Chloro-phenyl)-2-(2,4-dichloro-phenyl)-5-(2,2,2-trifluoro-ethyl)-1H-imidazole-4-carboxylic acid piperidin-1-ylamide | 50 mg |
| 5-(4-Bromo-phenyl)-1-(2,4-dichloro-phenyl)-4-ethyl-1H-pyrazole-3-carboxylic acid piperidin-1-ylamide (SR-147778) | 50 mg |
| Corn Starch | 150 mg |
| Lactose | 150 mg |
| Ethyl acetate | q.s. |

Example 87

Capsules Comprising a $K_{ATP}$ Channel Modulator and a $CB_x$ Modulator

| | |
|---|---|
| N-[1-(4-Chloro-phenyl)-2-(2,4-dichloro-phenyl)-5-methyl-1H-imidazol-4-yl]-benzamide | 50 mg |
| 5-(4-Bromo-phenyl)-1-(2,4-dichloro-phenyl)-4-ethyl-1H-pyrazole-3-carboxylic acid piperidin-1-ylamide (SR-147778) | 50 mg |
| Corn Starch | 150 mg |
| Lactose | 150 mg |
| Ethyl acetate | q.s. |

Example 88

Capsules Comprising a $K_{ATP}$ Channel Modulator and a $CB_x$ Modulator

| | |
|---|---|
| 1-(4-Chloro-phenyl)-2-(2,4-dichloro-phenyl)-5-pyrrolidin-1-ylmethyl-1H-imidazole-4-carboxylic acid piperidin-1-ylamide | 50 mg |
| 5-(4-Bromo-phenyl)-1-(2,4-dichloro-phenyl)-4-ethyl-1H-pyrazole-3-carboxylic acid piperidin-1-ylamide (SR-147778) | 50 mg |
| Corn Starch | 150 mg |
| Lactose | 150 mg |
| Ethyl acetate | q.s. |

Example 89

Capsules Comprising a $K_{ATP}$ Channel Modulator and a $CB_x$ Modulator

| | |
|---|---|
| 2-[1-(4-Chloro-phenyl)-2-(2,4-dichloro-phenyl)-5-methyl-1H-imidazol-4-yl]-hexan-2-ol | 50 mg |
| 5-(4-Bromo-phenyl)-1-(2,4-dichloro-phenyl)-4-ethyl-1H-pyrazole-3-carboxylic acid piperidin-1-ylamide (SR-147778) | 50 mg |
| Corn Starch | 150 mg |
| Lactose | 150 mg |
| Ethyl acetate | q.s. |

Example 90

Capsules Comprising a $K_{ATP}$ Channel Modulator and a $CB_x$ Modulator

| | |
|---|---|
| 1-(4-Chloro-phenyl)-2-(2,4-dichloro-phenyl)-5-methyl-4-pentyl-1H-imidazole | 50 mg |
| 5-(4-Bromo-phenyl)-1-(2,4-dichloro-phenyl)-4-ethyl-1H-pyrazole-3-carboxylic acid piperidin-1-ylamide (SR-147778) | 50 mg |
| Corn Starch | 150 mg |
| Lactose | 150 mg |
| Ethyl acetate | q.s. |

Example 91

Capsules Comprising a $K_{ATP}$ Channel Modulator and a $CB_x$ Modulator

| | |
|---|---|
| 2,5-Dimethyl-1-phenyl-1H-imidazole-4-carboxylic acid adamantan-2-ylamide | 50 mg |
| 1-[Bis-(4-chloro-phenyl)-methyl]-3-[(3,5-difluoro-phenyl)-methanesulfonyl-methylene]-azetidine (Aventis) | 50 mg |
| Corn Starch | 150 mg |
| Lactose | 150 mg |
| Ethyl acetate | q.s. |

Example 92

Capsules Comprising a $K_{ATP}$ Channel Modulator and a $CB_x$ Modulator

| | |
|---|---|
| 1-(4-Chloro-phenyl)-2-(2-chloro-phenyl)-5-methylsulfanyl-1H-imidazole-4-carboxylic acid piperidin-1-ylamide | 50 mg |
| 1-[Bis-(4-chloro-phenyl)-methyl]-3-[(3,5-difluoro-phenyl)-methanesulfonyl-methylene]-azetidine (Aventis) | 50 mg |
| Corn Starch | 150 mg |
| Lactose | 150 mg |
| Ethyl acetate | q.s. |

Example 93

Capsules Comprising a $K_{ATP}$ Channel Modulator and a $CB_x$ Modulator

| | |
|---|---|
| 2-(2-Chloro-phenyl)-1-(4-trifluoromethyl-phenyl)-1H-imidazole-4-carboxylic acid piperidin-1-ylamide | 50 mg |
| 1-[Bis-(4-chloro-phenyl)-methyl]-3-[(3,5-difluoro-phenyl)-methanesulfonyl-methylene]-azetidine (Aventis) | 50 mg |
| Corn Starch | 150 mg |
| Lactose | 150 mg |
| Ethyl acetate | q.s. |

Example 94

Capsules Comprising a $K_{ATP}$ Channel Modulator and a $CB_x$ Modulator

| | |
|---|---|
| 5-(4-Chloro-phenyl)-4-(2,4-dichloro-phenyl)-thiazole-2-carboxylic acid piperidin-1-ylamide | 50 mg |
| 1-[Bis-(4-chloro-phenyl)-methyl]-3-[(3,5-difluoro-phenyl)-methanesulfonyl-methylene]-azetidine (Aventis) | 50 mg |
| Corn Starch | 150 mg |
| Lactose | 150 mg |
| Ethyl acetate | q.s. |

Example 95

Capsules Comprising a $K_{ATP}$ Channel Modulator and a $CB_x$ Modulator

| | |
|---|---|
| 5-(4-Chloro-phenyl)-1-(2,4-dichloro-phenyl)-1H-[1,2,4]triazole-3-carboxylic acid pyrrolidin-1-ylamide | 50 mg |
| 1-[Bis-(4-chloro-phenyl)-methyl]-3-[(3,5-difluoro-phenyl)-methanesulfonyl-methylene]-azetidine (Aventis) | 50 mg |
| Corn Starch | 150 mg |
| Lactose | 150 mg |
| Ethyl acetate | q.s. |

Example 96

Capsules Comprising a $K_{ATP}$ Channel Modulator and a $CB_x$ Modulator

| | |
|---|---|
| 1-(4-Chloro-phenyl)-5-(2,4-dichloro-phenyl)-1H-[1,2,4]triazole-3-carboxylic acid piperidin-1-yl-amide | 50 mg |
| 4-Chloro-N-{[3-(4-chloro-phenyl)-4-phenyl-4,5-dihydro-pyrazol-1-yl]-methylamino-methylene}-benzenesulfonamide | 50 mg |
| Corn Starch | 150 mg |
| Lactose | 150 mg |
| Ethyl acetate | q.s. |

Example 97

Capsules Comprising a $K_{ATP}$ Channel Modulator and a $CB_x$ Modulator

| | |
|---|---|
| 5-Pentyl-4-phenyl-thiazole-2-carboxylic acid (hexahydro-2,5-methano-pentalen-3a-yl)-amide | 50 mg |
| N-{Amino-[3-(4-chloro-phenyl)-4-phenyl-4,5-dihydro-pyrazol-1-yl]-methylene}-4-chloro-benzenesulfonamide | 50 mg |
| Corn Starch | 150 mg |
| Lactose | 150 mg |
| Ethyl acetate | q.s. |

Example 98

Capsules Comprising a $K_{ATP}$ Channel Modulator and a $CB_x$ Modulator

| | |
|---|---|
| 4-Pentyl-5-phenyl-thiazole-2-carboxylic acid (hexahydro-2,5-methano-pentalen-3a-yl)-amide | 50 mg |
| N-{[3-(4-Chloro-phenyl)-4-pyridin-3-yl-4,5-dihydro-pyrazol-1-yl]-methylamino-methylene}-4-trifluoromethyl-benzenesulfonamide | 50 mg |
| Corn Starch | 150 mg |
| Lactose | 150 mg |
| Ethyl acetate | q.s. |

Example 99

Capsules Comprising a $K_{ATP}$ Channel Modulator and a $CB_x$ Modulator

| | |
|---|---|
| 1-{(4-Chloro-benzene-sulfonylimino)-[3-(4-chloro-phenyl)-4-phenyl-4,5-dihydro-pyrazol-1-yl]-methyl}-piperidine-4-carboxylic acid amide | 50 mg |
| 4-Chloro-N-{[3-(4-chloro-phenyl)-4-pyridin-3-yl-4,5-dihydro-pyrazol-1-yl]-methylamino-methylene}-benzenesulfonamide | 50 mg |
| Corn Starch | 150 mg |
| Lactose | 150 mg |
| Ethyl acetate | q.s. |

Example 100

Capsules Comprising a $K_{ATP}$ Channel Modulator and a $CB_x$ Modulator

| | |
|---|---|
| 4-Chloro-N-{[3-(4-chloro-phenyl)-4-phenyl-4,5-dihydro-pyrazol-1-yl]-[2-(2-oxo-pyrrolidin-1-yl)-ethylamino]-methylene}-benzenesulfonamide | 50 mg |
| 4-Chloro-N-{[3-(4-chloro-phenyl)-4-(3-fluoro-phenyl)-4,5-dihydro-pyrazol-1-yl]-methoxyamino-methylene}-benzenesulfonamide | 50 mg |
| Corn Starch | 150 mg |
| Lactose | 150 mg |
| Ethyl acetate | q.s. |

Example 101

Capsules Comprising a $K_{ATP}$ Channel Modulator and a $CB_x$ Modulator

| | |
|---|---|
| 4-Chloro-N-[[3-(4-chloro-phenyl)-4-phenyl-4,5-dihydro-pyrazol-1-yl]-(2-cyano-ethylamino)-methylene]-benzene-sulfonamide | 50 mg |
| N-{[3-(4-Chloro-phenyl)-4-phenyl-4,5-dihydro-pyrazol-1-yl]-methylamino-methylene}-4-trifluoromethyl-benzene-sulfonamide | 50 mg |
| Corn Starch | 150 mg |
| Lactose | 150 mg |
| Ethyl acetate | q.s. |

Example 102

Capsules Comprising a $K_{ATP}$ Channel Modulator and a $CB_x$ Modulator

| | |
|---|---|
| 4-Chloro-N-[[3-(4-chloro-phenyl)-4-phenyl-4,5-dihydro-pyrazol-1-yl]-(methoxy-methyl-amino)-methylene]-benzenesulfonamide | 50 mg |
| 1-(4-Chloro-phenyl)-2-(2,4-dichloro-phenyl)-5-methanesulfinyl-1H-imidazole-4-carboxylic acid piperidin-1-ylamide | 50 mg |
| Corn Starch | 150 mg |
| Lactose | 150 mg |
| Ethyl acetate | q.s. |

Example 103

Capsules Comprising a $K_{ATP}$ Channel Modulator and a $CB_x$ Modulator

| | |
|---|---|
| 4-Chloro-N-{[3-(4-chloro-phenyl)-4-phenyl-4,5-dihydro-pyrazol-1-yl]-[(piperidin-4-ylmethyl)-amino]-methylene}-benzenesulfonamide | 50 mg |
| Morpholine-4-sulfonic acid [3-(4-chloro-phenyl)-4-phenyl-4,5-dihydro-pyrazol-1-yl]-methylamino-methyleneamide | 50 mg |
| Corn Starch | 150 mg |
| Lactose | 150 mg |
| Ethyl acetate | q.s. |

Example 104

Capsules Comprising a $K_{ATP}$ Channel Modulator and a $CB_x$ Modulator

| | |
|---|---|
| 4-Chloro-N-[[3-(4-chloro-phenyl)-4-phenyl-4,5-dihydro-pyrazol-1-yl]-(piperidin-4-ylamino)-methylene]-benzenesulfonamide | 50 mg |
| 2-(1,5-Dimethyl-1H-pyrrol-2-yl)-5-ethyl-1-phenyl-1H-imidazole-4-carboxylic acid cyclohexylamide | 50 mg |
| Corn Starch | 150 mg |
| Lactose | 150 mg |
| Ethyl acetate | q.s. |

Example 105

Capsules Comprising a $K_{ATP}$ Channel Modulator and a $CB_x$ Modulator

| | |
|---|---|
| Morpholine-4-sulfonic acid [3-(4-chloro-phenyl)-4-phenyl-4,5-dihydro-pyrazol-1-yl]-(cyclopropylmethyl-amino)-methyleneamide | 50 mg |
| 1-[3-(4-Chloro-phenyl)-4-phenyl-4,5-dihydro-pyrazol-1-yl]-3-(1H-indol-2-yl)-2-methylamino-propan-1-one | 50 mg |
| Corn Starch | 150 mg |
| Lactose | 150 mg |
| Ethyl acetate | q.s. |

Example 106

Capsules Containing a $K_{ATP}$ Opener and a CB1 Agonist

| | |
|---|---|
| (4S)-3-(4-Chlorophenyl)-N'-[(4-chlorophenyl)sulfonyl]-N-methyl-4-phenyl-4,5-dihydro-1H-pyrazole-1-carboximid-amide | 50 mg |
| N-Adamantyl-4-pentyl-5-phenyl-thiazole-2-carboxamide | 50 mg |
| Corn Starch | 150 mg |
| Lactose | 150 mg |
| Ethyl acetate | q.s. |

Example 107

Capsules Containing a $K_{ATP}$ Opener and a CB2 Agonist

| | |
|---|---|
| (4S)-3-(4-Chlorophenyl)-N'-[(4-chlorophenyl)sulfonyl]-N-methyl-4-phenyl-4,5-dihydro-1H-pyrazole-1-carboximid-amide | 50 mg |
| N-(Endo-bicyclo[2.2.1]hept-2-yl)-5-pentyl-4-phenyl-thiazole-2-carboxamide | 50 mg |
| Corn Starch | 150 mg |
| Lactose | 150 mg |
| Ethyl acetate | q.s. |

Example 108

Capsules Containing a $K_{ATP}$ Opener and a CB2 Agonist

| | |
|---|---|
| (4S)-3-(4-Chlorophenyl)-N'-[(4-chlorophenyl)sulfonyl]-N-methyl-4-phenyl-4,5-dihydro-1H-pyrazole-1-carboximid-amide | 50 mg |
| {4-[4-(1,1-dimethyl-heptyl)-2,6-dimethoxy-phenyl]-6,6-dimethyl-bicyclo[3.1.1]hept-2-en-2-yl}-methanol (HU308) | 50 mg |
| Corn Starch | 150 mg |
| Lactose | 150 mg |
| Ethyl acetate | q.s. |

Example 109

Capsules Containing a $K_{ATP}$ Opener and a CB2 Agonist

| | |
|---|---|
| (4S)-3-(4-Chlorophenyl)-N'-[(4-chlorophenyl)sulfonyl]-N-methyl-4-phenyl-4,5-dihydro-1H-pyrazole-1-carboximid-amide | 50 mg |
| N-{1,3,3-Trimethyl-endo-(1S)-bicyclo[2.2.1]hept-2-yl}-1-[(4-methyl)-benzyl-5-(4-chloro-3-methyl-phenyl)-1H-pyrazol-3-carboxamide (SR144528) | 50 mg |
| Corn Starch | 150 mg |
| Lactose | 150 mg |
| Ethyl acetate | q.s. |

Example 110

Capsules Containing a $K_{ATP}$ Opener and a Dually Acting Compound which is Both a $CB_1$ Agonist and a $CB_2$ Agonist

| | |
|---|---|
| (4S)-3-(4-Chlorophenyl)-N'-[(4-chlorophenyl)sulfonyl]-N-methyl-4-phenyl-4,5-dihydro-1H-pyrazole-1-carboximid-amide | 50 mg |
| WIN 55-212-2 | 50 mg |
| Corn Starch | 150 mg |
| Lactose | 150 mg |
| Ethyl acetate | q.s. |

For each of the above 110 examples, the active agents, the corn starch and the lactose were processed into a homogeneous pasty mixture using ethyl acetate. The paste was grounded and the resulting granules were placed on a suitable tray and dried at 45° C. in order to remove the solvent. The dried granules were passed through a crusher and mixed in a mixer with the further following excipients:

| | |
|---|---|
| Talcum | 15 mg |
| Magnesium stearate | 15 mg |
| Corn starch | 20 mg | and then poured into 400 mg capsules (capsule size 0) to form 110 capsules, each having a different composition as disclosed above.

In examples 1 to 105, the first component is the $K_{ATP}$ channel modulator; and the second component represents the $CB_x$ modulator; or the $K_{ATP}$ channel modulator functions as a $CB_x$ modulator or the $CB_x$ modulator functions as a $K_{ATP}$ channel modulator provided that the $K_{ATP}$ channel modulator and the $CB_x$ modulator are different compounds.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

The invention claimed is:

1. A pharmaceutical composition comprising therapeutically effective quantities of: a) a $K_{ATP}$ channel modulator, which exhibits an $IC_{50}$ value [µmol] of less than about 50 when binding to SURy subunits, wherein y is 1, 2A, or 2B; and b) a $CB_x$ modulator, which exhibits an $IC_{50}$ value [µmol] greater than about 50 when binding to the $CB_1$ receptor or $CB_2$ receptor; wherein the $CB_x$ modulator is selected from the group consisting of: $CB_1$ agonists, $CB_2$ agonists, $CB_2$ antagonists, $CB_2$ inverse agonists, compounds having both $CB_1$ agonist and $CB_2$ agonist properties, and mixtures thereof:

wherein the $K_{ATP}$ channel modulator is selected from a group consisting of: 3-(1,1-dimethyl-butyl)-6,6,9-trimethyl-6a,7,10,10a-tetrahydro-6H-benzo[c]-chromene; N-{1,3,3-trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide; (2-iodo-5-nitro-phenyl)-[1-(1-methyl-piperidin-2-ylmethyl)-1H-indol-3-yl]-methanone; {4-[4-(1,1-dimethyl-heptyl)-2,6-dimethoxy-phenyl]-6,6-dimethyl-bicyclo[3.1.1]hept-2-en-2-yl}-methanol; 3-(1,1-dimethyl-heptyl)-9-hydroxymethyl-6,6-dimethyl-6a,7,10,10a-tetrahydro-6H-enzo[c]chromen-1-ol; icosa-5,8,11,14-tetraenoic acid 2-hydroxy-1-hydroxymethyl-ethyl ester; 1-aziridin-1-yl-henicosa-6,9,12,15-tetraen-2-one; noladineether; 4,4,4-trifluoro-butane-1-sulfinic acid 3-(2-hydroxymethyl-indan-4-yloxy)-phenyl ester; 7-methoxy-2-oxo-8-pentyloxy-1,2-dihydro-quinoline-3-carboxylic acid (benzo[1,3]dioxol-5-ylmethyl)-amide; N-(1-{-4-[4-chloro-2-(2-fluoro-benzenesulfonyl)-benzenesulfonyl]-phenyl}-ethyl)-methanesulfonamide; [6-iodo-2-methyl-1-(2-morpholin-4-yl-ethyl)-2,3-dihydro-1H-indol-3-yl]-(4-methoxy-phenyl)-methanone; 1-(4-chloro-phenyl)-2-(2-chloro-phenyl)-5-ethyl-1H-imidazole-4-carboxylic acid piperidin-1-ylamide; (2-methyl-1-propyl-2,3-dihydro-1H-indol-3-yl)-naphthalen-1-yl-methanone; 5-(1,1-dimethyl-heptyl)-2-[5-hydroxy-2-(3-hydroxy-propyl)-cyclohexyl]-phenol; (2-methyl-3-morpholin-4-ylmethyl-3,4-dihydro-5-oxa-2a-azacenaphthylen-1-yl)-naphthalen-1-yl-methanone; 5-(4-chloro-phenyl)-1-(2,4-dichloro-phenyl)-4-methyl-1H-pyrazole-3-carboxylic acid piperidin-1-ylamide; 5-(4-bromo-phenyl)-1-(2,4-dichloro-phenyl)-4-ethyl-1H-pyrazole-3-carboxylic acid piperidin-1-ylamide; 1-[bis-(4-chloro-phenyl)-methyl]-3-[(3,5-difluoro-phenyl)-methanesulfonyl-methylene]-azetidine; 4-chloro-N-{[3-(4-chloro-phenyl)-4-phenyl-4,5-dihydro-pyrazol-1-yl]-methylamino-methylene-benzenesulfonamide; N-{amino-[3-(4-chloro-phenyl)-4-phenyl-4,5-dihydro-pyrazol-1-yl]-methylene}-4-chloro-benzenesulfonamide; N-{[3-(4-chloro-phenyl)-4-pyridin-3-yl-4,5-dihydro-pyrazol-1-yl]-methylamino-methylene}-4-trifluoromethyl-benzenesulfonamide; 4-Chloro-N-{[3-(4-chloro-phenyl)-4-pyridin-3-yl-4,5-dihydro-pyrazol-1-yl]-methylamino-methylene}-benzenesulfonamide; 4-chloro-N-{[3-(4-chloro-phenyl)-4-(3-fluoro-phenyl)-4,5-dihydro-pyrazol-1-yl]-methoxyamino-methylene}-benzenesulfonamide; morpholine-4-sulfonic acid [3-(4-chloro-phenyl)-4-phenyl-4,5-dihydro-pyrazol-1-yl]-methylamino-methyleneamide; N-{[3-(4-chloro-phenyl)-4-(3-fluoro-phenyl)-4,5-dihydro-pyrazol-1-yl]-methylamino-methylene}-N,N-dimethyl-sulfonamide; azepane-1-sulfonic acid [3-(4-chloro-phenyl)-4-phenyl-4,5-dihydro-pyrazol-1-yl]-methylamino-methyleneamide; 4-chloro-N-{[3-(4-chloro-phenyl)-4-phenyl-4,5-dihydro-pyrazol-1-yl]-[(1-methyl-pyrrolidin-3-ylmethyl)-amino]-methylene}-benzenesulfonamide; 1-(4-chloro-phenyl)-5-phenyl-4,5-dihydro-1H-pyrazole-3-carboxamidine; N-{[3-(4-chloro-phenyl)-4-phenyl-4,5-dihydro-pyrazol-1-yl]-methylamino-methylene}-4-trifluoromethyl-benzene-sulfonamide; piperidine-1-sulfonic acid [3-(4-chloro-phenyl)-4-phenyl-4,5-dihydro-pyrazol-1-yl]-methylamino-methyleneamide; piperidine-1-sulfonic acid [3-(4-chloro-phenyl)-4-phenyl-4,5-dihydro-pyrazol-1-yl]-(2-dimethylamino-ethylamino)-methyleneamide; N,N-diethylamino-1-sulfonic acid [3-(4-chloro-phenyl)-4-phenyl-4,5-dihydro-pyrazol-1-yl]-methylsulfanyl-methyleneamide; 2-amino-1-[3-(4-chloro-phenyl)-4-phenyl-4,5-dihydro-pyrazol-1-yl]-3-(3,4-dichloro-phenyl)-propan-1-one; N,N-dimethylamino-1-sulfonic acid [3-(4-chloro-phenyl)-4-phenyl-4,5-dihydro-pyrazol-1-yl]-(2-fluoro-ethylamino)-methyleneamide; piperidine-1-sulfonic acid [3-(4-chloro-phenyl)-4-(3-fluoro-phenyl)-4,5-dihydro-pyrazol-1-yl]-methylamino-methyleneamide; 5-(4-chloro-phenyl)-1-(2,4-dichloro-phenyl)-4,5-dihydro-1H-pyrazole-3-carboxylic acid piperidine-1-ylamide; 1-(4-chloro-phenyl)-5-phenyl-4,5-dihydro-1H-pyrazole-3-carboxylic acid piperidin-1-ylamide; piperidine-1-sulfonic acid [1-(4-chloro-phenyl)-5-phenyl-4,5-dihydro-1H-pyrazol-3-yl]-methylamino-methyleneamide; morpholine-4-sulfonic acid [1-(2,4-dichloro-phenyl)-5-phenyl-4,5-dihydro-1H-pyrazol-3-yl]-methylamino-methyleneamide; 4-chloro-N-[[3-(4-chloro-phenyl)-4-phenyl-4,5-dihydro-pyrazol-1-yl]-(2-fluoro-ethylamino)-methylene]-benzenesulfonamide; 4-chloro-N-[3-(4-chloro-phenyl)-4-phenyl-4,5-dihydro-pyrazole-1-carbonyl]-benzenesulfonamide; 4-chloro-N-[[3-(4-chloro-phenyl)-4-phenyl-4,5-dihydro-pyrazol-1-yl]-(2-ethylamino-ethylamino)-methylene]-benzenesulfonamide; 4-chloro-N-{[3-(4-chloro-phenyl)-4-phenyl-4,5-dihydro-pyrazol-1-yl]-[(1-methyl-pyrrolidin-2-ylmethyl)-amino]-methylene}-benzenesulfonamide; 4-chloro-N-[[3-(4-chloro-phenyl)-4-phenyl-4,5-dihydro-pyrazol-1-yl]-(4-pyrrolidin-1-yl-butylamino)-methylene]-benzenesulfonamide; 4-chloro-N-{[3-(4-chloro-phenyl)-4-phenyl-4,5-dihydro-pyrazol-1-yl]-[(pyridin-3-ylmethyl)-amino]-methylene}-benzenesulfonamide; 1-[3-(4-chloro-phenyl)-4-phenyl-4,5-dihydro-pyrazol-1-yl]-3-(1H-indol-2-y-1)-2-methylamino-propan-1-one; 2-[3-(4-chloro-phenyl)-4-phenyl-4,5-dihydro-pyrazol-1-yl]-5-ethyl-4,5-dihydro-oxazole; 4-chloro-N-[[3-(4-chloro-phenyl)-4-phenyl-4,5-dihydro-pyrazol-1-yl]-(3-hydroxy-2,2-dimethyl-propylamino)-methylene]-benzenesulfonamide; N,N-diethylamino-1-sulfonic acid [3-(4-chloro-phenyl)-4-hydroxy-4-phenyl-4,5-dihydro-pyrazol-1-yl]-methylamino-methyleneamide; 5-(4-bromo-phenyl)-1-(2,4-dichloro-phenyl)-1H-pyrazole-3-carbonitrile; 8-chloro-1-(2,4-dichloro-phenyl)-1,3a,4,5,6,10b-hexahydro-1,2-diazabenzo[e]azulene-3-carboxylic acid piperidin-1-ylamide; 5-(4-bromo-phenyl)-1-(2,4-dichloro-phenyl)-3-[2-(3,5-difluoro-phenyl)-2-methanesulfonyl-vinyl]-4-methyl-1H-pyrazole; piperidine-1-carboxylic acid [5-(4-chloro-phenyl)-1-(2,4-dichloro-phenyl)-4-methyl-1H-pyrazol-3-yl]-amide; 1-(4-chloro-phenyl)-2-(2,4-dichloro-phenyl)-5-ethylsulfanyl-1H-imidazole-4-carboxylic acid piperidin-1-ylamide; 2-(2,4-dichloro-phenyl)-1-(4-trifluoromethyl-phenyl)-1H-imidazole-4-carboxylic acid piperidin-1-ylamide; 1-(4-chloro-phenyl)-2-(2,4-dichloro-phenyl)-5-methylsulfanyl-1H-imidazole-4-carboxylic acid piperidin-1-ylamide; 1-(4-chloro-phenyl)-2-(2,4-dichloro-phenyl)-1H-imidazole-4-carboxylic acid piperidin-1-ylamide; 1-(4-chloro-phenyl)-2-(2,4-dichloro-phenyl)-5-ethyl-1H-imidazole-4-carboxylic acid piperidin-1-ylamide; 1-(4-bromo-phenyl)-2-(2,4-dichloro-phenyl)-5-ethyl-1H-imidazole-4-carboxylic acid piperidin-1-ylamide; 1-(4-bromo-phenyl)-5-chloro-2-(2,4-dichloro-phenyl)-1H-imidazole-4-carboxylic acid piperidin-1-ylamide; 1-(4-bromo-phenyl)-2-(2,4-dichloro-phenyl)-5-ethyl-1H-imidazole-4-carboxylic acid cyclohexylamide; 1-(4-bromo-phenyl)-2-(2,4-dichloro-phenyl)-5-ethyl-1H-imidazole-4-carboxylic acid pentylamide; 4-(4-chloro-phenyl)-5-(2,4-dichloro-phenyl)-1-methyl-1H-imidazole-2-carboxylic acid cyclohexylamide; 4-(4-chloro-phenyl)-5-(2,4-dichloro-phenyl)-3-methyl-1H-imidazole-2-carboxylic acid cyclohexylamide; 1-(5-chloro-pyridin-2-yl)-2-(2,4-dichloro-phenyl)-5-ethyl-1H-imidazole-4-carboxylic acid piperidin-1-ylamide; 1-(4-chloro-phenyl)-2-(2,4-dichloro-phenyl)-5-methyl-1H-imidazole-4-carboxylic acid (4-hydroxy-cyclohexyl)-amide; 1-(4-chloro-phenyl)-2-(2,4-dichloro-phenyl)-5-methyl-1H-imidazole-4-carboxylic acid azepan-1-ylamide; 2-(2,4-dichloro-phenyl)-5-ethyl-1-phenyl-1H-imidazole-4-carboxylic acid piperidin-1-ylamide; 2-(1,5-dimethyl-1H-pyrrol-2-yl)-5-ethyl-1-phenyl-1H-imidazole-4-carboxylic acid cyclohexylamide; 1-(4-chloro-phenyl)-5-ethyl-2-(3-methyl-pyridin-2-yl)-1H-imidazole-4-carboxylic acid piperidin-1-ylamide; 1-(4-chloro-phenyl)-5-ethyl-2-(3-methyl-pyridin-2-yl)-1H-imidazole-4-carboxylic acid cyclohexylamide; 1-(4-chloro-phenyl)-2-(2,4-dichloro-phenyl)-5-methyl-1H-imidazole-4-carboxylic acid (4-trifluoromethyl-phenyl)-amide; 2-(2,4-dichloro-phenyl)-5-methyl-1-pyridin-2-yl-1H-imidazole-4-carboxylic acid piperidin-1-ylamide; 1-(4-chloro-phenyl)-2-(2,4-dichloro-phenyl)-5-fluoromethyl-1H-imidazole-4-carboxylic acid piperidin-1-ylamide; 1-(4-chloro-phenyl)-2-(2,4-dichloro-phenyl)-5-hydroxymethyl-1H-imidazole-4-carboxylic acid piperidin-1-ylamide; 1-(4-chloro-phenyl)-2-(2,4-dichloro-phenyl)-5-methylsulfanyl-1H-imidazole-4-carboxylic acid cyclohexylamide; 1-(4-chloro-phenyl)-2-(2,4-dichloro-phenyl)-5-methanesulfonyl-1H-imidazole-4-carboxylic acid piperidin-1-ylamide; 1-(4-chloro-phenyl)-2-(2,4-dichloro-phenyl)-5-methanesulfinyl-1H-imidazole-4-carboxylic acid piperidin-1-ylamide; 5-(4-chloro-phenyl)-4-(2,5-dichloro-phenyl)-1-methyl-1H-imidazole-2-carboxylic acid piperidin-1-ylamide; 2-(2-chloro-phenyl)-1-(5-chloro-pyridin-2-yl)-5-ethyl-1H-imidazole-4-carboxylic acid piperidin-1-ylamide; 1-(4-chloro-phenyl)-2-(2,4-dichloro-phenyl)-5-(2,2,2-trifluoroethyl)-1H-imidazole-4-carboxylic acid piperidin-1-ylamide; N-[1-(4-chloro-phenyl)-2-(2,4-dichloro-phenyl)-5-methyl-1H-imidazol-4-yl]-benzamide; 1-(4-chloro-phenyl)-2-(2,4-dichloro-phenyl)-5-pyrrolidin-1-ylmethyl-1H-imidazole-4-carboxylic acid piperidin-1-ylamide; 2-[1-(4-chloro-phenyl)-2-(2,4-dichloro-phenyl)-5-methyl-1H-imidazol-4-yl]-hexan-2-ol; 1-(4-chloro-phenyl)-2-(2,4-dichloro-phenyl)-5-methyl-4-pentyl-1H-imidazole; 2,5-dimethyl-1-phenyl-1H-imidazole-4-carboxylic acid adamantan-2-ylamide; 1-(4-chloro-phenyl)-2-(2-chloro-phenyl)-5-methylsulfanyl-1H-imidazole-4-carboxylic acid piperidin-1-ylamide; 2-(2-chloro-phenyl)-1-(4-trifluoromethyl-phenyl)-1H-imidazole-4-carboxylic acid piperidin-1-ylamide; 5-(4-chloro-phenyl)-1-(2,4-dichloro-phenyl)-1H-[1,2,4]-triazole-3-carboxylic acid pyrrolidin-1-ylamide; 1-(4-chloro-phenyl)-5-(2,4-dichloro-phenyl)-1H-[1,2,4]triazole-3-carboxylic acid piperidin-1-yl-amide; 1-{(4-chloro-benzene-sulfonylimino)-[3-(4-chloro-phenyl)-4-phenyl-4,5-dihydro-pyrazol-1-yl]-methyl}-piperidine-4-carboxylic acid amide; 4-chloro-N-{[3-(4-chloro-phenyl)-4-phenyl-4,5-dihydro-pyrazol-1-yl]-[2-(2-oxo-pyrrolidin-1-yl)-ethylamino]-methylene}-benzenesulfonamide;

4-chloro-N-[[3-(4-chloro-phenyl)-4-phenyl-4,5-dihydro-pyrazol-1-yl]-(2-cyano-ethylamino)-methylene]-benzene-sulfonamide; 4-chloro-N-[[3-(4-chloro-phenyl)-4-phenyl-4,5-dihydro-pyrazol-1-yl]-(methoxy-methylamino)-methylene]-benzenesulfonamide; 4-chloro-N-{[3-(4-chloro-phenyl)-4-phenyl-4,5-dihydro-pyrazol-1-yl]-[(piperidin-4-ylmethyl)-amino]-methylene}-benzenesulfonamide; 4-chloro-N-[[3-(4-chloro-phenyl)-4-phenyl-4,5-dihydro-pyrazol-1-yl]-(piperidin-4-ylamino)-methylene]-benzenesulfonamide; morpholine-4-sulfonic acid [3-(4-chloro-phenyl)-4-phenyl-4,5-dihydro-pyrazol-1-yl]-(cyclopropyl-methylamino)-methyleneamide; 1-{(4-chloro-benzene-sulfonylimino)-[3-(4-chloro-phenyl)-4-phenyl-4,5-dihydro-pyrazol-1-yl]-methyl}-piperidine-4-carboxylic acid amide; morpholine-4-sulfonic acid [3-(4-chloro-phenyl)-4-phenyl-4,5-dihydro-pyrazol-1-yl]-(cyclopropyl-methylamino)-methyleneamide; pinacidil; cromakalim; diazoxide; 1-(4-(1H-imidazol-1-yl)benzoyl)-N-methylcyclobutanecarbothioamide (MCC-134); 4-(2-cyanimino-1,2-dihydropyrid-1-yl)-2,2-dimethyl-6-nitrochromene (SR 47063); R-4-[3,4-dioxo-2-(1,2,2-trimethyl-propylamino)-cyclobut-1-1-enylamino]-3-methoxybenzonitrile (WAY 135201); and mixtures thereof;

wherein the $CB_1$ agonist is selected from the group consisting of: (6ar,10ar)-3-(1,1-dimethylheptyl)-1-methoxy-6,6,9-trimethyl-6a,7,10,10a-tetrahydro-6H-enzo[c]chromene (L759633); (6ar,10ar)-3-(1,1-dimethylheptyl)-1-methoxy-6,6-dimethyl-9-methylene-6a,7,8,9,10,10a-hexahydro-6H-benzo[c]chromene (L759656); {4-[4-(1,1-dimethyl-heptyl)-2,6-dimethoxy-phenyl]-6,6-dimethyl-bicyclo-[3.1.1]hept-2-en-2-yl}-methanol (HU308); (2-Methyl-1-propyl-1H-indol-3-yl)-1-naphthalenylmethanone (JWH015); (2-iodo-5-nitro-phenyl)-[1-(1-methyl-piperidin-2-ylmethyl)-1H-indol-3-yl]- -methanone (AM-1241); 3-(1,1-dimethyl-butyl)-6,6,9-trimethyl-6a,7,10,10a-tetrahydro-6H-benzo[c]-chromene (JWH133); 6,6,9-trimethyl-3-pentyl-6a,7,8,10a-tetrahydro-6H-benzo[c]chromen-1-ol; dronabinol; 5-(1,1-dimethyl-heptyl)-2-[5-hydroxy-2-(3-hydroxy-propyl)-cyclohexyl]-phenol (CP-55,940); (2-methyl-3-morpholin-4-ylmethyl-3,4-dihydro-5-oxa-2a-aza-acenaphthylen-1-yl)-naphthalen-1-yl-methanone (WIN-55,212-2); (6aR,10aR)-9-(Hydroxymethyl)-6,6-dimethyl-3-(2-methyloctan-2-yl)-6a,7,10,10a-tetrahydrobenzo[c]chromen-1-ol (HU210); arachidonyl-2-chloroethylamid (ACEA); arachidonylcyclopropylamide (ACPA); methanandamide; anandamide; 2-arachidonoyl glycerol; 2-icosa-5,8,11,14-tetraenyloxy-propane-1,3-diol (noladinether); (−)-(R)-3-(2-Hydroxymethylindanyl-4-oxy)phenyl-4,4,4-trifluorobutyl-1-sulfonate (BAY 38-7271); naphthalen-1-yl-(4-pentyloxynaphthalen-1-yl) methanone (SAB-378); 3-[2-cyano-3-(trifluoromethyl)phenoxy]phenyl 4,4,4-trifluoro-1-butanesulfonic acid ester (BAY 59-3074); 3-(5'-cyano-1',1'-dimethylpentyl)-1-(4-N-morpholino-butyryloxy)-D8-tetrahydrocannabinol hydrochloride (0-1057); delta-9-tetrahydrocannabinol (GW-1000); Butenedioic acid (2E)-, mono[5-(1,1-dimethylheptyl)-2-[(1S,2S,5S)-6,6-dimethyl-4-oxobicyclo[3.1.1]hept-2-yl]-3-hydroxyphenyl]ester (PRS-211375); PRS-211359; PRS-211355; 3-(4-tert-Butyl-2,6-dihydroxy-benzyl)-4-isopropenyl-cyclohexanone (PRS-211096); 2-(2,4-dichloro-phenylamino)-4-trifluoromethyl-pyrimidine-5-carboxylic acid (tetrahydropyran-4-ylmethyl)-amide (GW-842166X); and mixtures thereof;

wherein the $CB_2$ agonist is selected from the group consisting of: (6ar,10ar)-3-(1,1-dimethylheptyl)-1-methoxy-6,6,9-trimethyl-6a,7,10,10a-tetrahydro-6H-enzo[c]chromene (L759633); (6ar,10ar)-3-(1,1-dimethylheptyl)-1-methoxy-6,6-dimethyl-9-methylene-6a,7,8,9,10,10a-hexahydro-6H-benzo[c]chromene (L759656); {4-[4-(1,1-dimethyl-heptyl)-2,6-dimethoxy-phenyl]-6,6-dimethyl-bicyclo-[3.1.1]hept-2-en-2-yl}-methanol (HU308); (2-Methyl-1-propyl-1H-indol-3-yl)-1-naphthalenylmethanone (JWH015); (2-iodo-5-nitro-phenyl)-[1-(1-methyl-piperidin-2-ylmethyl)-1H-indol-3-yl]- -methanone (AM-1241); 3-(1,1-dimethyl-butyl)-6,6,9-trimethyl-6a,7,10,10a-tetrahydro-6H-benzo[c]-chromene (JWH133); 6,6,9-trimethyl-3-pentyl-6a,7,8,10a-tetrahydro-6H-benzo[c]chromen-1-ol; dronabinol; 5-(1,1-dimethyl-heptyl)-2-[5-hydroxy-2-(3-hydroxy-propyl)-cyclohexyl]-phenol (CP-55,940); (2-methyl-3-morpholin-4-ylmethyl-3,4-dihydro-5-oxa-2a-aza-acenaphthylen-1-yl)-naphthalen-1-yl-methanone (WIN-55,212-2); (6aR,10aR)-9-(Hydroxymethyl)-6,6-dimethyl-3-(2-methyloctan-2-yl)-6a,7,10,10a-tetrahydrobenzo[c]chromen-1-ol (HU210); arachidonyl-2-chloroethylamid (ACEA); arachidonylcyclopropylamide (ACPA); methanandamide; anandamide; 2-arachidonoyl glycerol; 2-icosa-5,8,11,14-tetraenyloxy-propane-1,3-diol (noladinether); (−)-(R)-3-(2-Hydroxymethylindanyl-4-oxy)phenyl-4,4,4-trifluorobutyl-1-sulfonate (BAY 38-7271); naphthalen-1-yl-(4-pentyloxynaphthalen-1-yl)methanone (SAB-378); 3-[2-cyano-3-(trifluoromethyl)phenoxy]phenyl 4,4,4-trifluoro-1-butanesulfonic acid ester (BAY 59-3074); 3-(5'-cyano-1',1'-dimethylpentyl)-1-(4-N-morpholino-butyryloxy)-D8-tetrahydrocannabinol hydrochloride (0-1057); delta-9-tetrahydrocannabinol (GW-1000); Butenedioic acid (2E)-, mono[5-(1,1-dimethylheptyl)-2-[(1S,2S,5S)-6,6-dimethyl-4-oxobicyclo[3.1.1]hept-2-yl]-3-hydroxyphenyl]ester (PRS-211375); PRS-211359; PRS-211355; 3-(4-tert-Butyl-2,6-dihydroxy-benzyl)-4-isopropenyl-cyclohexanone (PRS-211096); 2-(2,4-dichloro-phenylamino)-4-trifluoromethyl-pyrimidine-5-carboxylic acid (tetrahydropyran-4-ylmethyl)-amide (GW-842166X); and mixtures thereof;

wherein the $CB_2$ antagonist is selected from the group consisting of: N-{1,3,3-trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide (SR-144528), N-(1,3-Benzodioxol-5-ylmethyl)-1,2-dihydro-7-methoxy-2-oxo-8-(pentyloxy)-3-quinolinecarboxamide (JTE-907), 6-Iodo-2-methyl-1-[2-(4-morpholinyl)ethyl]-1H-indol-3-yl](4-methoxyphenyl)methanone (AM630), and mixtures thereof;

wherein the $CB_2$ inverse agonist is selected from the group consisting of: N-{1,3,3-trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide (SR-144528), N-(1,3-Benzodioxol-5-ylmethyl)-1,2-dihydro-7-methoxy-2-oxo-8-(pentyloxy)-3-quinolinecarboxamide (JTE-907), 6-Iodo-2-methyl-1-[2-(4-morpholinyl)ethyl]-1H-indol-3-yl](4-methoxyphenyl)methanone (AM630), and mixtures thereof; and wherein the compounds having both CB₁ agonist and CB₂ agonist properties is selected from the group consisting of: dronabinol; (6aR,10aR)-9-(Hydroxymethyl)-6,6-dimethyl-3-(2-methyloctan-2-yl)-6a,7,10,10a-tetrahydrobenzo[c]chromen-1-ol (HU210); 2-icosa-5,8,11,14-tetraenyloxy-propane-1,3-diol (noladinether); and mixtures thereof.

2. The pharmaceutical composition of claim 1, further comprising a pharmaceutically acceptable excipient.

3. The pharmaceutical composition of claim 1 wherein the pharmaceutical composition is a dosage form suitable for oral administration.

4. The pharmaceutical composition of claim 3 wherein the oral dosage form is selected from the group consisting of: tablets, coated tablets, capsules, syrups, elixirs and suspensions.

5. The pharmaceutical composition of claim 1 wherein (a) the $K_{ATP}$ channel modulator also functions as a $CB_x$ modulator; or (b) the $CB_x$ modulator also functions as a $K_{ATP}$ channel modulator; provided that the $K_{ATP}$ channel modulator and the $CB_x$ modulator are different compounds.

6. A method of using a $K_{ATP}$ channel modulator, which exhibits an $IC_{50}$ value [µmol] of less than about 50 when binding to SURy subunits, wherein y is 1, 2A, or 2B; for the treatment of a medical condition in a mammal comprising the steps of: combining the $K_{ATP}$ channel modulator with a $CB_x$ modulator, which exhibits an $IC_{50}$ value [µmol] greater than about 50 when binding to the $CB_1$ receptor or $CB_2$ receptor; and administering the combined $K_{ATP}$ channel modulator and $CB_x$ modulator to the mammal; wherein the $CB_x$ modulator is selected from the group consisting of: CB₁ agonists, CB₂ agonists, CB₂ antagonists, CB₂ inverse agonists, compounds having both CB₁ agonist and CB₂ agonist properties, and mixtures thereof; and wherein the medical condition is selected from the group consisting of: obesity, diabetes mellitus type I and II, metabolic syndrome, insulinoma, familial hyperinsulemic hypoglycemia, male pattern baldness, detrusor hyperreactivity, asthma, epilepsy, analgesia, angina, arrhythmia, coronary spasm, peripheral vascular disease, cerebral vasospasm, appetite regulation, pain, neuropathic pain, chronic pain, idiopathic pain and impotence;

wherein the $K_{ATP}$ channel modulator is selected from a group consisting of: 3-(1,1-dimethyl-butyl)-6,6,9-trimethyl-6a,7,10,10a-tetrahydro-6H-benzo[c]-chromene; N-{1,3,3-trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide; (2-iodo-5-nitro-phenyl)-[1-(1-methyl-piperidin-2-ylmethyl)-1H-indol-3-yl]-methanone; {4-[4-(1,1-dimethyl-heptyl)-2,6-dimethoxy-phenyl]-6,6-dimethyl-bicyclo[3.1.1]hept-2-en-2-yl}-methanol; 3-(1,1-dimethyl-heptyl)-9-hydroxymethyl-6,6-dimethyl-6a,7,10,10a-tetrahydro-6H-enzo[c]chromen-1-ol; icosa-5,8,11,14-tetraenoic acid 2-hydroxy-1-hydroxymethyl-ethyl ester; 1-aziridin-1-yl-henicosa-6,9,12,15-tetraen-2-one; noladineether; 4,4,4-trifluoro-butane-1-sulfinic acid 3-(2-hydroxymethyl-indan-4-yloxy)-phenyl ester; 7-methoxy-2-oxo-8-pentyloxy-1,2-dihydro-quinoline-3-carboxylic acid (benzo[1,3]dioxol-5-ylmethyl)-amide; N-(1-[4-[4-chloro-2-(2-fluoro-benzenesulfonyl)-benzenesulfonyl]-phenyl}-ethyl)-methanesulfonamide; [6-iodo-2-methyl-1-(2-morpholin-4-yl-ethyl)-2,3-dihydro-1H-indol-3-yl]-(4-methoxy-phenyl)-methanone; 1-(4-chloro-phenyl)-2-(2-chloro-phenyl)-5-ethyl-1H-imidazole-4-carboxylic acid piperidin-1-ylamide; (2-methyl-1-propyl-2,3-dihydro-1H-indol-3-yl)-naphthalen-1-yl-methanone; 5-(1,1-dimethyl-heptyl)-2-[5-hydroxy-2-(3-hydroxy-propyl)-cyclohexyl]-phenol; (2-methyl-3-morpholin-4-ylmethyl-3,4-dihydro-5-oxa-2a-azacenaphthylen-1-yl)-naphthalen-1-yl-methanone; 5-(4-chloro-phenyl)-1-(2,4-dichloro-phenyl)-4-methyl-1H-pyrazole-3-carboxylic acid piperidin-1-ylamide; 5-(4-bromophenyl)-1-(2,4-dichloro-phenyl)-4-ethyl-1H-pyrazole-3-carboxylic acid piperidin-1-ylamide; 1-[bis-(4-chloro-phenyl)-methyl]-3-[(3,5-difluoro-phenyl)-methanesulfonyl-methylene]-azetidine; 4-chloro-N-{[3-(4-chloro-phenyl)-4-phenyl-4,5-dihydro-pyrazol-1-yl]-methylamino-methylene-benzenesulfonamide; N-{amino-[3-(4-chloro-phenyl)-4-phenyl-4,5-dihydro-pyrazol-1-yl]-methylene}-4-chloro-benzenesulfonamide; N-{[3-(4-chloro-phenyl)-4-pyridin-3-yl-4,5-dihydro-pyrazol-1-yl]-methylamino-methylene}-4-trifluoromethyl-benzenesulfonamide; 4-Chloro-N-{[3-(4-chloro-phenyl)-4-pyridin-3-yl-4,5-dihydro-pyrazol-1-yl]-methylamino-methylene}-benzenesulfonamide; 4-chloro-N-{[3-(4-chloro-phenyl)-4-(3-fluoro-phenyl)-4,5-dihydro-pyrazol-1-yl]-methoxyamino-methylene}-benzenesulfonamide; morpholine-4-sulfonic acid [3-(4-chloro-phenyl)-4-phenyl-4,5-dihydro-pyrazol-1-yl]-methylamino-methyleneamide; N-{[3-(4-chloro-phenyl)-4-(3-fluoro-phenyl)-4,5-dihydro-pyrazol-1-yl]-methylamino-methylene}-N,N-dimethylsulfonamide; azepane-1-sulfonic acid [3-(4-chloro-phenyl)-4-phenyl-4,5-dihydro-pyrazol-1-yl]-methylamino-methyleneamide; 4-chloro-N-{[3-(4-chloro-phenyl)-4-phenyl-4,5-dihydro-pyrazol-1-yl]-[(1-methyl-pyrrolidin-3-ylmethyl)-amino]-methylene}-benzenesulfonamide; 1-(4-chloro-phenyl)-5-phenyl-4,5-dihydro-1H-pyrazole-3-carboxamidine; N-{[3-(4-chloro-phenyl)-4-phenyl-4,5-dihydro-pyrazol-1-yl]-methylamino-methylene}-4-trifluoromethyl-benzene-sulfonamide; piperidine-1-sulfonic acid [3-(4-chloro-phenyl)-4-phenyl-4,5-dihydro-pyrazol-1-yl]-methylamino-methyleneamide; piperidine-1-sulfonic acid [3-(4-chloro-phenyl)-4-phenyl-4,5-dihydro-pyrazol-1-yl]-(2-dimethylamino-ethylamino)-methyleneamide; N,N-diethylamino-1-sulfonic acid [3-(4-chloro-phenyl)-4-phenyl-4,5-dihydro-pyrazol-1-yl]-methylsulfanyl-methyleneamide; 2-amino-1-[3-(4-chloro-phenyl)-4-phenyl-4,5-dihydro-pyrazol-1-yl]-3-(3,4-dichloro-phenyl)-propan-1-one; N,N-dimethylamino-1-sulfonic acid [3-(4-chloro-phenyl)-4-phenyl-4,5-dihydro-pyrazol-1-yl]-(2-fluoro-ethylamino)-methyleneamide; piperidine-1-sulfonic acid [3-(4-chloro-phenyl)-4-(3-fluoro-phenyl)-4,5-dihydro-pyrazol-1-yl]-methylamino-methyleneamide; 5-(4-chloro-phenyl)-1-(2,4-dichloro-phenyl)-4,5-dihydro-1H-pyrazole-3-carboxylic acid piperidine-1-ylamide; 1-(4-chloro-phenyl)-5-phenyl-4,5-dihydro-1H-pyrazole-3-carboxylic acid piperidin-1-ylamide; piperidine-1-sulfonic acid [1-(4-chloro-phenyl)-5-phenyl-4,5-dihydro-1H-pyrazol-3-yl]-methylamino-methyleneamide; morpholine-4-sulfonic acid [1-(2,4-dichloro-phenyl)-5-phenyl-4,5-dihydro-1H-pyrazol-3-yl]-methylamino-methyleneamide; 4-chloro-N-[[3-(4-chloro-phenyl)-4-phenyl-4,5-dihydro-pyrazol-1-yl]-(2-fluoro-ethylamino)-methylene]-benzenesulfonamide; 4-chloro-N-[3-(4-chloro-phenyl)-4-phenyl-4,5-dihydro-pyrazole-1-carbonyl]-benzenesulfonamide; 4-chloro-N-[[3-(4-chloro-phenyl)-4-phenyl-4,5-dihydro-pyrazol-1-yl]-(2-ethylamino-ethylamino)-methylene]-benzenesulfonamide; 4-chloro-N-{[3-(4-chloro-phenyl)-4-phenyl-4,5-dihydro-pyrazol-1-yl]-[(1- methyl-pyrrolidin-2-ylmethyl)-amino]-methylene}-benzenesulfonamide; 4-chloro-N-[[3-(4-chloro-phenyl)-4-phenyl-4,5-dihydro-pyrazol-1-yl]-(4-pyrrolidin-1-yl-butylamino)-methylene]-benzenesulfonamide; 4-chloro-N-{[3-(4-chloro-phenyl)-4-phenyl-4,5-dihydro-pyrazol-1-yl]-[(pyridin-3-ylmethyl)-amino]-methylene}-benzenesulfonamide; 1-[3-(4-chloro-phenyl)-4-phenyl-4,5-dihydro-pyrazol-1-yl]-3-(1H-indol-2-y-1)-2-methylamino-propan-1-one; 2-[3-(4-chloro-phenyl)-4-phenyl-4,5-dihydro-pyrazol-1-yl]-5-ethyl-4,5-dihydro-oxazole; 4-chloro-N-[[3-(4-chloro-phenyl)-4-phenyl-4,5-dihydro-pyrazol-1-yl]-(3-hydroxy-2,2-dimethyl-propylamino)-methylene]-benzenesulfonamide; N,N-diethylamino-1-sulfonic acid [3-(4-chloro-phenyl)-4-hydroxy-4-phenyl-4,5-dihydro-pyrazol-1-yl]-methylamino-methyleneamide; 5-(4-bromo-phenyl)-1-(2,4-dichloro-phenyl)-1H-pyrazole-3-carbonitrile; 8-chloro-1-(2,4-dichloro-phenyl)-1,3a,4,5,6,10b-hexahydro-1,2-diazabenzo[e]azulene-3-carboxylic acid piperidin-1-ylamide; 5-(4-bromo-phenyl)-1-(2,4-dichloro-phenyl)-3-[2-(3,5-difluoro-phenyl)-2-methanesulfonyl-vinyl]-4-methyl-1H-pyrazole; piperidine-1-carboxylic acid [5-(4-chloro-phenyl)-1-(2,4-dichloro-phenyl)-4-methyl-1H-pyrazol-3-yl]-amide; 1-(4-chloro-phenyl)-2-(2,4-dichloro-phenyl)-5-ethylsulfanyl-1H-imidazole-4-carboxylic acid piperidin-1-ylamide; 2-(2,4-dichloro-phenyl)-1-(4-trifluoromethyl-phenyl)-1H-imidazole-4-carboxylic acid piperidin-1-ylamide; 1-(4-chloro-phenyl)-2-(2,4-dichloro-phenyl)-5-methylsulfanyl-1H-imidazole-4-carboxylic acid piperidin-1-ylamide; 1-(4-chloro-phenyl)-2-(2,4-dichloro-phenyl)-1H-imidazole-4-carboxylic acid piperidin-1-ylamide; 1-(4-chloro-phenyl)-2-(2,4-dichloro-phenyl)-5-ethyl-1H-imidazole-4-carboxylic acid piperidin-1-ylamide; 1-(4-bromo-phenyl)-2-(2,4-dichloro-phenyl)-5-ethyl-1H-imidazole-4-carboxylic acid piperidin-1-ylamide; 1-(4-bromo-phenyl)-5-chloro-2-(2,4-dichloro-phenyl)-1H-imidazole-4-carboxylic acid piperidin-1-ylamide; 1-(4-bromo-phenyl)-2-(2,4-dichloro-phenyl)-5-ethyl-1H-imidazole-4-carboxylic acid cyclohexylamide; 1-(4-bromo-phenyl)-2-(2,4-dichloro-phenyl)-5-ethyl-1H-imidazole-4-carboxylic acid pentylamide; 4-(4-chloro-phenyl)-5-(2,4-dichloro-phenyl)-1-methyl-1H-imidazole-2-carboxylic acid cyclohexylamide; 4-(4-chloro-phenyl)-5-(2,4-dichloro-phenyl)-3-methyl-1H-imidazole-2-carboxylic acid cyclohexylamide; 1-(5-chloro-pyridin-2-yl)-2-(2,4-dichloro-phenyl)-5-ethyl-1H-imidazole-4-carboxylic acid piperidin-1-ylamide; 1-(4-chloro-phenyl)-2-(2,4-dichloro-phenyl)-5-methyl-1H-imidazole-4-carboxylic acid (4-hydroxy-cyclohexyl)-amide; 1-(4-chloro-phenyl)-2-(2,4-dichloro-phenyl)-5-methyl-1H-imidazole-4-carboxylic acid azepan-1-ylamide; 2-(2,4-dichloro-phenyl)-5-ethyl-1-phenyl-1H-imidazole-4-carboxylic acid piperidin-1-ylamide; 2-(1,5-dimethyl-1H-pyrrol-2-yl)-5-ethyl-1-phenyl-1H-imidazole-4-carboxylic acid cyclohexylamide; 1-(4-chloro-phenyl)-5-ethyl-2-(3-methyl-pyridin-2-yl)-1H-imidazole-4-carboxylic acid piperidin-1-ylamide; 1-(4-chloro-phenyl)-5-ethyl-2-(3-methyl-pyridin-2-yl)-1H-imidazole-4-carboxylic acid cyclohexylamide; 1-(4-chloro-phenyl)-2-(2,4-dichloro-phenyl)-5-methyl-1H-imidazole-4-carboxylic acid (4-trifluoromethyl-phenyl)-amide; 2-(2,4-dichloro-phenyl)-5-methyl-1-pyridin-2-yl-1H-imidazole-4-carboxylic acid piperidin-1-ylamide; 1-(4-chloro-phenyl)-2-(2,4-dichloro-phenyl)-5-fluoromethyl-1H-imidazole-4-carboxylic acid piperidin-1-ylamide; 1-(4-chloro-phenyl)-2-(2,4-dichloro-phenyl)-5-hydroxymethyl-1H-imidazole-4-carboxylic acid piperidin-1-ylamide; 1-(4-chloro-phenyl)-2-(2,4-dichloro-phenyl)-5-methylsulfanyl-1H-imidazole-4-carboxylic acid cyclohexylamide; 1-(4-chloro-phenyl)-2-(2,4-dichloro-phenyl)-5-methanesulfonyl-1H-imidazole-4-carboxylic acid piperidin-1-ylamide; 1-(4-chloro-phenyl)-2-(2,4-dichloro-phenyl)-5-methanesulfinyl-1H-imidazole-4-carboxylic acid piperidin-1-ylamide; 5-(4-chloro-phenyl)-4-(2,5-dichloro-phenyl)-1-methyl-1H-imidazole-2-carboxylic acid piperidin-1-ylamide; 2-(2-chloro-phenyl)-1-(5-chloro-pyridin-2-yl)-5-ethyl-1H-imidazole-4-carboxylic acid piperidin-1-ylamide; 1-(4-chloro-phenyl)-2-(2,4-dichloro-phenyl)-5-(2,2,2-trifluoroethyl)-1H-imidazole-4-carboxylic acid piperidin-1-ylamide; N-[1-(4-chloro-phenyl)-2-(2,4-dichloro-phenyl)-5-methyl-1H-imidazol-4-yl]-benzamide; 1-(4-chloro-phenyl)-2-(2,4-dichloro-phenyl)-5-pyrrolidin-1-ylmethyl-1H-imidazole-4-carboxylic acid piperidin-1-ylamide; 2-[1-(4-chloro-phenyl)-2-(2,4-dichloro-phenyl)-5-methyl-1H-imidazol-4-yl]-hexan-2-ol; 1-(4-chloro-phenyl)-2-(2,4-dichloro-phenyl)-5-methyl-4-pentyl-1H-imidazole; 2,5-dimethyl-1-phenyl-1H-imidazole-4-carboxylic acid adamantan-2-ylamide; 1-(4-chloro-phenyl)-2-(2-chloro-phenyl)-5-methylsulfanyl-1H-imidazole-4-carboxylic acid piperidin-1-ylamide; 2-(2-chloro-phenyl)-1-(4-trifluoromethyl-phenyl)-1H-imidazole-4-carboxylic acid piperidin-1-ylamide; 5-(4-chloro-phenyl)-1-(2,4-dichloro-phenyl)-1H-[1,2,4]triazole-3-carboxylic acid pyrrolidin-1-ylamide; 1-(4-chloro-phenyl)-5-(2,4-dichloro-phenyl)-1H-[1,2,4]-triazole-3-carboxylic acid piperidin-1-yl-amide; 1-{(4-chloro-benzene-sulfonylimino)-[3-(4-chloro-phenyl)-4-phenyl-4,5-dihydro-pyrazol-1-yl]-methyl}-piperidine-4-carboxylic acid amide; 4-chloro-N-{[3-(4-chloro-phenyl)-4-phenyl-4,5-dihydro-pyrazol-1-yl]-[2-(2-oxo-pyrrolidin-1-yl)-ethylamino]-methylene}-benzenesulfonamide; 4-chloro-N-[[3-(4-chloro-phenyl)-4-phenyl-4,5-dihydro-pyrazol-1-yl]-(2-cyano-ethylamino)-methylene]-benzene-sulfonamide; 4-chloro-N-[[3-(4-chloro-phenyl)-4-phenyl-4,5-dihydro-pyrazol-1-yl]-(methoxy-methylamino)-methylene]-benzenesulfonamide; 4-chloro-N-{[3-(4-chloro-phenyl)-4-phenyl-4,5-dihydro-pyrazol-1-yl]-[(piperidin-4-ylmethyl)-amino]-methylene}-benzenesulfonamide; 4-chloro-N-[[3-(4-chloro-phenyl)-4-phenyl-4,5-dihydro-pyrazol-1-yl]-(piperidin-4-ylamino)-methylene]-benzenesulfonamide; morpholine-4-sulfonic acid [3-(4-chloro-phenyl)-4-phenyl-4,5-dihydro-pyrazol-1-yl]-(cyclopropyl-methylamino)-methyleneamide; 1-{(4-chloro-benzene-sulfonylimino)-[3-(4-chloro-phenyl)-4-phenyl-4,5-dihydro-pyrazol-1-yl]-methyl}-piperidine-4-carboxylic acid amide; morpholine-4-sulfonic acid [3-(4-chloro-phenyl)-4-phenyl-4,5-dihydro-pyrazol-1-yl]-(cyclopropyl-methylamino)-methyleneamide; pinacidil; cromakalim; diazoxide; 1-(4-(1H-imidazol-1-yl)benzoyl)-N-methylcyclobutanecarbothioamide (MCC-134); 4-(2-cyanimino-1,2-dihydropyrid-1-yl)-2,2-dimethyl-6-nitrochromene (SR 47063); R-4-[3,4-dioxo-2-(1,2,2-trimethyl-propylamino)-cyclobut-1-1-enylamino]-3-methoxybenzonitrile (WAY 135201); and mixtures thereof;

wherein the $CB_1$ agonist is selected from the group consisting of: (6ar,10ar)-3-(1,1-dimethylheptyl)-1-methoxy-6,6,9-trimethyl-6a,7,10,10a-tetrahydro-6H-enzo

[c]chromene (L759633); (6ar,10ar)-3-(1,1-dimethylheptyl)-1-methoxy-6,6-dimethyl-9-methylene-6a,7,8,9,10,10a-hexahydro-6H-benzo[c]chromene (L759656); {4-[4-(1,1-dimethyl-heptyl)-2,6-dimethoxy-phenyl]-6,6-dimethyl-bicyclo-[3.1.1]hept-2-en-2-yl}-methanol (HU308); (2-Methyl-1-propyl-1H-indol-3-yl)-1-naphthalenylmethanone (JWH015); (2-iodo-5-nitro-phenyl)-[1-(1-methyl-piperidin-2-ylmethyl)-1H-indol-3-yl]- -methanone (AM-1241); 3-(1,1-dimethyl-butyl)-6,6,9-trimethyl-6a,7,10,10a-tetrahydro-6H-benzo[c]-chromene (JWH133); 6,6,9-trimethyl-3-pentyl-6a,7,8,10a-tetrahydro-6H-benzo[c]chromen-1-ol; dronabinol; 5-(1,1-dimethyl-heptyl)-2-[5-hydroxy-2-(3-hydroxy-propyl)-cyclohexyl]-phenol (CP-55,940); (2-methyl-3-morpholin-4-ylmethyl-3,4-dihydro-5-oxa-2a-aza-acenaphthylen-1-yl)-naphthalen-1-yl-methanone (WIN-55,212-2); (6aR,10aR)-9-(Hydroxymethyl)-6,6-dimethyl-3-(2-methyloctan-2-yl)-6a,7,10,10a-tetrahydrobenzo[c]chromen-1-ol (HU210); arachidonyl-2-chloroethylamid (ACEA); arachidonylcyclopropylamide (ACPA); methanandamide; anandamide; 2-arachidonoyl glycerol; 2-icosa-5,8,11,14-tetraenyloxy-propane-1,3-diol (noladinether); (−)-(R)-3-(2-Hydroxymethylindanyl-4-oxy)phenyl-4,4,4-trifluorobutyl-1-sulfonate (BAY 38-7271); naphthalen-1-yl-(4-pentyloxynaphthalen-1-yl)methanone (SAB-378); 3-[2-cyano-3-(trifluoromethyl)phenoxy]phenyl 4,4,4-trifluoro-1-butanesulfonic acid ester (BAY 59-3074); 3-(5'-cyano-1',1'-dimethylpentyl)-1-(4-N-morpholino-butyryloxy)-D8-tetrahydrocannabinol hydrochloride (0-1057); delta-9-tetrahydrocannabinol (GW-1000); Butenedioic acid (2E)-, mono[5-(1,1-dimethylheptyl)-2-[(1S,2S,5S)-6,6-dimethyl-4-oxobicyclo[3.1.1]hept-2-yl]-3-hydroxyphenyl]ester (PRS-211375); PRS-211359; PRS-211355; 3-(4-tert-Butyl-2,6-dihydroxy-benzyl)-4-isopropenyl-cyclohexanone (PRS-211096); 2-(2,4-dichloro-phenylamino)-4-trifluoromethyl-pyrimidine-5-carboxylic acid (tetrahydro-pyran-4-ylmethyl)-amide (GW-842166X); and mixtures thereof;

wherein the $CB_2$ agonist is selected from the group consisting of: (6ar,10ar)-3-(1,1-dimethylheptyl)-1-methoxy-6,6,9-trimethyl-6a,7,10,10a-tetrahydro-6H-enzo[c]chromene (L759633); (6ar,10ar)-3-(1,1-dimethylheptyl)-1-methoxy-6,6-dimethyl-9-methylene-6a,7,8,9,10,10a-hexahydro-6H-benzo[c]chromene (L759656); {4-[4-(1,1-dimethyl-heptyl)-2,6-dimethoxy-phenyl]-6,6-dimethyl-bicyclo-[3.1.1]hept-2-en-2-yl}-methanol (HU308); (2-Methyl-1-propyl-1H-indol-3-yl)-1-naphthalenylmethanone (JWH015); (2-iodo-5-nitro-phenyl)-[1-(1-methyl-piperidin-2-ylmethyl)-1H-indol-3-yl]- -methanone (AM-1241); 3-(1,1-dimethyl-butyl)-6,6,9-trimethyl-6a,7,10,10a-tetrahydro-6H-benzo[c]-chromene (JWH133); 6,6,9-trimethyl-3-pentyl-6a,7,8,10a-tetrahydro-6H-benzo[c]chromen-1-ol; dronabinol; 5-(1,1-dimethyl-heptyl)-2-[5-hydroxy-2-(3-hydroxy-propyl)-cyclohexyl]-phenol (CP-55,940); (2-methyl-3-morpholin-4-ylmethyl-3,4-dihydro-5-oxa-2a-aza-acenaphthylen-1-yl)-naphthalen-1-yl-methanone (WIN-55,212-2); (6aR,10aR)-9-(Hydroxymethyl)-6,6-dimethyl-3-(2-methyloctan-2-yl)-6a,7,10,10a-tetrahydrobenzo[c]chromen-1-ol (HU210); arachidonyl-2-chloroethylamid (ACEA); arachidonylcyclopropylamide (ACPA); methanandamide; anandamide; 2-arachidonoyl glycerol; 2-icosa-5,8,11,14-tetraenyloxy-propane-1,3-diol (noladinether); (−)-(R)-3-(2-Hydroxymethylindanyl-4-oxy)phenyl-4,4,4-trifluorobutyl-1-sulfonate (BAY 38-7271); naphthalen-1-yl-(4-pentyloxynaphthalen-1-yl)methanone (SAB-378); 3-[2-cyano-3-(trifluoromethyl)phenoxy]phenyl 4,4,4-trifluoro-1-butanesulfonic acid ester (BAY 59-3074); 3-(5'-cyano-1',1'-dimethylpentyl)-1-(4-N-morpholino-butyryloxy)-D8-tetrahydrocannabinol hydrochloride (0-1057); delta-9-tetrahydrocannabinol (GW-1000); Butenedioic acid (2E)-, mono[5-(1,1-dimethylheptyl)-2-[(1S,2S,5S)-6,6-dimethyl-4-oxobicyclo[3.1.1]hept-2-yl]-3-hydroxyphenyl]ester (PRS-211375); PRS-211359; PRS-211355; 3-(4-tert-Butyl-2,6-dihydroxy-benzyl)-4-isopropenyl-cyclohexanone (PRS-211096); 2-(2,4-dichloro-phenylamino)-4-trifluoromethyl-pyrimidine-5-carboxylic acid (tetrahydro-pyran-4-ylmethyl)-amide (GW-842166X); and mixtures thereof;

wherein the $CB_2$ antagonist is selected from the group consisting of: N-{1,3,3-trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide (SR-144528), N-(1,3-Benzodioxol-5-ylmethyl)-1,2-dihydro-7-methoxy-2-oxo-8-(pentyloxy)-3-quinolinecarboxamide (JTE-907), 6-Iodo-2-methyl-1-[2-(4-morpholinyl)ethyl]-1H-indol-3-yl](4-methoxyphenyl)methanone (AM630), and mixtures thereof;

wherein the $CB_2$ inverse agonist is selected from the group consisting of: N-{1,3,3-trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide (SR-144528), N-(1,3-Benzodioxol-5-ylmethyl)-1,2-dihydro-7-methoxy-2-oxo-8-(pentyloxy)-3-quinolinecarboxamide (JTE-907), 6-Iodo-2-methyl-1-[2-(4-morpholinyl)ethyl]-1H-indol-3-yl](4-methoxyphenyl)methanone (AM630), and mixtures thereof; and wherein the compounds having both $CB_1$ agonist and $CB_2$ agonist properties is selected from the group consisting of: dronabinol; (6aR,10aR)-9-(Hydroxymethyl)-6,6-dimethyl-3-(2-methyloctan-2-yl)-6a,7,10,10a-tetrahydrobenzo[c]chromen-1-ol (HU210); 2-icosa-5,8,11,14-tetraenyloxy-propane-1,3-diol (noladinether); and mixtures thereof.

7. The method of claim 6 wherein the metabolic syndrome comprises disorders selected from the group consisting of: hypertension; insulin resistance; glucose intolerance; and dyslipoproteinaemia.

8. The method of claim 6 wherein (a) the $K_{ATP}$ channel modulator also functions as a $CB_x$ modulator; or (b) the $CB_x$ modulator also functions as a $K_{ATP}$ channel modulator; provided that the $K_{ATP}$ channel modulator and the $CB_x$ modulator are different compounds.

9. A method of treating a medical condition in a subject in need thereof comprising the steps of: administering to the subject therapeutically effective amounts of both a $K_{ATP}$ channel modulator, which exhibits an $IC_{50}$ value [μmol] of less than about 50 when binding to SURy subunits, wherein y is 1, 2A, or 2B; and a $CB_x$ modulator, which exhibits an $IC_{50}$ value [μmol] greater than about 50 when binding to the $CB_1$ receptor or $CB_2$ receptor; wherein the $CB_x$ modulator is selected from the group consisting of: $CB_1$ agonists, $CB_2$ agonists, $CB_2$ antagonists, $CB_2$ inverse agonists, compounds having both $CB_1$ agonist and $CB_2$ agonist properties, and mixtures thereof; and wherein the medical condition is selected from the group consisting of: obesity, diabetes mellitus type I and II, metabolic syndrome, insulinoma, familial hyperinsulemic hypoglycemia, male pattern baldness, detrusor hyperreactivity, asthma, epilepsy, analgesia, angina, arrhythmia, coronary spasm, peripheral vascular disease, cerebral vasospasm, appetite regulation, pain, neuropathic pain, chronic pain, idiopathic pain and impotence;

wherein the $K_{ATP}$ channel modulator is selected from a group consisting of: 3-(1,1-dimethyl-butyl)-6,6,9-trimethyl-6a,7,10,10a-tetrahydro-6H-benzo[c]-chromene; N-{1,3,3-trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide; (2-iodo-5-nitro-phenyl)-[1-(1-methyl-piperidin-2-ylmethyl)-1H-indol-3-yl]-methanone; {4-[4-(1,1-dimethyl-heptyl)-2,6-dimethoxy-phenyl]-6,6-dimethyl-bicyclo[3.1.1]hept-2-en-2-yl}-methanol; 3-(1,1-dimethyl-heptyl)-9-hydroxymethyl-6,6-dimethyl-6a,7,10,10a-tetrahydro-6H-enzo[c]chromen-1-ol; icosa-5,8,11,14-tetraenoic acid 2-hydroxy-1-hydroxymethyl-ethyl ester; 1-aziridin-1-yl-henicosa-6,9,12,15-tetraen-2-one; noladineether; 4,4,4-trifluoro-butane-1-sulfinic acid 3-(2-hydroxymethyl-indan-4-yloxy)-phenyl ester; 7-methoxy-2-oxo-8-pentyloxy-1,2-dihydro-quinoline-3-carboxylic acid (benzo[1,3]dioxol-5-ylmethyl)-amide; N-(1-{-4-[4-chloro-2-(2-fluoro-benzenesulfonyl)-benzenesulfonyl]-phenyl}-ethyl)-methanesulfonamide; [6-iodo-2-methyl-1-(2-morpholin-4-yl-ethyl)-2,3-dihydro-1H-indol-3-yl]-(4-methoxy-phenyl)-methanone; 1-(4-chloro-phenyl)-2-(2-chloro-phenyl)-5-ethyl-1H-imidazole-4-carboxylic acid piperidin-1-ylamide; (2-methyl-1-propyl-2,3-dihydro-1H-indol-3-yl)-naphthalen-1-yl-methanone; 5-(1,1-dimethyl-heptyl)-2-[5-hydroxy-2-(3-hydroxy-propyl)-cyclohexyl]-phenol; (2-methyl-3-morpholin-4-ylmethyl-3,4-dihydro-5-oxa-2a-azacenaphthylen-1-yl)-naphthalen-1-yl-methanone; 5-(4-chloro-phenyl)-1-(2,4-dichloro-phenyl)-4-methyl-1H-pyrazole-3-carboxylic acid piperidin-1-ylamide; 5-(4-bromo-phenyl)-1-(2,4-dichloro-phenyl)-4-ethyl-1H-pyrazole-3-carboxylic acid piperidin-1-ylamide; 1-[bis-(4-chloro-phenyl)-methyl]-3-[(3,5-difluoro-phenyl)-methanesulfonyl-methylene]-azetidine; 4-chloro-N-{[3-(4-chloro-phenyl)-4-phenyl-4,5-dihydro-pyrazol-1-yl]-methylamino-methylene}-benzenesulfonamide; N-{amino-[3-(4-chloro-phenyl)-4-phenyl-4,5-dihydro-pyrazol-1-yl]-methylene}-4-chloro-benzenesulfonamide; N-{[3-(4-chloro-phenyl)-4-pyridin-3-yl-4,5-dihydro-pyrazol-1-yl]-methylamino-methylene}-4-trifluoromethyl-benzenesulfonamide; 4-Chloro-N-{[3-(4-chloro-phenyl)-4-pyridin-3-yl-4,5-dihydro-pyrazol-1-yl]-methylamino-methylene}-benzenesulfonamide; 4-chloro-N-{[3-(4-chloro-phenyl)-4-(3-fluoro-phenyl)-4,5-dihydro-pyrazol-1-yl]-methoxyamino-methylene}-benzenesulfonamide; morpholine-4-sulfonic acid [3-(4-chloro-phenyl)-4-phenyl-4,5-dihydro-pyrazol-1-yl]-methylamino-methyleneamide; N-{[3-(4-chloro-phenyl)-4-(3-fluoro-phenyl)-4,5-dihydro-pyrazol-1-yl]-methylamino-methylene}-N,N-dimethyl-sulfonamide; azepane-1-sulfonic acid [3-(4-chloro-phenyl)-4-phenyl-4,5-dihydro-pyrazol-1-yl]-methylamino-methyleneamide; 4-chloro-N-{[3-(4-chloro-phenyl)-4-phenyl-4,5-dihydro-pyrazol-1-yl]-[(1-methyl-pyrrolidin-3-ylmethyl)-amino]-methylene}-benzenesulfonamide; 1-(4-chloro-phenyl)-5-phenyl-4,5-dihydro-1H-pyrazole-3-carboxamidine; N-{[3-(4-chloro-phenyl)-4-phenyl-4,5-dihydro-pyrazol-1-yl]-methylamino-methylene}-4-trifluoromethyl-benzene-sulfonamide; piperidine-1-sulfonic acid [3-(4-chloro-phenyl)-4-phenyl-4,5-dihydro-pyrazol-1-yl]-methylamino-methyleneamide; piperidine-1-sulfonic acid [3-(4-chloro-phenyl)-4-phenyl-4,5-dihydro-pyrazol-1-yl]-(2-dimethylamino-ethylamino)-methyleneamide; N,N-diethylamino-1-sulfonic acid [3-(4-chloro-phenyl)-4-phenyl-4,5-dihydro-pyrazol-1-yl]-methylsulfanyl-methyleneamide; 2-amino-1-[3-(4-chloro-phenyl)-4-phenyl-4,5-dihydro-pyrazol-1-yl]-3-(3,4-dichloro-phenyl)-propan-1-one; N,N-dimethylamino-1-sulfonic acid [3-(4-chloro-phenyl)-4-phenyl-4,5-dihydro-pyrazol-1-yl]-(2-fluoro-ethylamino)-methyleneamide; piperidine-1-sulfonic acid [3-(4-chloro-phenyl)-4-(3-fluoro-phenyl)-4,5-dihydro-pyrazol-1-yl]-methylamino-methyleneamide; 5-(4-chloro-phenyl)-1-(2,4-dichloro-phenyl)-4,5-dihydro-1H-pyrazole-3-carboxylic acid piperidine-1-ylamide; 1-(4-chloro-phenyl)-5-phenyl-4,5-dihydro-1H-pyrazole-3-carboxylic acid piperidin-1-ylamide; piperidine-1-sulfonic acid [1-(4-chloro-phenyl)-5-phenyl-4,5-dihydro-1H-pyrazol-3-yl]-methylamino-methyleneamide; morpholine-4-sulfonic acid [1-(2,4-dichloro-phenyl)-5-phenyl-4,5-dihydro-1H-pyrazol-3-yl]-methylamino-methyleneamide; 4-chloro-N-[[3-(4-chloro-phenyl)-4-phenyl-4,5-dihydro-pyrazol-1-yl]-(2-fluoro-ethylamino)-methylene]-benzenesulfonamide; 4-chloro-N-[3-(4-chloro-phenyl)-4-phenyl-4,5-dihydro-pyrazole-1-carbonyl]-benzenesulfonamide; 4-chloro-N-[[3-(4-chloro-phenyl)-4-phenyl-4,5-dihydro-pyrazol-1-yl]-(2-ethylamino-ethylamino)-methylene]-benzenesulfonamide; 4-chloro-N-{[3-(4-chloro-phenyl)-4-phenyl-4,5-dihydro-pyrazol-1-yl]-[(1-methyl-pyrrolidin-2-ylmethyl)-amino]-methylene}-benzenesulfonamide; 4-chloro-N-[[3-(4-chloro-phenyl)-4-phenyl-4,5-dihydro-pyrazol-1-yl]-(4-pyrrolidin-1-yl-butylamino)-methylene]-benzenesulfonamide; 4-chloro-N-{[3-(4-chloro-phenyl)-4-phenyl-4,5-dihydro-pyrazol-1-yl]-[(pyridin-3-ylmethyl)-amino]-methylene}-benzenesulfonamide; 1-[3-(4-chloro-phenyl)-4-phenyl-4,5-dihydro-pyrazol-1-yl]-3-(1H-indol-2-y-l)-2-methylamino-propan-1-one; 2-[3-(4-chloro-phenyl)-4-phenyl-4,5-dihydro-pyrazol-1-yl]-5-ethyl-4,5-dihydro-oxazole; 4-chloro-N-[[3-(4-chloro-phenyl)-4-phenyl-4,5-dihydro-pyrazol-1-yl]-(3-hydroxy-2,2-dimethyl-propylamino)-methylene]-benzenesulfonamide; N,N-diethylamino-1-sulfonic acid [3-(4-chloro-phenyl)-4-hydroxy-4-phenyl-4,5-dihydro-pyrazol-1-yl]-methylamino-methyleneamide; 5-(4-bromo-phenyl)-1-(2,4-dichloro-phenyl)-1H-pyrazole-3-carbonitrile; 8-chloro-1-(2,4-dichloro-phenyl)-1,3a,4,5,6,10b-hexahydro-1,2-diazabenzo[e]azulene-3-carboxylic acid piperidin-1-ylamide; 5-(4-bromo-phenyl)-1-(2,4-dichloro-phenyl)-3-[2-(3,5-difluoro-phenyl)-2-methanesulfonyl-vinyl]-4-methyl-1H-pyrazole; piperidine-1-carboxylic acid [5-(4-chloro-phenyl)-1-(2,4-dichloro-phenyl)-4-methyl-1H-pyrazol-3-yl]-amide; 1-(4-chloro-phenyl)-2-(2,4-dichloro-phenyl)-5-ethylsulfanyl-1H-imidazole-4-carboxylic acid piperidin-1-ylamide; 2-(2,4-dichloro-phenyl)-1-(4-trifluoromethyl-phenyl)-1H-imidazole-4-carboxylic acid piperidin-1-ylamide; 1-(4-chloro-phenyl)-2-(2,4-dichloro-phenyl)-5-methylsulfanyl-1H-imidazole-4-carboxylic acid piperidin-1-ylamide; 1-(4-chloro-phenyl)-2-(2,4-dichloro-phenyl)-1H-imidazole-4-carboxylic acid piperidin-1-ylamide; 1-(4-chloro-phenyl)-2-(2,4-dichloro-phenyl)-5-ethyl-1H-imidazole-4-carboxylic acid piperidin-1-ylamide; 1-(4-bromo-phenyl)-2-(2,4-dichloro-phenyl)-5-ethyl-1H-imidazole-4-carboxylic acid piperidin-1-ylamide; 1-(4- bromo-phenyl)-5-chloro-2-(2,4-dichloro-phenyl)-1H-imidazole-4-carboxylic acid piperidin-1-ylamide; 1-(4-bromo-phenyl)-2-(2,4-dichloro-phenyl)-5-ethyl-1H-imidazole-4-carboxylic acid cyclohexylamide; 1-(4-bromo-phenyl)-2-(2,4-dichloro-phenyl)-5-ethyl-1H-imidazole-4-carboxylic acid pentylamide; 4-(4-chloro-phenyl)-5-(2,4-dichloro-phenyl)-1-methyl-1H-imidazole-2-carboxylic acid cyclohexylamide; 4-(4-chloro-phenyl)-5-(2,4-dichloro-phenyl)-3-methyl-1H-imidazole-2-carboxylic acid cyclohexylamide; 1-(5-chloro-pyridin-2-yl)-2-(2,4-dichloro-phenyl)-5-ethyl-1H-imidazole-4-carboxylic acid piperidin-1-ylamide; 1-(4-chloro-phenyl)-2-(2,4-dichloro-phenyl)-5-methyl-1H-imidazole-4-carboxylic acid (4-hydroxy-cyclohexyl)-amide; 1-(4-chloro-phenyl)-2-(2,4-dichloro-phenyl)-5-methyl-1H-imidazole-4-carboxylic acid azepan-1-ylamide; 2-(2,4-dichloro-phenyl)-5-ethyl-1-phenyl-1H-imidazole-4-carboxylic acid piperidin-1-ylamide; 2-(1,5-dimethyl-1H-pyrrol-2-yl)-5-ethyl-1-phenyl-1H-imidazole-4-carboxylic acid cyclohexylamide; 1-(4-chloro-phenyl)-5-ethyl-2-(3-methyl-pyridin-2-yl)-1H-imidazole-4-carboxylic acid piperidin-1-ylamide; 1-(4-chloro-phenyl)-5-ethyl-2-(3-methyl-pyridin-2-yl)-1H-imidazole-4-carboxylic acid cyclohexylamide; 1-(4-chloro-phenyl)-2-(2,4-dichloro-phenyl)-5-methyl-1H-imidazole-4-carboxylic acid (4-trifluoromethyl-phenyl)-amide; 2-(2,4-dichloro-phenyl)-5-methyl-1-pyridin-2-yl-1H-imidazole-4-carboxylic acid piperidin-1-ylamide; 1-(4-chloro-phenyl)-2-(2,4-dichloro-phenyl)-5-fluoromethyl-1H-imidazole-4-carboxylic acid piperidin-1-ylamide; 1-(4-chloro-phenyl)-2-(2,4-dichloro-phenyl)-5-hydroxymethyl-1H-imidazole-4-carboxylic acid piperidin-1-ylamide; 1-(4-chloro-phenyl)-2-(2,4-dichloro-phenyl)-5-methylsulfanyl-1H-imidazole-4-carboxylic acid cyclohexylamide; 1-(4-chloro-phenyl)-2-(2,4-dichloro-phenyl)-5-methanesulfonyl-1H-imidazole-4-carboxylic acid piperidin-1-ylamide; 1-(4-chloro-phenyl)-2-(2,4-dichloro-phenyl)-5-methanesulfinyl-1H-imidazole-4-carboxylic acid piperidin-1-ylamide; 5-(4-chloro-phenyl)-4-(2,5-dichloro-phenyl)-1-methyl-1H-imidazole-2-carboxylic acid piperidin-1-ylamide; 2-(2-chloro-phenyl)-1-(5-chloro-pyridin-2-yl)-5-ethyl-1H-imidazole-4-carboxylic acid piperidin-1-ylamide; 1-(4-chloro-phenyl)-2-(2,4-dichloro-phenyl)-5-(2,2,2-trifluoroethyl)-1H-imidazole-4-carboxylic acid piperidin-1-ylamide; N-[1-(4-chloro-phenyl)-2-(2,4-dichloro-phenyl)-5-methyl-1H-imidazol-4-yl]-benzamide; 1-(4-chloro-phenyl)-2-(2,4-dichloro-phenyl)-5-pyrrolidin-1-ylmethyl-1H-imidazole-4-carboxylic acid piperidin-1-ylamide; 2-[1-(4-chloro-phenyl)-2-(2,4-dichloro-phenyl)-5-methyl-1H-imidazol-4-yl]-hexan-2-ol; 1-(4-chloro-phenyl)-2-(2,4-dichloro-phenyl)-5-methyl-4-pentyl-1H-imidazole; 2,5-dimethyl-1-phenyl-1H-imidazole-4-carboxylic acid adamantan-2-ylamide; 1-(4-chloro-phenyl)-2-(2-chloro-phenyl)-5-methylsulfanyl-1H-imidazole-4-carboxylic acid piperidin-1-ylamide; 2-(2-chloro-phenyl)-1-(4-trifluoromethyl-phenyl)-1H-imidazole-4-carboxylic acid piperidin-1-ylamide; 5-(4-chloro-phenyl)-1-(2,4-dichloro-phenyl)-1H-[1,2,4]triazole-3-carboxylic acid pyrrolidin-1-ylamide; 1-(4-chloro-phenyl)-5-(2,4-dichloro-phenyl)-1H-[1,2,4]triazole-3-carboxylic acid piperidin-1-yl-amide; 1-{(4-chloro-benzene-sulfonylimino)-[3-(4-chloro-phenyl)-4-phenyl-4,5-dihydro-pyrazol-1-yl]-methyl}-piperidine-4-carboxylic acid amide; 4-chloro-N-{[3-(4-chloro-phenyl)-4-phenyl-4,5-dihydro-pyrazol-1-yl]-[2-(2-oxo-pyrrolidin-1-yl)-ethylamino]-methylene}-benzenesulfonamide; 4-chloro-N-[[3-(4-chloro-phenyl)-4-phenyl-4,5-dihydro-pyrazol-1-yl]-(2-cyano-ethylamino)-methylene]-benzene-sulfonamide; 4-chloro-N-[[3-(4-chloro-phenyl)-4-phenyl-4,5-dihydro-pyrazol-1-yl]-(methoxy-methylamino)-methylene]-benzenesulfonamide; 4-chloro-N-{[3-(4-chloro-phenyl)-4-phenyl-4,5-dihydro-pyrazol-1-yl]-[(piperidin-4-ylmethyl)-amino]-methylene}-benzenesulfonamide; 4-chloro-N-[[3-(4-chloro-phenyl)-4-phenyl-4,5-dihydro-pyrazol-1-yl]-(piperidin-4-ylamino)-methylene]-benzenesulfonamide; morpholine-4-sulfonic acid [3-(4-chloro-phenyl)-4-phenyl-4,5-dihydro-pyrazol-1-yl]-(cyclopropyl-methylamino)-methyleneamide; 1-{(4-chloro-benzene-sulfonylimino)-[3-(4-chloro-phenyl)-4-phenyl-4,5-dihydro-pyrazol-1-yl]-methyl}-piperidine-4-carboxylic acid amide; morpholine-4-sulfonic acid [3-(4-chloro-phenyl)-4-phenyl-4,5-dihydro-pyrazol-1-yl]-(cyclopropyl-methylamino)-methyleneamide; pinacidil; cromakalim; diazoxide; 1-(4-(1H-imidazol-1-yl)benzoyl)-N-methylcyclobutanecarbothioamide (MCC-134); 4-(2-cyanimino-1,2-dihydropyrid-1-yl)-2,2-dimethyl-6-nitrochromene (SR 47063); R-4-[3,4-dioxo-2-(1,2,2-trimethyl-propylamino)-cyclobut-1-1-enylamino]-3-methoxybenzonitrile (WAY 135201); and mixtures thereof;

wherein the CB$_1$ agonist is selected from the group consisting of: (6ar,10ar)-3-(1,1-dimethylheptyl)-1-methoxy-6,6,9-trimethyl-6a,7,10,10a-tetrahydro-6H-enzo[c]chromene (L759633); (6ar,10ar)-3-(1,1-dimethylheptyl)-1-methoxy-6,6-dimethyl-9-methylene-6a,7,8,9,10,10a-hexahydro-6H-benzo[c]chromene (L759656); {4-[4-(1,1-dimethyl-heptyl)-2,6-dimethoxy-phenyl]-6,6-dimethyl-bicyclo-[3.1.1]hept-2-en-2-yl}-methanol (HU308); (2-Methyl-1-propyl-1H-indol-3-yl)-1-naphthalenylmethanone (JWH015); (2-iodo-5-nitro-phenyl)-[1-(1-methyl-piperidin-2-ylmethyl)-1H-indol-3-yl]--methanone (AM-1241); 3-(1,1-dimethyl-butyl)-6,6,9-trimethyl-6a,7,10,10a-tetrahydro-6H-benzo[c]-chromene (JWH133); 6,6,9-trimethyl-3-pentyl-6a,7,8,10a-tetrahydro-6H-benzo[c]chromen-1-ol; dronabinol; 5-(1,1-dimethyl-heptyl)-2-[5-hydroxy-2-(3-hydroxy-propyl)-cyclohexyl]-phenol (CP-55,940); (2-methyl-3-morpholin-4-ylmethyl-3,4-dihydro-5-oxa-2a-aza-acenaphthylen-1-yl)-naphthalen-1-yl-methanone (WIN-55,212-2); (6aR,10aR)-9-(Hydroxymethyl)-6,6-dimethyl-3-(2-methyloctan-2-yl)-6a,7,10,10a-tetrahydrobenzo[c]chromen-1-ol (HU210); arachidonyl-2-chloroethylamid (ACEA); arachidonylcyclopropylamide (ACPA); methanandamide; anandamide; 2-arachidonoyl glycerol; 2-icosa-5,8,11,14-tetraenyloxy-propane-1,3-diol (noladinether); (−)-(R)-3-(2-Hydroxymethylindanyl-4-oxy)phenyl-4,4,4-trifluorobutyl-1-sulfonate (BAY 38-7271); naphthalen-1-yl-(4-pentyloxynaphthalen-1-yl) methanone (SAB-378); 3-[2-cyano-3-(trifluoromethyl)phenoxy] phenyl 4,4,4-trifluoro-1-butanesulfonic acid ester (BAY 59-3074); 3-(5'-cyano-1',1'-dimethylpentyl)-1-(4-N-morpholino-butyryloxy)-D8-tetrahydrocannabinol hydrochloride (O-1057); delta-9-tetrahydrocannabinol (GW-1000); Butenedioic acid (2E)-, mono[5-(1,1-dimethylheptyl)-2-[(1S,2S,5S)-6,6-dimethyl-4-oxobicyclo[3.1.1]hept-2-yl]-3-hydroxyphenyl]ester (PRS-211375); PRS-211359; PRS-211355; 3-(4-tert-Butyl-2,6-dihydroxy-benzyl)-4-isopropenyl-cyclohexanone (PRS-211096); 2-(2,4-dichloro-phenylamino)-4-trifluoromethyl-pyrimidine-5-carboxylic acid (tetrahydro-pyran-4-ylmethyl)-amide (GW-842166X); and mixtures thereof;

wherein the $CB_2$ agonist is selected from the group consisting of: (6ar,10ar)-3-(1,1-dimethylheptyl)-1-methoxy-6,6,9-trimethyl-6a,7,10,10a-tetrahydro-6H-enzo[c]chromene (L759633); (6ar,10ar)-3-(1,1-dimethylheptyl)-1-methoxy-6,6-dimethyl-9-methylene-6a,7,8,9,10,10a-hexahydro-6H-benzo[c]chromene (L759656); {4-[4-(1,1-dimethyl-heptyl)-2,6-dimethoxy-phenyl]-6,6-dimethyl-bicyclo-[3.1.1]hept-2-en-2-yl}-methanol (HU308); (2-Methyl-1-propyl-1H-indol-3-yl)-1-naphthalenylmethanone (JWH015); (2-iodo-5-nitro-phenyl)-[1-(1-methyl-piperidin-2-ylmethyl)-1H-indol-3-yl]-1-methanone (AM-1241); 3-(1,1-dimethyl-butyl)-6,6,9-trimethyl-6a,7,10,10a-tetrahydro-6H-benzo[c]-chromene (JWH133); 6,6,9-trimethyl-3-pentyl-6a,7,8,10a-tetrahydro-6H-benzo[c]chromen-1-ol; dronabinol; 5-(1,1-dimethyl-heptyl)-2-[5-hydroxy-2-(3-hydroxy-propyl)-cyclohexyl]-phenol (CP-55,940); (2-methyl-3-morpholin-4-ylmethyl-3,4-dihydro-5-oxa-2a-aza-acenaphthylen-1-yl)-naphthalen-1-yl-methanone (WIN-55,212-2); (6aR,10aR)-9-(Hydroxymethyl)-6,6-dimethyl-3-(2-methyloctan-2-yl)-6a,7,10,10a-tetrahydrobenzo[c]chromen-1-ol (HU210); arachidonyl-2-chloroethylamid (ACEA); arachidonylcyclopropylamide (ACPA); methanandamide; anandamide; 2-arachidonoyl glycerol; 2-icosa-5,8,11,14-tetraenyloxy-propane-1,3-diol (noladinether); (−)-(R)-3-(2-Hydroxymethylindanyl-4-oxy)phenyl-4,4,4-trifluorobutyl-1-sulfonate (BAY 38-7271); naphthalen-1-yl-(4-pentyloxynaphthalen-1-yl)methanone (SAB-378); 3-[2-cyano-3-(trifluoromethyl)phenoxy]phenyl 4,4,4-trifluoro-1-butanesulfonic acid ester (BAY 59-3074); 3-(5'-cyano-1',1'-dimethylpentyl)-1-(4-N-morpholino-butyryloxy)-D8-tetrahydrocannabinol hydrochloride (O-1057); delta-9-tetrahydrocannabinol (GW-1000);

Butenedioic acid (2E)-, mono[5-(1,1-dimethylheptyl)-2-[(1S,2S,5S)-6,6-dimethyl-4-oxobicyclo[3.1.1]hept-2-yl]-3-hydroxyphenyl]ester (PRS-211375); PRS-211359; PRS-211355; 3-(4-tert-Butyl-2,6-dihydroxybenzyl)-4-isopropenyl-cyclohexanone (PRS-211096); 2-(2,4-dichloro-phenylamino)-4-trifluoromethyl-pyrimidine-5-carboxylic acid (tetrahydro-pyran-4-ylmethyl)-amide (GW-842166X); and mixtures thereof;

wherein the $CB_2$ antagonist is selected from the group consisting of: N-{1,3,3-trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide (SR-144528), N-(1,3-Benzodioxol-5-ylmethyl)-1,2-dihydro-7-methoxy-2-oxo-8-(pentyloxy)-3-quinolinecarboxamide (JTE-907), 6-Iodo-2-methyl-1-[2-(4-morpholinyl)ethyl]-1H-indol-3-yl](4-methoxyphenyl)methanone (AM630), and mixtures thereof;

wherein the $CB_2$ inverse agonist is selected from the group consisting of: N-{1,3,3-trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide (SR-144528), N-(1,3-Benzodioxol-5-ylmethyl)-1,2-dihydro-7-methoxy-2-oxo-8-(pentyloxy)-3-quinolinecarboxamide (JTE-907), 6-Iodo-2-methyl-1-[2-(4-morpholinyl)ethyl]-1H-indol-3-yl](4-methoxyphenyl)methanone (AM630), and mixtures thereof; and wherein the compounds having both $CB_1$ agonist and $CB_2$ agonist properties is selected from the group consisting of: dronabinol; (6aR,10aR)-9-(Hydroxymethyl)-6,6-dimethyl-3-(2-methyloctan-2-yl)-6a,7,10,10a-tetrahydrobenzo[c]chromen-1-ol (HU210); 2-icosa-5,8,11,14-tetraenyloxy-propane-1,3-diol (noladinether); and mixtures thereof.

10. The method according to claim 9 wherein the $K_{ATP}$ channel modulator and the $CB_x$ modulator are administered simultaneously in the same or different dosage form or sequentially in the same or different dosage form.

11. The method of claim 10 wherein the $K_{ATP}$ channel modulator and the $CB_x$ modulator are administered simultaneously in an oral dosage form.

12. The method of claim 9 wherein (a) the $K_{ATP}$ channel modulator also functions as a $CB_x$ modulator; or (b) the $CB_x$ modulator also functions as a $K_{ATP}$ channel modulator; provided that the $K_{ATP}$ channel modulator and the $CB_x$ modulator are different compounds.

13. The method of to claim 9 wherein the $K_{ATP}$ channel modulator modulates a channel selected from the group consisting of: the Kir6.2/SUR1 $K_{ATP}$ channel, the Kir6.2/SUR2B $K_{ATP}$ channel, the Kir6.1/SUR2B $K_{ATP}$ channel and the Kir6.2/SUR2A $K_{ATP}$ channel.

14. A pharmaceutical composition prepared by the process comprising the step of: combining a $K_{ATP}$ channel, having an $IC_{50}$ value [µmol] of less than about 50 when binding to SURy subunits, wherein y is 1, 2A, or 2B; with a $CB_x$ modulator having an $IC_{50}$ value [µmol] greater than about 50 when binding to the $CB_1$ receptor or $CB_2$ receptor; wherein the $CB_x$ modulator is selected from the group consisting of: $CB_1$ agonists, $CB_2$ agonists, $CB_2$ antagonists, $CB_2$ inverse agonists, compounds having both $CB_1$ agonist and $CB_2$ agonist properties, and mixtures thereof; and wherein the $K_{ATP}$ channel modulator and the $CB_x$ modulator are present in a combined amount effective for the treatment of a medical condition selected from the group consisting of obesity, diabetes mellitus type II and II, metabolic syndrome, insulinoma, familial hyperinsulemic hypoglycemia, male pattern baldness, detrusor hyperreactivity, asthma, epilepsy, analgesia, angina, arrhythmia, coronary spasm, peripheral vascular disease, cerebral vasospasm, appetite regulation, pain, neuropathic pain, chronic pain, idiopathic pain and impotence in mammals;

wherein the $K_{ATP}$ channel modulator is selected from a group consisting of: 3-(1,1-dimethyl-butyl)-6,6,9-trimethyl-6a,7,10,10a-tetrahydro-6H-benzo[c]-chromene; N-{1,3,3-trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide; (2-iodo-5-nitro-phenyl)-[1-(1-methyl-piperidin-2-ylmethyl)-1H-indol-3-yl]-methanone; {4-[4-(1,1-dimethyl-heptyl)-2,6-dimethoxy-phenyl]-6,6-dimethyl-bicyclo[3.1.1]hept-2-en-2-yl}-methanol; 3-(1,1-dimethyl-heptyl)-9-hydroxymethyl-6,6-dimethyl-6a,7,10,10a-tetrahydro-6H-enzo[c]chromen-1-ol; icosa-5,8,11,14-tetraenoic acid 2-hydroxy-1-hydroxymethyl-ethyl ester; 1-aziridin-1-yl-henicosa-6,9,12,15-tetraen-2-one;
noladineether; 4,4,4-trifluoro-butane-1-sulfinic acid 3-(2-hydroxymethyl-indan-4-yloxy)-phenyl ester; 7-methoxy-2-oxo-8-pentyloxy-1,2-dihydro-quinoline-3-carboxylic acid (benzo[1,3]dioxol-5-ylmethyl)-amide; N-(1-{-4-[4-chloro-2-(2-fluoro-benzenesulfonyl)-benzenesulfonyl]-phenyl}-ethyl)-methanesulfonamide; [6-iodo-2-methyl-1-(2-morpholin-4-yl-ethyl)-2,3-dihydro-1H-indol-3-yl]-(4-methoxy-phenyl)-methanone; 1-(4-chloro-phenyl)-2-

(2-chloro-phenyl)-5-ethyl-1H-imidazole-4-carboxylic acid piperidin-1-ylamide; (2-methyl-1-propyl-2,3-dihydro-1H-indol-3-yl)-naphthalen-1-yl-methanone; 5-(1,1-dimethyl-heptyl)-2-[5-hydroxy-2-(3-hydroxy-propyl)-cyclohexyl]-phenol; (2-methyl-3-morpholin-4-ylmethyl-3,4-dihydro-5-oxa-2a-azacenaphthylen-1-yl)-naphthalen-1-yl-methanone; 5-(4-chloro-phenyl)-1-(2,4-dichloro-phenyl)-4-methyl-1H-pyrazole-3-carboxylic acid piperidin-1-ylamide; 5-(4-bromo-phenyl)-1-(2,4-dichloro-phenyl)-4-ethyl-1H-pyrazole-3-carboxylic acid piperidin-1-ylamide; 1-[bis-(4-chloro-phenyl)-methyl]-3-[(3,5-difluoro-phenyl)-methanesulfonyl-methylene]-azetidine; 4-chloro-N-{[3-(4-chloro-phenyl)-4-phenyl-4,5-dihydro-pyrazol-1-yl]-methylamino-methylene}-benzenesulfonamide; N-{amino-[3-(4-chloro-phenyl)-4-phenyl-4,5-dihydro-pyrazol-1-yl]-methylene}-4-chloro-benzenesulfonamide; N-{[3-(4-chloro-phenyl)-4-pyridin-3-yl-4,5-dihydro-pyrazol-1-yl]-methylamino-methylene}-4-trifluoromethyl-benzenesulfonamide; 4-Chloro-N-{[3-(4-chloro-phenyl)-4-pyridin-3-yl-4,5-dihydro-pyrazol-1-yl]-methylamino-methylene}-benzenesulfonamide; 4-chloro-N-{[3-(4-chloro-phenyl)-4-(3-fluoro-phenyl)-4,5-dihydro-pyrazol-1-yl]-methoxyamino-methylene}-benzenesulfonamide; morpholine-4-sulfonic acid [3-(4-chloro-phenyl)-4-phenyl-4,5-dihydro-pyrazol-1-yl]-methylamino-methyleneamide; N-{[3-(4-chloro-phenyl)-4-(3-fluoro-phenyl)-4,5-dihydro-pyrazol-1-yl]-methylamino-methylene}-N,N-dimethyl-sulfonamide; azepane-1-sulfonic acid [3-(4-chloro-phenyl)-4-phenyl-4,5-dihydro-pyrazol-1-yl]-methylamino-methyleneamide; 4-chloro-N-{[3-(4-chloro-phenyl)-4-phenyl-4,5-dihydro-pyrazol-1-yl]-[(1-methyl-pyrrolidin-3-ylmethyl)-amino]-methylene}-benzenesulfonamide; 1-(4-chloro-phenyl)-5-phenyl-4,5-dihydro-1H-pyrazole-3-carboxamidine; N-{[3-(4-chloro-phenyl)-4-phenyl-4,5-dihydro-pyrazol-1-yl]-methylamino-methylene}-4-trifluoromethyl-benzene-sulfonamide; piperidine-1-sulfonic acid [3-(4-chloro-phenyl)-4-phenyl-4,5-dihydro-pyrazol-1-yl]-methylamino-methyleneamide; piperidine-1-sulfonic acid [3-(4-chloro-phenyl)-4-phenyl-4,5-dihydro-pyrazol-1-yl]-(2-dimethylamino-ethylamino)-methyleneamide; N,N-diethylamino-1-sulfonic acid [3-(4-chloro-phenyl)-4-phenyl-4,5-dihydro-pyrazol-1-yl]-methylsulfanyl-methyleneamide; 2-amino-1-[3-(4-chloro-phenyl)-4-phenyl-4,5-dihydro-pyrazol-1-yl]-3-(3,4-dichloro-phenyl)-propan-1-one; N,N-dimethylamino-1-sulfonic acid [3-(4-chloro-phenyl)-4-phenyl-4,5-dihydro-pyrazol-1-yl]-(2-fluoro-ethylamino)-methyleneamide; piperidine-1-sulfonic acid [3-(4-chloro-phenyl)-4-(3-fluoro-phenyl)-4,5-dihydro-pyrazol-1-yl]-methylamino-methyleneamide; 5-(4-chloro-phenyl)-1-(2,4-dichloro-phenyl)-4,5-dihydro-1H-pyrazole-3-carboxylic acid piperidine-1-ylamide; 1-(4-chloro-phenyl)-5-phenyl-4,5-dihydro-1H-pyrazole-3-carboxylic acid piperidin-1-ylamide; piperidine-1-sulfonic acid [1-(4-chloro-phenyl)-5-phenyl-4,5-dihydro-1H-pyrazol-3-yl]-methylamino-methyleneamide; morpholine-4-sulfonic acid [1-(2,4-dichloro-phenyl)-5-phenyl-4,5-dihydro-1H-pyrazol-3-yl]-methylamino-methyleneamide; 4-chloro-N-[[3-(4-chloro-phenyl)-4-phenyl-4,5-dihydro-pyrazol-1-yl]-(2-fluoro-ethylamino)-methylene]-benzenesulfonamide; 4-chloro-N-[3-(4-chloro-phenyl)-4-phenyl-4,5-dihydro-pyrazole-1-carbonyl]-benzenesulfonamide; 4-chloro-N-[[3-(4-chloro-phenyl)-4-phenyl-4,5-dihydro-pyrazol-1-yl]-(2-ethylamino-ethylamino)-methylene]-benzenesulfonamide; 4-chloro-N-{[3-(4-chloro-phenyl)-4-phenyl-4,5-dihydro-pyrazol-1-yl]-[(1-methyl-pyrrolidin-2-ylmethyl)-amino]-methylene}-benzenesulfonamide; 4-chloro-N-[[3-(4-chloro-phenyl)-4-phenyl-4,5-dihydro-pyrazol-1-yl]-(4-pyrrolidin-1-yl-butylamino)-methylene]-benzenesulfonamide; 4-chloro-N-{[3-(4-chloro-phenyl)-4-phenyl-4,5-dihydro-pyrazol-1-yl]-[(pyridin-3-ylmethyl)-amino]-methylene}-benzenesulfonamide; 1-[3-(4-chloro-phenyl)-4-phenyl-4,5-dihydro-pyrazol-1-yl]-3-(1H-indol-2-y-l)-2-methylamino-propan-1-one; 2-[3-(4-chloro-phenyl)-4-phenyl-4,5-dihydro-pyrazol-1-yl]-5-ethyl-4,5-dihydro-oxazole; 4-chloro-N-[[3-(4-chloro-phenyl)-4-phenyl-4,5-dihydro-pyrazol-1-yl]-(3-hydroxy-2,2-dimethyl-propylamino)-methylene]-benzenesulfonamide; N,N-diethylamino-1-sulfonic acid [3-(4-chloro-phenyl)-4-hydroxy-4-phenyl-4,5-dihydro-pyrazol-1-yl]-methylamino-methyleneamide; 5-(4-bromo-phenyl)-1-(2,4-dichloro-phenyl)-1H-pyrazole-3-carbonitrile; 8-chloro-1-(2,4-dichloro-phenyl)-1,3a,4,5,6,10b-hexahydro-1,2-diazabenzo[e]azulene-3-carboxylic acid piperidin-1-ylamide; 5-(4-bromo-phenyl)-1-(2,4-dichloro-phenyl)-3-[2-(3,5-difluoro-phenyl)-2-methanesulfonyl-vinyl]-4-methyl-1H-pyrazole; piperidine-1-carboxylic acid [5-(4-chloro-phenyl)-1-(2,4-dichloro-phenyl)-4-methyl-1H-pyrazol-3-yl]-amide; 1-(4-chloro-phenyl)-2-(2,4-dichloro-phenyl)-5-ethylsulfanyl-1H-imidazole-4-carboxylic acid piperidin-1-ylamide; 2-(2,4-dichloro-phenyl)-1-(4-trifluoromethyl-phenyl)-1H-imidazole-4-carboxylic acid piperidin-1-ylamide; 1-(4-chloro-phenyl)-2-(2,4-dichloro-phenyl)-5-methylsulfanyl-1H-imidazole-4-carboxylic acid piperidin-1-ylamide; 1-(4-chloro-phenyl)-2-(2,4-dichloro-phenyl)-1H-imidazole-4-carboxylic acid piperidin-1-ylamide; 1-(4-chloro-phenyl)-2-(2,4-dichloro-phenyl)-5-ethyl-1H-imidazole-4-carboxylic acid piperidin-1-ylamide; 1-(4-bromo-phenyl)-2-(2,4-dichloro-phenyl)-5-ethyl-1H-imidazole-4-carboxylic acid piperidin-1-ylamide; 1-(4-bromo-phenyl)-5-chloro-2-(2,4-dichloro-phenyl)-1H-imidazole-4-carboxylic acid piperidin-1-ylamide; 1-(4-bromo-phenyl)-2-(2,4-dichloro-phenyl)-5-ethyl-1H-imidazole-4-carboxylic acid cyclohexylamide; 1-(4-bromo-phenyl)-2-(2,4-dichloro-phenyl)-5-ethyl-1H-imidazole-4-carboxylic acid pentylamide; 4-(4-chloro-phenyl)-5-(2,4-dichloro-phenyl)-1-methyl-1H-imidazole-2-carboxylic acid cyclohexylamide; 4-(4-chloro-phenyl)-5-(2,4-dichloro-phenyl)-3-methyl-1H-imidazole-2-carboxylic acid cyclohexylamide; 1-(5-chloro-pyridin-2-yl)-2-(2,4-dichloro-phenyl)-5-ethyl-1H-imidazole-4-carboxylic acid piperidin-1-ylamide; 1-(4-chloro-phenyl)-2-(2,4-dichloro-phenyl)-5-methyl-1H-imidazole-4-carboxylic acid (4-hydroxy-cyclohexyl)-amide; 1-(4-chloro-phenyl)-2-(2,4-dichloro-phenyl)-5-methyl-1H-imidazole-4-carboxylic acid azepan-1-ylamide; 2-(2,4-dichloro-phenyl)-5-ethyl-1-phenyl-1H-imidazole-4-carboxylic acid piperidin-1-ylamide; 2-(1,5-dimethyl-1H-pyrrol-2-yl)-5-ethyl-1-phenyl-1H-imidazole-4-carboxylic acid cyclohexylamide; 1-(4-chloro-phenyl)-5-ethyl-2-(3-methyl-pyridin-2-yl)-1-(4-imidazole-4-carboxylic acid piperidin-1-ylamide; 1-(4-chloro-phenyl)-5-ethyl-2-(3-methyl-pyridin-2-yl)-1H-imidazole-4-carboxylic acid cyclohexylamide; 1-(4-chloro-phenyl)-2-(2,4-dichloro-phenyl)-5-methyl-1H-imidazole-4-carboxylic acid (4-trifluoromethyl-phenyl)-amide; 2-(2,4-dichloro-phenyl)-5-methyl-1-pyridin-2-yl-1H-imidazole-4-carboxylic acid piperidin-1-ylamide; 1-(4-chloro-phenyl)-2-(2,4-dichloro-phenyl)-5-fluoromethyl-1H-imidazole-4-carboxylic acid piperidin-1-ylamide; 1-(4-chloro-phenyl)-2-(2,4-dichloro-phenyl)-5-hydroxymethyl-1H-imidazole-4-carboxylic acid piperidin-1-ylamide; 1-(4-chloro-phenyl)-2-(2,4-dichloro-phenyl)-5-methylsulfanyl-1H-imidazole-4-carboxylic acid cyclohexylamide; 1-(4-chloro-phenyl)-2-(2,4-dichloro-phenyl)-5-methanesulfonyl-1H-imidazole-4-carboxylic acid piperidin-1-ylamide; 1-(4-chloro-phenyl)-2-(2,4-dichloro-phenyl)-5-methanesulfinyl-1H-imidazole-4-carboxylic acid piperidin-1-ylamide; 5-(4-chloro-phenyl)-4-(2,5-dichloro-phenyl)-1-methyl-1H-imidazole-2-carboxylic acid piperidin-1-ylamide; 2-(2-chloro-phenyl)-1-(5-chloro-pyridin-2-yl)-5-ethyl-1H-imidazole-4-carboxylic acid piperidin-1-ylamide; 1-(4-chloro-phenyl)-2-(2,4-dichloro-phenyl)-5-(2,2,2-trifluoroethyl)-1H-imidazole-4-carboxylic acid piperidin-1-ylamide; N-[1-(4-chloro-phenyl)-2-(2,4-dichloro-phenyl)-5-methyl-1H-imidazol-4-yl]-benzamide; 1-(4-chloro-phenyl)-2-(2,4-dichloro-phenyl)-5-pyrrolidin-1-ylmethyl-1H-imidazole-4-carboxylic acid piperidin-1-ylamide; 2-[1-(4-chloro-phenyl)-2-(2,4-dichloro-phenyl)-5-methyl-1H-imidazol-4-yl]-hexan-2-ol; 1-(4-chloro-phenyl)-2-(2,4-dichloro-phenyl)-5-methyl-4-pentyl-1H-imidazole; 2,5-dimethyl-1-phenyl-1H-imidazole-4-carboxylic acid adamantan-2-ylamide; 1-(4-chloro-phenyl)-2-(2-chloro-phenyl)-5-methylsulfanyl-1H-imidazole-4-carboxylic acid piperidin-1-ylamide; 2-(2-chloro-phenyl)-1-(4-trifluoromethyl-phenyl)-1H-imidazole-4-carboxylic acid piperidin-1-ylamide; 5-(4-chloro-phenyl)-1-(2,4-dichloro-phenyl)-1H-[1,2,4]triazole-3-carboxylic acid pyrrolidin-1-ylamide; 1-(4-chloro-phenyl)-5-(2,4-dichloro-phenyl)-1H-[1,2,4]triazole-3-carboxylic acid piperidin-1-yl-amide; 1-{(4-chloro-benzene-sulfonylimino)-[3-(4-chloro-phenyl)-4-phenyl-4,5-dihydro-pyrazol-1-yl]-methyl}-piperidine-4-carboxylic acid amide; 4-chloro-N-{[3-(4-chloro-phenyl)-4-phenyl-4,5-dihydro-pyrazol-1-yl]-[2-(2-oxo-pyrrolidin-1-yl)-ethylamino]-methylene}-benzenesulfonamide; 4-chloro-N-[[3-(4-chloro-phenyl)-4-phenyl-4,5-dihydro-pyrazol-1-yl]-(2-cyano-ethylamino)-methylene]-benzene-sulfonamide; 4-chloro-N-[[3-(4-chloro-phenyl)-4-phenyl-4,5-dihydro-pyrazol-1-yl]-(methoxy-methylamino)-methylene]-benzenesulfonamide; 4-chloro-N-{[3-(4-chloro-phenyl)-4-phenyl-4,5-dihydro-pyrazol-1-yl]-[(piperidin-4-ylmethyl)-amino]-methylene}-benzenesulfonamide; 4-chloro-N-[[3-(4-chloro-phenyl)-4-phenyl-4,5-dihydro-pyrazol-1-yl]-(piperidin-4-ylamino)-methylene]-benzenesulfonamide; morpholine-4-sulfonic acid [3-(4-chloro-phenyl)-4-phenyl-4,5-dihydro-pyrazol-1-yl]-(cyclopropyl-methylamino)-methyleneamide; 1-{(4-chloro-benzene-sulfonylimino)-[3-(4-chloro-phenyl)-4-phenyl-4,5-dihydro-pyrazol-1-yl]-methyl}-piperidine-4-carboxylic acid amide; morpholine-4-sulfonic acid [3-(4-chloro-phenyl)-4-phenyl-4,5-dihydro-pyrazol-1-yl]-(cyclopropyl-methylamino)-methyleneamide; pinacidil; cromakalim; diazoxide; 1-(4-(1H-imidazol-1-yl)benzoyl)-N-methylcyclobutanecarbothioamide (MCC-134); 4-(2-cyanimino-1,2-dihydropyrid-1-yl)-2,2-dimethyl-6-nitrochromene (SR 47063); R-4-[3,4-dioxo-2-(1,2,2-trimethyl-propylamino)-cyclobut-1-1-enylamino]-3-methoxybenzonitrile (WAY 135201); and mixtures thereof;

wherein the $CB_1$ agonist is selected from the group consisting of: (6ar,10ar)-3-(1,1-dimethylheptyl)-1-methoxy-6,6,9-trimethyl-6a,7,10,10a-tetrahydro-6H-enzo[c]chromene (L759633); (6ar,10ar)-3-(1,1-dimethylheptyl)-1-methoxy-6,6-dimethyl-9-methylene-6a,7,8,9,10,10a-hexahydro-6H-benzo[c]chromene (L759656); {4-[4-(1,1-dimethyl-heptyl)-2,6-dimethoxy-phenyl]-6,6-dimethyl-bicyclo-[3.1.1]hept-2-en-2-yl}-methanol (HU308); (2-Methyl-1-propyl-1H-indol-3-yl)-1-naphthalenylmethanone (JWH015); (2-iodo-5-nitro-phenyl)-[1-(1-methyl-piperidin-2-ylmethyl)-1H-indol-3-yl]-methanone (AM-1241); 3-(1,1-dimethyl-butyl)-6,6,9-trimethyl-6a,7,10,10a-tetrahydro-6H-benzo[c]-chromene (JWH133); 6,6,9-trimethyl-3-pentyl-6a,7,8,10a-tetrahydro-6H-benzo[c]chromen-1-ol; dronabinol; 5-(1,1-dimethyl-heptyl)-2-[5-hydroxy-2-(3-hydroxy-propyl)-cyclohexyl]-phenol (CP-55,940); (2-methyl-3-morpholin-4-ylmethyl-3,4-dihydro-5-oxa-2a-aza-acenaphthylen-1-yl)-naphthalen-1-yl-methanone (WIN-55,212-2); (6aR,10aR)-9-(Hydroxymethyl)-6,6-dimethyl-3-(2-methyloctan-2-yl)-6a,7,10,10a-tetrahydrobenzo[c]chromen-1-ol (HU210); arachidonyl-2-chloroethylamid (ACEA); arachidonylcyclopropylamide (ACPA); methanandamide; anandamide; 2-arachidonoyl glycerol; 2-icosa-5,8,11,14-tetraenyloxy-propane-1,3-diol (noladinether); (−)-(R)-3-(2-Hydroxymethylindanyl-4-oxy)phenyl-4,4,4-trifluorobutyl-1-sulfonate (BAY 38-7271); naphthalen-1-yl-(4-pentyloxynaphthalen-1-yl)methanone (SAB-378); 3-[2-cyano-3-(trifluoromethyl)phenoxy]phenyl 4,4,4-trifluoro-1-butanesulfonic acid ester (BAY 59-3074); 3-(5'-cyano-1',1'-dimethylpentyl)-1-(4-N-morpholino-butyryloxy)-D8-tetrahydrocannabinol hydrochloride (O-1057); delta-9-tetrahydrocannabinol (GW-1000); Butenedioic acid (2E)-, mono[5-(1,1-dimethylheptyl)-2-[(1S,2S,5S)-6,6-dimethyl-4-oxobicyclo[3.1.1]hept-2-yl]-3-hydroxyphenyl]ester (PRS-211375); PRS-211359; PRS-211355; 3-(4-tert-Butyl-2,6-dihydroxy-benzyl)-4-isopropenyl-cyclohexanone (PRS-211096); 2-(2,4-dichloro-phenylamino)-4-trifluoromethyl-pyrimidine-5-carboxylic acid (tetrahydro-pyran-4-ylmethyl)-amide (GW-842166X); and mixtures thereof;

wherein the $CB_2$ agonist is selected from the group consisting of: (6ar,10ar)-3-(1,1-dimethylheptyl)-1-methoxy-6,6,9-trimethyl-6a,7,10,10a-tetrahydro-6H-enzo[c]chromene (L759633); (6ar,10ar)-3-(1,1-dimethylheptyl)-1-methoxy-6,6-dimethyl-9-methylene-6a,7,8,9,10,10a-hexahydro-6H-benzo[c]chromene (L759656); {4-[4-(1,1-dimethyl-heptyl)-2,6-dimethoxy-phenyl]-6,6-dimethyl-bicyclo-[3.1.1]hept-2-en-2-yl}-methanol (HU308); (2-Methyl-1-propyl-1H-indol-3-yl)-1-naphthalenylmethanone (JWH015); (2-iodo-5-nitro-phenyl)-[1-(1-methyl-piperidin-2-ylmethyl)-1H-indol-3-yl]-1-methanone (AM-1241); 3-(1,1-dimethyl-butyl)-6,6,9-trimethyl-6a,7,10,10a-tetrahydro-6H-benzo[c]-chromene (JWH133); 6,6,9-trimethyl-3-pentyl-6a,7,8,10a-tetrahydro-6H-benzo[c]chromen-1-ol; dronabinol; 5-(1,1-dimethyl-heptyl)-2-[5-hydroxy-2-(3-hydroxy-propyl)-cyclohexyl]-phenol (CP-55,940); (2-methyl-3-morpholin-4-ylmethyl-3,4-dihydro-5-oxa-2a-aza-acenaphthylen-1-yl)-naphthalen-1-yl-methanone (WIN-55,212-2); (6aR,10aR)-9-(Hydroxymethyl)-6,6-dimethyl-3-(2-methyloctan-2-yl)-6a,7,10,10a-tetrahydrobenzo[c]chromen-1-ol (HU210); arachidonyl-2-chloroethylamid (ACEA); arachidonylcyclopropylamide (ACPA); methanandamide; anandamide; 2-arachidonoyl glycerol; 2-icosa-5,8,11,14-tetraenyloxy-propane-1,3-diol (noladinether); (−)-(R)-3-(2-Hydroxymethylindanyl-4-oxy)phenyl-4,4,4-trifluorobutyl-1-sulfonate (BAY 38-7271); naphthalen-1-yl-(4-pentyloxynaphthalen-1-yl) methanone (SAB-378); 3-[2-cyano-3-(trifluoromethyl)phenoxy] phenyl 4,4,4-trifluoro-1-butanesulfonic acid ester (BAY 59-3074); 3-(5'-cyano-1',1'-dimethylpentyl)-1-(4-N-morpholino-butyryloxy)-D8-tetrahydrocannabinol hydrochloride (0-1057); delta-9-tetrahydrocannabinol (GW-1000); Butenedioic acid (2E)-, mono[5-(1,1-dimethylheptyl)-2-[(1S,2S,5S)-6,6-dimethyl-4-oxobicyclo[3.1.1]hept-2-yl]-3-hydroxyphenyl]ester (PRS-211375); PRS-211359; PRS-211355; 3-(4-tert-Butyl-2,6-dihydroxy-benzyl)-4-isopropenyl-cyclohexanone (PRS-211096); 2-(2,4-dichloro-phenylamino)-4-trifluoromethyl-pyrimidine-5-carboxylic acid (tetrahydro-pyran-4-ylmethyl)-amide (GW-842166X); and mixtures thereof;

wherein the $CB_2$ antagonist is selected from the group consisting of: N-{1,3,3-trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide (SR-144528), N-(1,3-Benzodioxol-5-ylmethyl)-1,2-dihydro-7-methoxy-2-oxo-8-(pentyloxy)-3-quinolinecarboxamide (JTE-907), 6-Iodo-2-methyl-1-[2-(4-morpholinyl)ethyl]-1H-indol-3-yl](4-methoxyphenyl)methanone (AM630), and mixtures thereof;

wherein the $CB_2$ inverse agonist is selected from the group consisting of: N-{1,3,3-trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide (SR-144528), N-(1,3-Benzodioxol-5-ylmethyl)-1,2-dihydro-7-methoxy-2-oxo-8-(pentyloxy)-3-quinolinecarboxamide (JTE-907), 6-Iodo-2-methyl-1-[2-(4-morpholinyl)ethyl]-1H-indol-3-yl](4-methoxyphenyl)methanone (AM630), and mixtures thereof; and wherein the compounds having both $CB_1$ agonist and $CB_2$ agonist properties is selected from the group consisting of: dronabinol; (6aR,10aR)-9-(Hydroxymethyl)-6,6-dimethyl-3-(2-methyloctan-2-yl)-6a,7,10,10a-tetrahydrobenzo[c]chromen-1-ol (HU210); 2-icosa-5,8,11,14-tetraenyloxy-propane-1,3-diol (noladinether); and mixtures thereof.

15. The pharmaceutical composition of claim 14, wherein the $K_{ATP}$ channel modulator modulates a channel selected from the group consisting of: the Kir6.2/SUR1 $K_{ATP}$ channel, the Kir6.2/SUR2B $K_{ATP}$ channel, the Kir6.1/SUR2B $K_{ATP}$ channel and the Kir6.2/SUR2A $K_{ATP}$ channel.

16. The pharmaceutical composition of claim 1, wherein $K_{ATP}$ channel modulator is selected from the group consisting of: morpholine-4-sulfonic acid [3-(4-chloro-phenyl)-4-phenyl-4,5-dihydro-pyrazol-1-yl]methylamino-methyleneamide and enantiomers; N-{[3,4-chloro-phenyl)-4-(3-fluoro-phenyl)-4,5-dihydro-pyrazol-1-yl]-methylamino-methylene]-N,N-dimethyl-sulfonamide; azepane-1-sulfonic acid [3-(4-chloro-phenyl)-4-phenyl-4,5-dihydro-pyrazol-1-yl]-methylamino-methyleneamide; 4-chloro-N-{[3-(4-chloro-phenyl)-4-phenyl-4,5-dihydro-pyrazol-1-yl]-[(1-methyl-pyrrolidin-3-ylmethyl)-amino]-methylene]-benzenesulfonamide; 1-(4-chloro-phenyl)-5-phenyl-4,5-dihydro-1H-pyrazole-3-carboxamide; N-[3-(4-chloro-phenyl)-4-phenyl-4,5-dihydro-pyrazol-1-yl]-methylamino-methylene-4-trifluoromethyl-benzene-sulfonamide; piperidin-1-sulfonic acid [3-(4-chloro-phenyl)-4-phenyl-4,5-dihydro-pyrazol-1-yl]-methylamino-methyleneamide; piperidin-1-sulfonic acid [3-(4-chloro-phenyl)-4-phenyl-4,5-dihydro-pyrazol-1-yl]-(2-dimethylamino-ethylamino)-methyleneamide; N,N-diethylamino-1-sulfonic acid [3-(4-chloro-phenyl)-4-phenyl-4,5-dihydro-pyrazol-1-yl]-methylsulfanyl-methyleneamide; 2-amino-1-[3-(4-chloro-phenyl)-4-phenyl-4,5-dihydro-pyrazol-1-yl]-3-(3,4-dichloro-phenyl)-propan-1-one; N,N-dimethylamino-1-sulfonic acid [3-(4-chloro-phenyl)-4-phenyl-4,5-dihydro-pyrazol-1-yl]-(2-fluoro-ethylamino)-methyleneamide; piperidine-1-sulfonic [3-(4-chloro-phenyl)-4-(3-fluoro-phenyl)-4,5-hydro-pyrazol-1 yl]-methylamino-methyleneamide; 5-(4-chloro-phenyl)-1-(2,4-dichloro-phenyl)-4,5-dihydro-1H-pyrazole-3-carboxylic acid piperidine-1-ylamide; 1-(4-chloro-phenyl)-5-phenyl-4,5-dihydro-1H-pyrazole-3-carboxylic acid piperidin-1-ylamide; piperidine-1-sulfonic acid [1-(4-chloro-phenyl)-5-phenyl-4,5-dihydro-1H-pyrazol-3-yl]-methylamino-methyleneamide; morpholine-4-sulfonic acid [1-(2,4-dichloro-phenyl)-5-phenyl-4,5-dihydro-1H-pyrazol-3-yl]-methylamino-methyleneamide; 4-chloro-N-[[3-(4-chloro-phenyl)-4-phenyl-4,5-dihydro-pyrazol-1-yl]-(2-fluoro-ethylamino)-methylene]-benzenesulfonamide (ref 1); 4-chloro-N-[[3-(4-chloro-phenyl)-4-phenyl-4,5-dihydro-pyrazol-1-yl]-(2-fluoro-ethylamino)-methylene]-benzenesulfonamide (ref 2); N-{amino-[3-(4-chloro-phenyl)-4-phenyl-4,5-dihydro-pyrazol-1-yl]-methylene}-4-chloro-benzenesulfonamide; 4-chloro-N-[3-(4-chloro-phenyl)-4-phenyl-4,5-dihydro-pyrazole-1-carbonyl]-benzenesulfonamide; 4-chloro-N-[[3-(4-chloro-phenyl)-4-phenyl-4,5-dihydro-pyrazol-1-yl]-(2-ethylamino-ethylamino)-methylene]-benzenesulfonamide; 4-chloro-N-{[3-(4-chloro-phenyl)-4-phenyl-4,5-dihydro-pyrazol-1-yl]-[(1-methyl-pyrrolidin-2-ylmethyl)-amino]-methylene}-benzenesulfonamide; 4-chloro-N-[[3-(4-chloro-phenyl)-4-phenyl-4,5-dihydro-pyrazol-1-yl]-(4-pyrrolidin-1-yl-butylamino)-methylene]-benzenesulfonamide; 4-chloro-N-{[3-(4-chloro-phenyl)-4-phenyl-4,5-dihydro-pyrazol-1-yl]-[(pyridin-3-ylmethyl)-amino]-methylene}-benzenesulfonamide; 1-[3-(4-chloro-phenyl)-4-phenyl-4,5-dihydro-pyrazol-1-yl]-3-(1H-indol-2-yl)-2-methylamino-propan-1-one; 2-[3-(4-chloro-phenyl)-4-phenyl-4,5-dihydro-pyrazol-1-yl]-5-ethyl-4,5-dihydro-oxazole; 4-chloro-N-[[3-(4-chloro-phenyl)-4-phenyl-4,5-dihydro-pyrazol-1-yl]-(3-hydroxy-2,2-dimethyl-propylamino)-methylene]-benzenesulfonamide; N,N-diethylamino-1-sulfonic acid [3-(4-chloro-phenyl)-4-hydroxy-4-phenyl-4,5-dihydro-pyrazol-1-yl]-methylamino-methyleneamide; 5-(4-bromo-phenyl)-1-(2,4-dichloro-phenyl)-1H-pyrazole-3-carbonitrile; 8-chloro-1-(2,4-dichloro-phenyl)-1,3a,4,5,6,10b-hexahydro-1,2-diaza-benzo[e]azulene-3-carboxylic acid piperidin-1-ylamide; 5-(4-bromo-phenyl)-1-(2,4-dichloro-phenyl)-3-[2-(3,5-difluoro-phenyl)-2-methanesulfonyl-vinyl]-4-methyl-1H-pyrazole; piperidine-1-carboxylic acid [5-(4-chloro-phenyl)-1-(2,4-dichloro-phenyl)-4-methyl-1H-pyrazol-3-yl]-amide; 1-(4-chloro-phenyl)-2-(2,4-dichloro-phenyl)-5-ethylsulfanyl-1H-imidazole-4-carboxylic acid piperidin-1-ylamide; 2-(2,4-dichloro-phenyl)-1-(4-trifluoromethyl-phenyl)-1H-imidazole-4-carboxylic acid piperidin-1-ylamide; 1-(4-chloro-phenyl)-2-(2,4-dichloro-phenyl)-5-methylsulfanyl-1H-imidazole-4-carboxylic acid piperidin-1-ylamide; 1-(4-chloro-phenyl)-2-(2,4-dichloro-phenyl)-1H-imidazole-4-carboxylic acid piperidin-1-ylamide; 1-(4-chloro-phenyl)-2-(2,4-dichloro-phenyl)-5-methyl-1H-imidazole-4-carboxylic acid (4-hydroxy-cyclo-hexyl)-amide; 1-(4-chloro-phenyl)-2-(2,4-dichloro-phenyl)-5-methyl-1H-imidazole-4-carboxylic acid azepan-1-ylamide; 2-(2,4-dichloro-phenyl)-5-ethyl-1-phenyl-1H-imidazole-4-carboxylic acid piperidin-1-ylamide; 2-(1,5-dimethyl-1H-pyrrol-2-yl)-5-ethyl-1-phenyl-1H-imidazole-4-carboxylic acid cyclohexylamide; 1-(4-chloro-phenyl)-5-ethyl-2-(3-methyl-pyridin-2-yl)-1H-imidazole-4-carboxylic acid piperidin-1-ylamide; 1-(4-chloro-phenyl)-2-(2,4-dichloro-phenyl)-5-ethyl-1H-imidazole-4-carboxylic acid piperidin-1-ylamide; 1-(4-bromo-phenyl)-2-(2,4-dichloro-phenyl)-5-ethyl-1H-imidazole-4-carboxylic acid piperidin-1-ylamide; 1-(4-bromo-phenyl)-5-chloro-2-(2,4-dichloro-phenyl)-1H-imidazole-4-carboxylic acid piperidin-1-ylamide; 1-(4-bromo-phenyl)-2-(2,4-dichloro-phenyl)-5-ethyl-1H-imidazole-4-carboxylic acid cyclohexylamide; 1-(4-bromo-phenyl)-2-(2,4-dichloro-phenyl)-5-ethyl-1H-imidazole-4-carboxylic acid pentylamide; 4-(4-chloro-phenyl)-5-(2,4-dichloro-phenyl)-1-methyl-1H-imidazole-2-carboxylic acid cyclohexylamide; 4-(4-chloro-phenyl)-5-(2,4-dichloro-phenyl)-3-methyl-1H-imidazole-2-carboxylic acid cyclohexylamide; 1-(5-chloro-pyridin-2-yl)-2-(2,4-dichloro-phenyl)-5-ethyl-1H-imidazole-4-carboxylic acid piperidin-1-ylamide; 1-(4-chloro-phenyl)-5-ethyl-2-(3-methyl-pyridin-2-yl)-1H-imidazole-4-carboxylic acid cyclohexylamide; 1-(4-chloro-phenyl)-2-(2,4-dichloro-phenyl)-5-methyl-1H-imidazole-4-carboxylic acid (4-trifluoromethyl-phenyl)-amide; 2-(2,4-dichloro-phenyl)-5-methyl-1-pyridin-2-yl-1H-imidazole-4-carboxylic acid piperidin-1-ylamide; 1-(4-chloro-phenyl)-2-(2,4-dichloro-phenyl)-5-fluoromethyl-1H-imidazole-4-carboxylic acid piperidin-1-ylamide; 1-(4-chloro-phenyl)-2-(2,4-dichloro-phenyl)-5-hydroxymethyl-1H-imidazole-4-carboxylic acid piperidin-1-ylamide; 1-(4-chloro-phenyl)-2-(2,4-dichloro-phenyl)-5-methylsulfanyl-1H-imidazole-4-carboxylic acid cyclohexylamide; 1-(4-chloro-phenyl)-2-(2,4-dichloro-phenyl)-5-methanesulfonyl-1H-imidazole-4-carboxylic acid piperidin-1-ylamide; 1-(4-chloro-phenyl)-2-(2,4-dichloro-phenyl)-5-methanesulfinyl-1H-imidazole-4-carboxylic acid piperidin-1-ylamide; 5-(4-chloro-phenyl)-4-(2,5-dichloro-phenyl)-1-methyl-1H-imidazole-2-carboxylic acid piperidin-1-ylamide; 2-(2-chloro-phenyl)-1-(5-chloro-pyridin-2-yl)-5-ethyl-1H-imidazole-4-carboxylic acid piperidin-1-ylamide; 1-(4-chloro-phenyl)-2-(2,4-dichloro-phenyl)-5-(2,2,2-trifluoro-ethyl)-1H-imidazole-4-carboxylic acid piperidin-1-ylamide; N-[1-(4-chloro-phenyl)-2-(2,4-dichloro-phenyl)-5-methyl-1H-imidazol-4-yl]-benzamide; 1-(4-chloro-phenyl)-2-(2,4-dichloro-phenyl)-5-pyrrolidin-1-ylmethyl-1H-imidazole-4-carboxylic acid piperidin-1-ylamide; 2-[1-(4-chloro-phenyl)-2-(2,4-dichloro-phenyl)-5-methyl-1H-imidazol-4-yl]-hexan-2-ol; 1-(4-chloro-phenyl)-2-(2,4-dichloro-phenyl)-5-methyl-4-pentyl-1H-imidazole; 2,5-dimethyl-1-phenyl-1H-imidazole-4-carboxylic acid adamantan-2-ylamide; 1-(4-chloro-phenyl)-2-(2-chloro-phenyl)-5-methylsulfanyl-1H-imidazole-4-carboxylic acid piperidin-1-ylamide; 2-(2-chloro-phenyl)-1-(4-trifluoromethyl-phenyl)-1H-imidazole-4-carboxylic acid piperidin-1-ylamide; 5-(4-chloro-phenyl)-1-(2,4-dichloro-phenyl)-1H-[1,2,4]-triazole-3-carboxylic acid pyrrolidin-1-ylamide; 1-(4-chloro-phenyl)-5-(2,4-dichloro-phenyl)-1H-[1,2,4]triazole-3-carboxylic acid piperidin-1-yl-amide; 1-{(4-chloro-benzene-sulfonylimino)-[3-(4-chloro-phenyl)-4-phenyl-4,5-dihydro-pyrazol-1-yl]-methyl}-piperidine-4-carboxylic acid amide; 4-chloro-N-{[3-(4-chloro-phenyl)-4-phenyl-4,5-dihydro-pyrazol-1-yl]-[2-(2-oxo-pyrrolidin-1-yl)-ethylamino]-methylene}-benzenesulfonamide; 4-chloro-N-[[3-(4-chloro-phenyl)-4-phenyl-4,5-dihydro-pyrazol-1-yl]-(2-cyano-ethylamino)-methylene]-benzene-sulfonamide; 4-chloro-N-[[3-(4-chloro-phenyl)-4-phenyl-4,5-dihydro-pyrazol-1-yl]-(methoxy-methyl-amino)-methylene]-benzenesulfonamide; 4-chloro-N-{[3-(4-chloro-phenyl)-4-phenyl-4,5-dihydro-pyrazol-1-yl]-[4(piperidin-4-ylmethyl)-amino]-methylene}-benzenesulfonamide; 4-chloro-N-[[3-(4-chloro-phenyl)-4-phenyl-4,5-dihydro-pyrazol-1-yl]-(piperidin-4-ylamino)-methylene]-benzenesulfonamide; morpholine-4-sulfonic acid [3-(4-chloro-phenyl)-4-phenyl-4,5-dihydro-pyrazol-1-yl]-(cyclopropylmethyl-amino)-methyleneamide; and mixtures thereof.

17. The pharmaceutical composition of claim 1, wherein CBx modulator is selected from the group consisting of: 3-(1,1-dimethyl-butyl)-6,6,9-trimethyl-6a,7,10,10a-tetrahydro-6H-benzo[c]chromene; N-{1,3,3-trimethyl-endo-(1S)-bicyclo[2.2.1]hept-2-yl}-1-[1-(4-methyl)-benzyl-5-(4-chloro-3-methyl-phenyl)-1H-pyrazol-3-carboxamide; 2-iodo-5-nitro-phenyl)-[1-(1-methyl-piperidin-2-ylmethyl)-1H-indol-3-yl]-methanone; [4-[4-(1,1-dimethyl-heptyl)-2,6-dimethoxy-phenyl]-6,6-dimethyl-bicyclo[3.1.1]hept-2-en-2-yl}-methanol; 3-(1,1-dimethyl-heptyl)-9-hydroxymethyl-6,6-dimethyl-6a,7,10,10a-tetrahydro-6H-enzo[c]chromen-1-ol; icosa-5,8,11,14-tetraenoic acid 2-hydroxy-1-hydroxymethyl-ethyl ester; 1-aziridin-1-yl-henicosa-6,9,12,15-tetraen-2-one; noladineether; 4,4,4-trifluoro-butane-1-sulfinic acid 3-(2-hydroxymethyl-indan-4-yloxy)-phenyl ester; 7-methoxy-2-oxo-8-pentyloxy-1,2-dihydro-quinoline-3-carboxylic acid (benzo[1,3]dioxol-5-ylmethyl)-amide; N-(1-{4-[4-chloro-2-(2-fluoro-benzenesulfonyl)-benzenesulfonyl]-phenyl}-ethyl)-methanesulfonamide; [6-iodo-2-methyl-1-(2-morpholin-4-yl-ethyl)-2,3-dihydro-1H-indol-3-yl]-(4-methoxy-phenyl)-methanone; 1-(4-chloro-phenyl)-2-(2-chloro-phenyl)-5-ethyl-1H-imidazole-4-carboxylic acid piperidin-1-ylamide; (2-methyl-1-propyl-2,3-dihydro-1H-indol-3-yl)-naphthalen-1-yl-methanone; 5-(1,1-dimethyl-heptyl)-2-[5-hydroxy-2-(3-hydroxy-propyl)-cyclohexyl]-phenol and enantiomers; (2-methyl-3-morpholin-4-ylmethyl-3,4-dihydro-5-oxa-2a-azacenaphthylen-1-yl)-naphthalen-1-yl-methanone; 5-(4-chloro-phenyl)-1-(2,4-dichloro-phenyl)-4-methyl-1H-pyrazole-3-carboxylic acid piperidin-1-ylamide; 5-(4-bromo-phenyl)-1-(2,4-dichloro-phenyl)-4-ethyl-1H-pyrazole-3-carboxylic acid piperidin-1-ylamide; 1-[bis-(4-chloro-phenyl)-methyl]-3-[(3,5-difluorophenyl)-methanesulfonyl-methylene]-azetidine; 4-chloro-N-{[3-(4-chloro-phenyl)-4-phenyl-4,5-dihydro-pyrazol-1-yl]-methylamino-methylene}-benzenesulfonamide and enantiomers; N-{amino-[3-(4-chloro-phenyl)-4-phenyl-4,5-dihydro-pyrazol-1-yl]-methylene}-4-chloro-benzene-sulfonamide; N-{[3-(4-chloro-phenyl)-4-pyridin-3-yl-4,5-dihydro-pyrazol-1-yl]-methylamino-methylene}-4-trifluoromethyl-benzenesulfonamide; chloro-N-{[3-(4-chloro-phenyl)-4-pyridin-3-yl-4,5-dihydro-pyrazol-1-yl]-methylamino-methylene}-benzenesulfonamide; 4-chloro-N-{[3-(4-chloro-phenyl)-4-(3-fluoro-phenyl)-4,5-dihydro-pyrazol-1-yl]-methoxyamino-methylene}-benzenesulfonamide; morpholine-4-sulfonic acid [3-(4-chloro-phenyl)-4-phenyl-4,5-dihydro-pyrazol-1-yl]-methylamino-methyleneamide; and mixtures thereof.

* * * * *